(12) United States Patent
Poirier et al.

(10) Patent No.: US 12,371,502 B2
(45) Date of Patent: *Jul. 29, 2025

(54) ANTIBODIES DIRECTED AGAINST CD127

(71) Applicant: OSE Immunotherapeutics, Nantes (FR)

(72) Inventors: Nicolas Poirier, Treillières (FR); Caroline Mary, Sainte-Pazanne (FR); Bernard Vanhove, Rezé (FR)

(73) Assignee: OSE IMMUNOTHERAPEUTICS, Nantes (FR)

( * ) Notice: Subject to any disclaimer, the term of this patent is extended or adjusted under 35 U.S.C. 154(b) by 108 days.

This patent is subject to a terminal disclaimer.

(21) Appl. No.: 17/941,885

(22) Filed: Sep. 9, 2022

(65) Prior Publication Data
US 2023/0340133 A1    Oct. 26, 2023

Related U.S. Application Data

(60) Continuation of application No. 16/532,000, filed on Aug. 5, 2019, now Pat. No. 11,440,964, which is a division of application No. 15/317,355, filed as application No. PCT/EP2015/062993 on Jun. 10, 2015, now Pat. No. 10,428,152.

(60) Provisional application No. 62/010,117, filed on Jun. 10, 2014.

(30) Foreign Application Priority Data

Jan. 23, 2015  (EP) ..................................... 15305078

(51) Int. Cl.
| | |
|---|---|
| *A61K 39/00* | (2006.01) |
| *C07K 16/28* | (2006.01) |
| *G01N 33/50* | (2006.01) |
| *G01N 33/68* | (2006.01) |

(52) U.S. Cl.
CPC ..... *C07K 16/2866* (2013.01); *G01N 33/5041* (2013.01); *G01N 33/6854* (2013.01); *A61K 2039/505* (2013.01); *C07K 2317/24* (2013.01); *C07K 2317/34* (2013.01); *C07K 2317/565* (2013.01); *C07K 2317/732* (2013.01); *C07K 2317/76* (2013.01); *C07K 2317/77* (2013.01); *C07K 2317/92* (2013.01); *C07K 2317/94* (2013.01); *G01N 2333/5418* (2013.01); *G01N 2333/70546* (2013.01); *G01N 2333/7155* (2013.01); *G01N 2500/00* (2013.01)

(58) Field of Classification Search
CPC .............................................. A61K 2039/505
See application file for complete search history.

(56) References Cited

U.S. PATENT DOCUMENTS

| | | |
|---|---|---|
| 9,447,182 B2 | 9/2016 | Brouard et al. |
| 11,440,964 B2 * | 9/2022 | Poirier ................... A61P 11/00 |
| 2011/0287000 A1 | 11/2011 | Leung et al. |

FOREIGN PATENT DOCUMENTS

| | | |
|---|---|---|
| WO | 2007140472 A2 | 12/2007 |
| WO | 2010/017468 A1 | 2/2010 |
| WO | 2010085643 A1 | 7/2010 |
| WO | 2011/094259 A2 | 8/2011 |
| WO | 2011/104687 A1 | 9/2011 |
| WO | 2013056984 A1 | 4/2013 |
| WO | 2017149394 A1 | 9/2017 |

OTHER PUBLICATIONS

Adams et al., "Heterologous Immunity Provides a Potent Barrier to Transplantation Tolerance", The Journal of Clinical Investigation, Jun. 2003, pp. 1887-1895 vol. 111 No. 12.

Chung et al., "Prevention of Graft-Versus-Host Disease by Anti-IL-7RAlpha Antibody", Blood Journal, Oct. 15, 2007, pp. 2803-2810, vol. 110 No. 8.

Colman, "Effects of Amino Acid Sequence Changes on Antibody-Antigen Interactions", Research in Immunology, 1994, pp. 33-36, vol. 145.

International Search Report for PCT/EP2015/062993 dated Jul. 17, 2015.

(Continued)

*Primary Examiner* — Prema M Mertz
(74) *Attorney, Agent, or Firm* — Thompson Coburn LLP; William A. Holtz

(57) ABSTRACT

The invention relates to antibodies directed against CD127, the alpha chain of the interleukin 7 (IL-7) receptor IL-7R), and which have antagonist properties for IL-7-IL-7R interaction, may present cytotoxic activity against CD127 positive cells but do not increase the maturation of dendritic cells (DCs) induced by TSLP, a cytokine also using CD127 as part of its receptor. Alternatively, or in addition, these antibodies do not induce the internalization of CD127 and/or inhibit the IL7-induced internalization of CD127. According to another aspect of the invention antibodies are provided which recognize a human CD127 epitope comprising sequences from the 2b site of CD127, in particular the epitope comprising comprises the human CD127 sequences of domain D1 and of the 2b site of CD127, in particular the epitope comprises at least one sequence from D1 comprising SEQ ID No: 115 (in particular comprising SEQ ID No: 110) and/or SEQ ID No: 111 and/or a sequence from the 2b site comprising the sequence of SEQ ID No: 116 and optionally also comprises SEQ ID No: 117 (in particular comprises SEQ ID No: 111). The antibodies of the invention are suitable for use in order to remedy to a condition diagnosed in a human patient which results from pathogenesis related to lymphopoiesis, when IL-7 signalling pathways provide contribution to said pathogenesis, especially when an increase in the maturation, more precisely the upregulation of costimulatory molecules, of dendritic cells is undesirable.

21 Claims, 28 Drawing Sheets

Specification includes a Sequence Listing.

(56) References Cited

OTHER PUBLICATIONS

Janeway et al., "Antigen Recognition by B-Cells and T-Cell Receptors", Immunobiology, 5th Edition, 2001, pp. 100-105, Chapter 3.
Liu et al., "Crucial Role of Interleukin-7 in T Helper Type 17 Survival and Expansion in Autoimmune Disease", Nature Medicine, Feb. 2010, pp. 191-199 vol. 16 No. 2.
Liu et al., "Retraction: Crucial Role of Interleukin-7 in T Helper Type 17 Survival and Expansion in Autoimmune Disease", Nature Medicine, Dec. 2013, pp. 1673, vol. 19 No. 12.
Michel et al., "Patients with Relapsing-Remitting Multiple Sclerosis have Normal Treg Function When Cells Expressing IL-7 Receptor Alpha-Chain are Excluded from the Analysis", The Journal of Clinical Investigation, Oct. 2008, pp. 3411-3419, vol. 118 No. 10.
Paul, "Fv Structure and Diversity in Three Dimensions", Fundamental Immunology, 3rd Edition, 1993, pp. 292-295, Chapter 9, Raven Press Ltd., New York.
Racape et al., "Interleukin 7 Receptor Alpha as a Potential Therapeutic Target in Transplantation", Archivum Immunologiae et Therapia Experimentalis, 2009, pp. 253-261.
Rudikoff et al., "Single Amino Acid Substitution Altering Antigen-Binding Specificity", Proceedings of the National Acadamy of the Sciences USA, Mar. 1982, pp. 1979-1983, vol. 79.
Tamura et al., "Structural Correlates of an Anticarcinoma Antibody: Identification of Specificity-Determining Residues (SDRs) and Development of a Minimally Immunogenic Antibody Variant by Retention of SDRs Only", The Journal of Immunology, pp. 1432-1441, vol. 164.
Written Opinion for PCT/EP2015/62993 dated Jul. 17, 2015.
Ducancel et al., "Molecular Engineering of Antibodies for Therapeutic and Disgnostic Purposes", mAbs, Jul./Aug. 2012, vol. 4, Issue 4, pp. 445-457.
Jones et al., "Deimmunization of Monoclonal Antibodies", Methods in Molecular Biology, Feb. 2009, pp. 405-423.
Registration of OSE Immunotherapeutics as company resulting from merger with EFFIMUNE dated Jan. 7, 2016 (English Translation).
Registration of OSE Immunotherapeutics as company resulting from merger with EFFIMUNE dated Jan. 7, 2016 (Original).
Dooms, "Interleukin-7: Fuel for the Autoimmune Attack", Journal of Autoimmunity, 2013, pp. 1-9.
Lundström et al., "IL-7 in Human Health and Disease", National Institutes of Health, Jun. 2012, pp. 218-224, vol. 24, No. 3.
Mackall et al., "Harnessing the Biology of IL-7 for Therapeutic Application", Nature, May 2011, pp. 331-342, vol. 11.
Hartgring et al., "Blockade of the Interleukin-7 Receptor Inhibits Collagen-Induced Arthritis and is Associated with Reduction of T Cell Activity and Proinflammatory Mediators", Arthritis & Rheumatism, Sep. 2010, pp. 2716-2725, vol. 62, No. 9.
Gonzalez-Quintial et-al., "Systemic Autoimmunity and Lymphoproliferation Are Associated with Excess IL-7 and Inihibited by IL-7Ra Blockade", PLoS one, Nov. 2011, 12 pages, vol. 6, Issue 11.
Jin et al., "Interleukin-7 Enhances Th1 Response to Promote the Development of Sjogren's Syndrome-Like Autoimmune Exocrinopathy", Arthritis Rheum., Aug. 2013, 19 pages, vol. 65, No. 8.
Mai et al., "IL-7 Receptor Blockade Following T Cell Depletion Promotes Long-Term Allograft Survival", The Journal of Clinical Investigation, Apr. 2014, pp. 1723-1733, vol. 124, No. 4.
Lee et al., "IL-7 Promotes TH1 Cell Differentiation and Its Level in Serum Predicts Response to Interferon-ß in Multiple Sclerosis", Sci. Transl. Med., Jul. 27, 2011, 19 Pages, vol. 27, No. 3.
Lee et al., "Anti-IL-7 Receptor-a Reverses Established Type 1 Diabetes in Nonobese Diabetic Mice By Modulating Effector T-Cell Function", PNAS, Jul. 31, 2012, Correction, pp. 12674-12679, vol. 109, No. 31.
Penaranda et al., "IL-7 Receptor Blockade Reverses Autoimmune Diabetes by Promoting Inhibition of Effector/ Memory T Cells", PNAS, Jul. 31, 2012, pp. 12668-12673, vol. 109, No. 31.
Piotti et al., "Guiding Postablative Lymphocyte Reconstitution as a Route Toward Transplantation Tolerance", American Journal of Transplantation, 2014, pp. 1678-1689, vol. 14.
Walline et al., "IL-7Ra Confers Susceptibility to Experimental Autoimmune Encephalomyelitis", Genes Immun., Jan. 2011, 14 Pages, vol. 12, No. 1.
Wang et al., "Use of the Inhibitory Effect of Apoptotic Cells on Dendritic Cells for Graft Survaval Via T-Cell Deletion and Regulatory T Cells", American Journal of Transplantation, 2006, pp. 1297-1311, vol. 6.
Liu et al., "Physical Disruption of Skin During Poxvirus Immunization is Critical for the Generation of Highly Protective T Cell-Mediated Immunity", Nature Medicine, Feb. 2010, pp. 224-227, vol. 16, No. 2.
Al-Rawi et al., "Interleukin-7 (IL-7) and IL-7 receptor (IL-7R) signalling complex in human solid tumours", Histol Histopathol, 2003, pp. 911-923, vol. 18.
Kelly et al., "Potential Contribution of IL-7 to Allergen-Induced Eosinophilic Airway Inflammation in Asthma1", The Journal of Immunology, Feb. 2009, pp. 1404-1410, vol. 182, No. 3.
Jin et al., "Systemic administration of TLR3 agonist induces IL-7 expression and IL-7-dependent CXCR3 ligand production in the lung", J Leukoc Biol, 2013, pp. 413-425, vol. 93(3), online https://pmc.ncbi.nlm.nih.gov/articles/PMC4050520/.

\* cited by examiner

A.
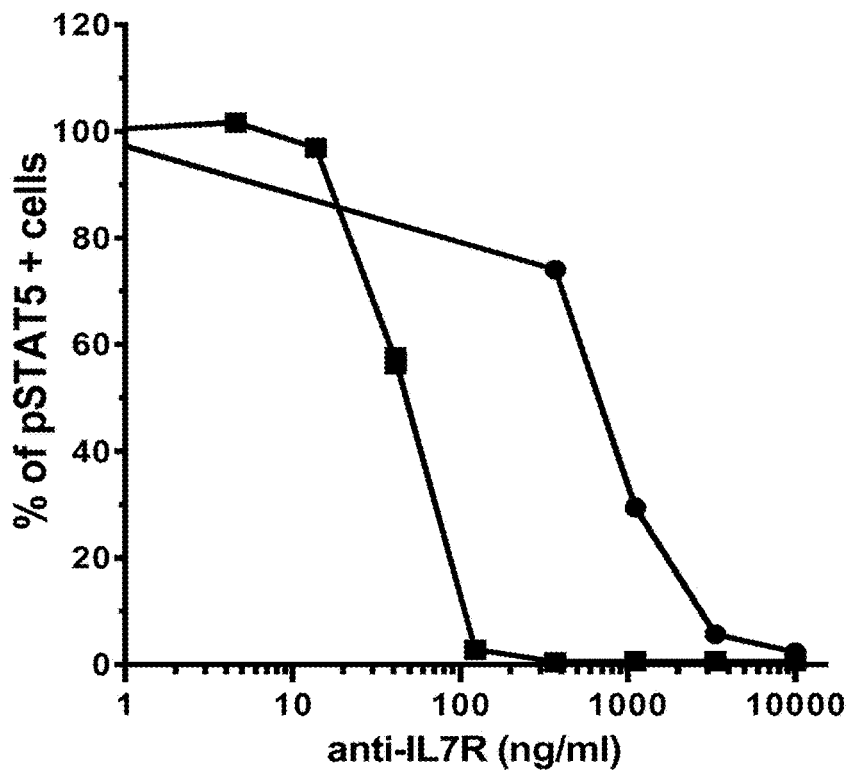
B.
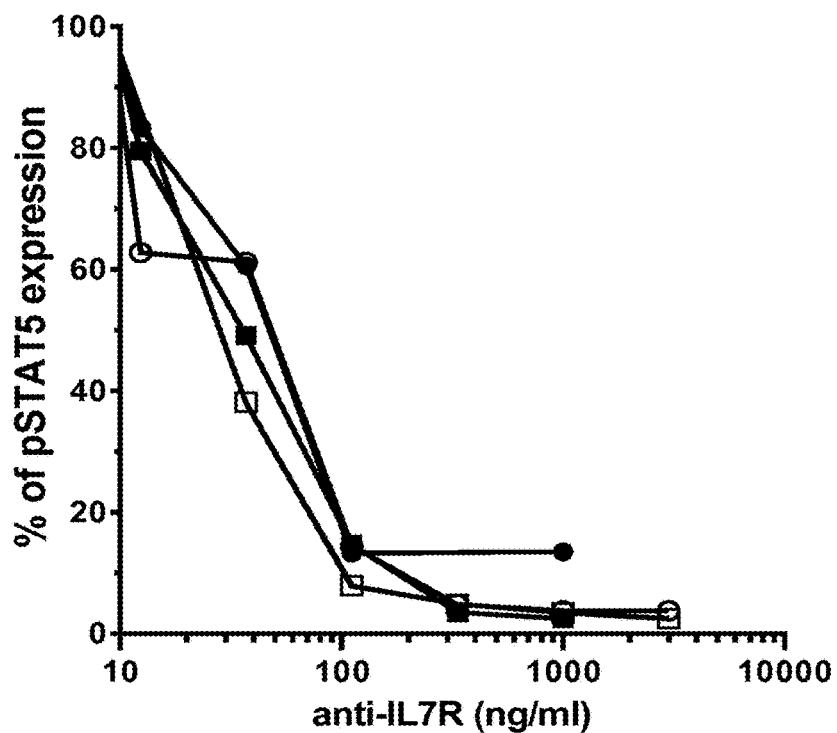
Figure 2

A.
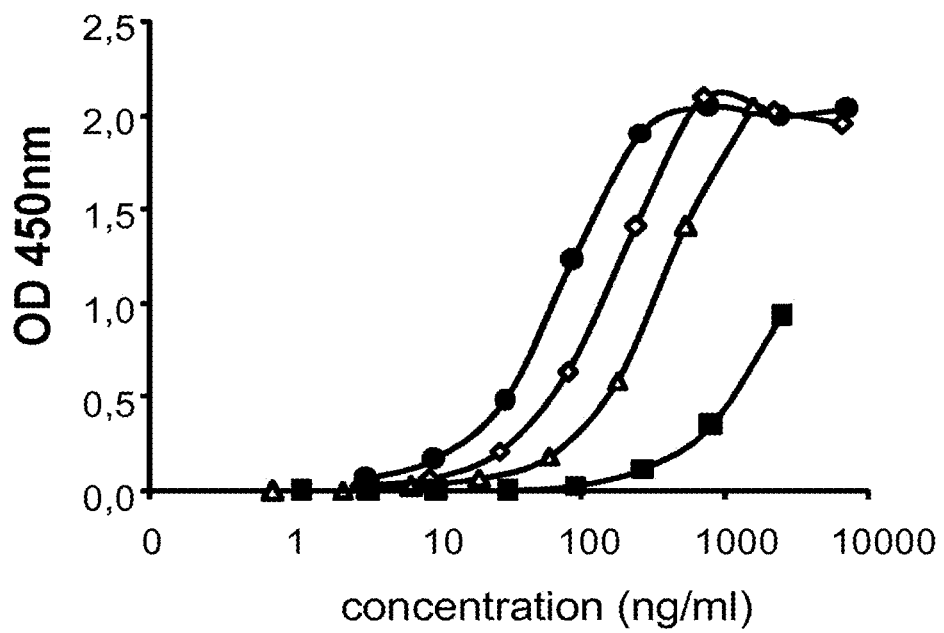
B.
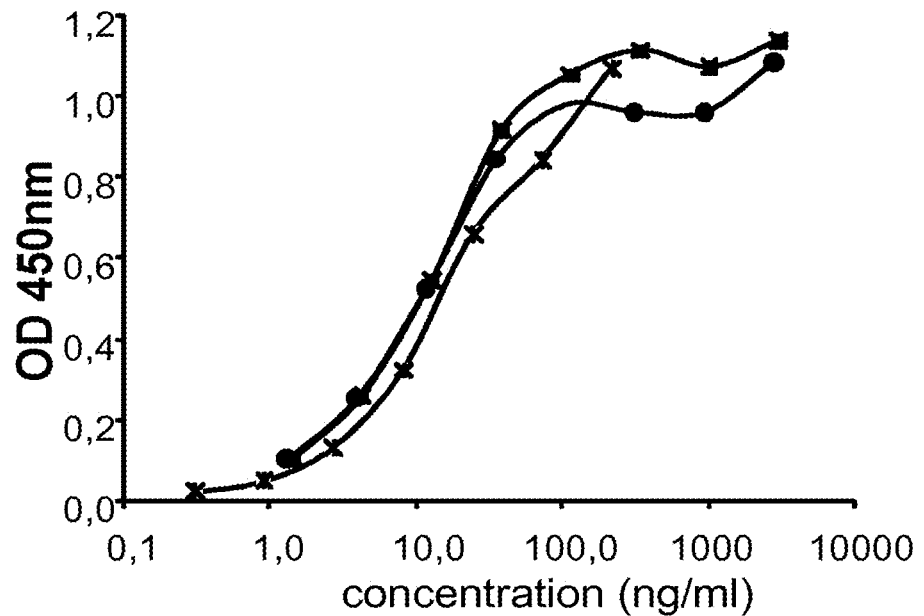
Figure 4

A.
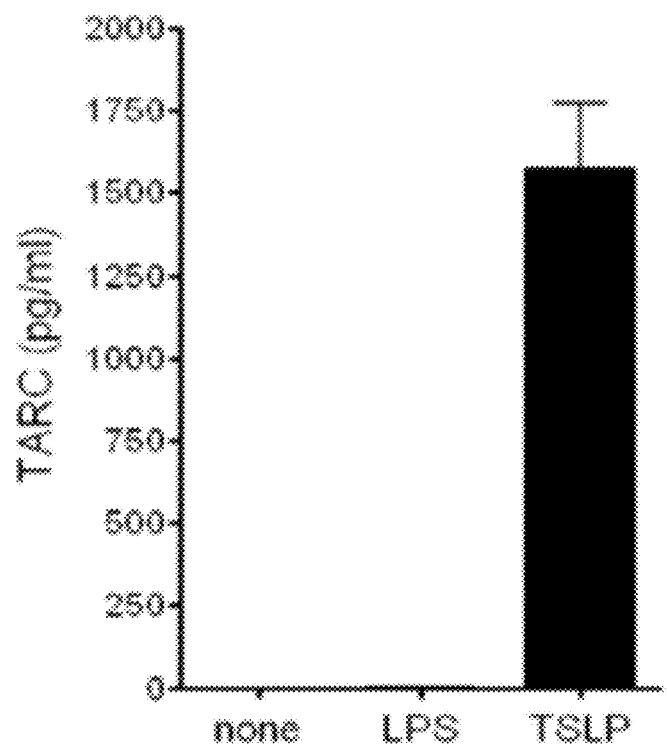
B.
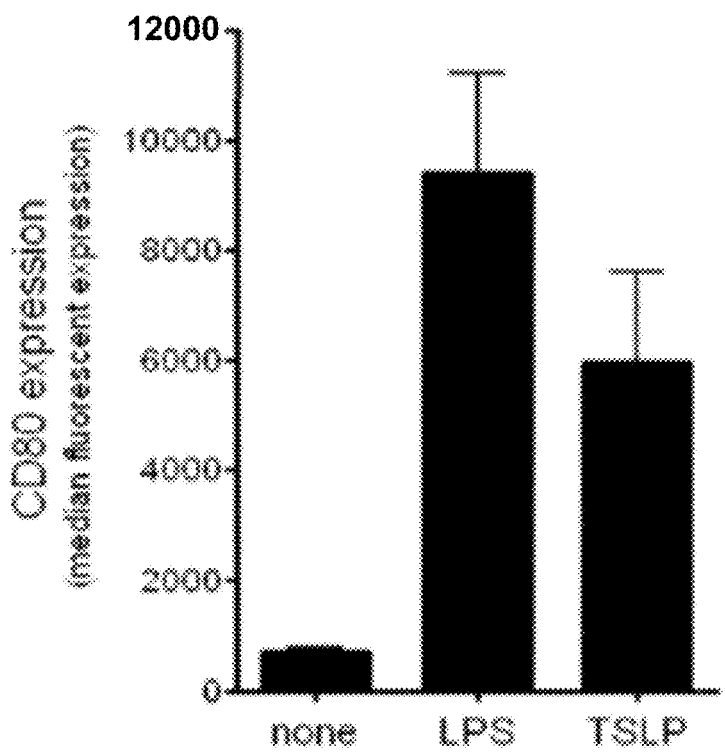
FIGURE 5

A.
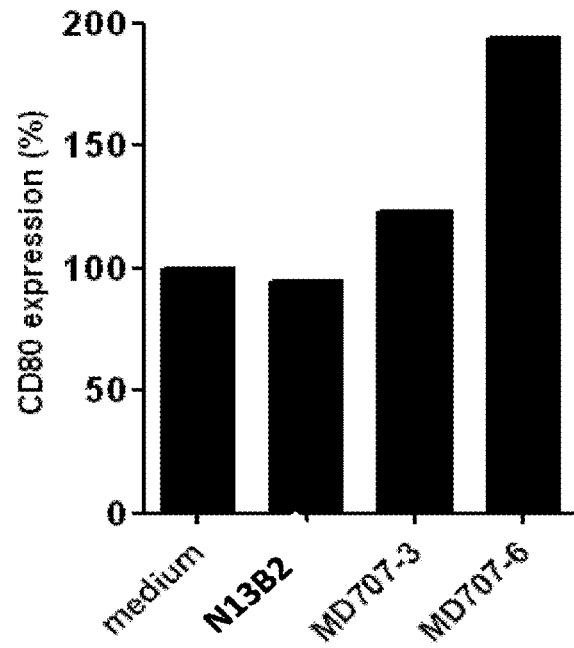
B.
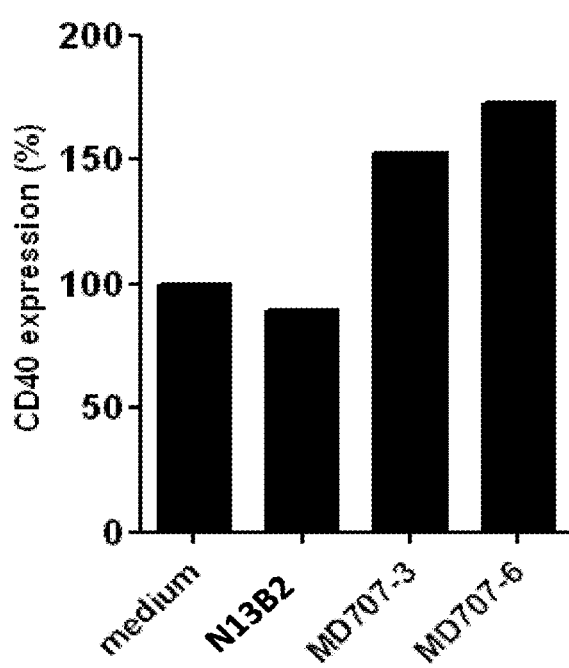
Figure 7

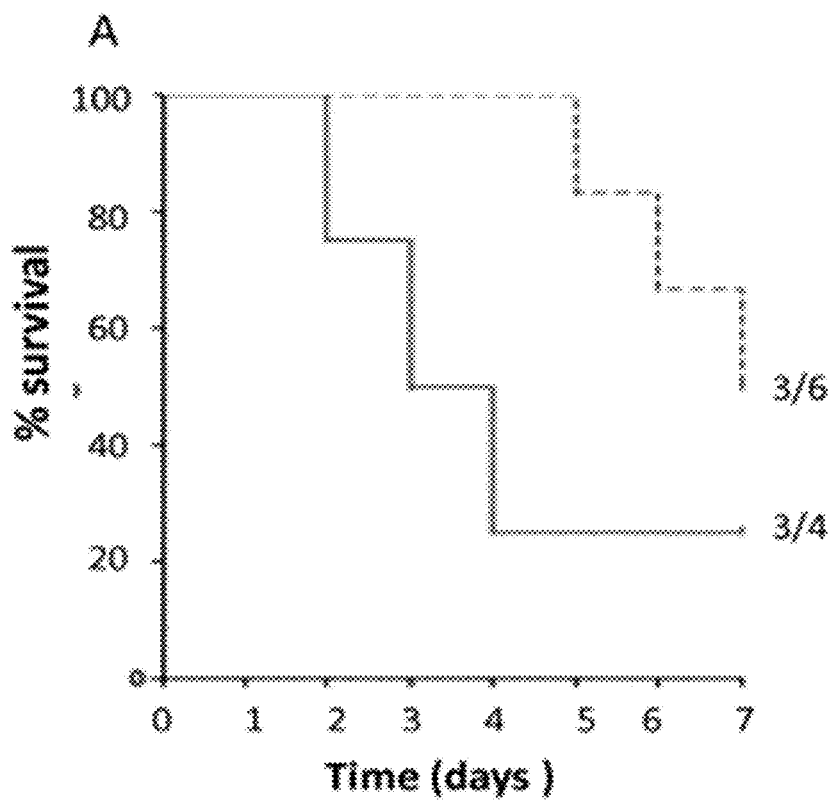
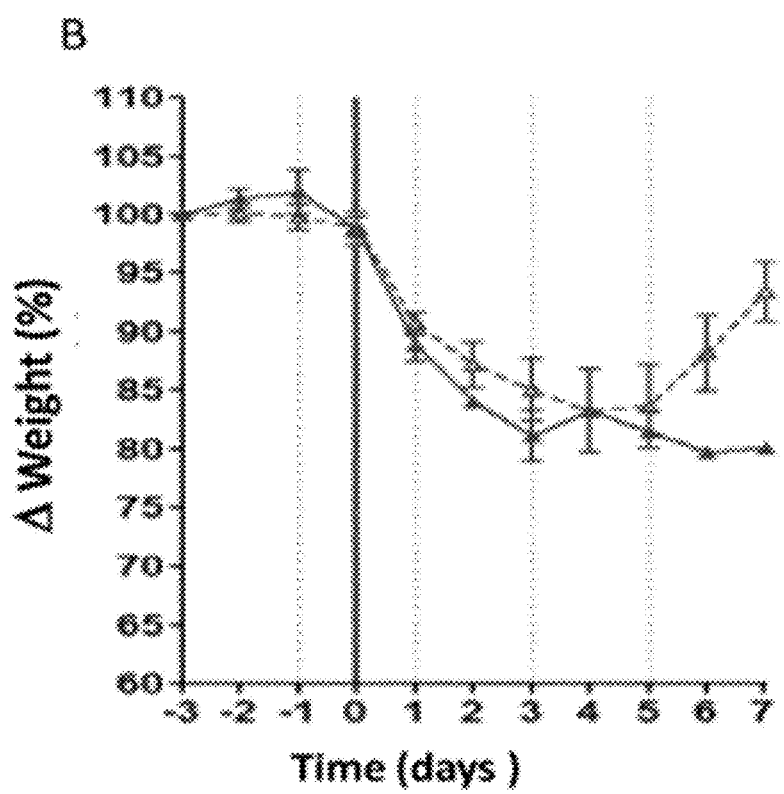
FIGURE 9

VH-FcG1M (E333A) – DNA (SEQ ID NO:1)
GCGGTGCAGCTGGTGGAGTCTGGGGGAGGCCTAGTGCAGCCTGGAGGGTCCCT
GAAACTCTCCTGTGCAGTCTCAGGA<u>TTCACTCTCAGTGACTATTACATGGCCTGGG</u>
TCCGCCAGGCTCCAAAGAAGGGTCTGGAATGGGTCGCA<u>ACCATTAGTGCCAGTGG</u>
<u>GCTCAGAACTTACTATCCAGACTCCGTGAAGGGC</u>CGCTTCACTATCTCCAGAGAT
GATGCAAAAAGGAGCCTCTTCCTGCAAATGACCAGTCTGAAGTCTGAGGACACGG
CCACTTATTACTGTGCAAGA<u>CCGATGTCTGCACACTATGGTTTTAACTACTTTGATT</u>
<u>AC</u>TGGGGCCAAGGAGTCATGGTCACAGTCTCCTCAgctagcaccaagggcccatcggtcttccc
cctggcaccctcctccaagagcacctctgggggcacagcggccctgggctgcctggtcaaggactacttccccgaaccg
gtgacggtgtcgtggaactcaggcgccctgaccagcggcgtgcacaccttcccggctgtcctacagtcctcaggactctac
tccctcagcagcgtggtgaccgtgccctccagcagcttgggcacccagacctacatctgcaacgtgaatcacaagccca
gcaacaccaaggtggacaagaaagttgagcccaaatcttgtgacaaaactcacacatgcccaccgtgcccagcacctg
aactcctggggggaccgtcagtcttcctcttccccccaaaacccaaggacaccctcatgatctcccggacccctgaggtca
catgcgtggtggtggacgtgagccacgaagaccctgaggtcaagttcaactggtacgtggacggcgtggaggtgcataa
tgccaagacaaagccgcgggaggagcagtacaacagcacgtaccgtgtggtcagcgtcctcaccgtcctgcaccagg
actggctgaatggcaaggagtacaagtgcaaggtctccaacaaagccctcccagcccccatcgcgaaaaccatctcca
aagccaaagggcagccccgagaaccacaggtgtacaccctgcccccatcccgggaggagatgaccaagaaccagg
tcagcctgacctgcctggtcaaaggcttctatcccagcgacatcgccgtggagtgggagagcaatgggcagccggaga
acaactacaagaccacgcctcccgtgctggactccgacggctccttcttcctctacagcaagctcaccgtggacaagagc
aggtggcagcaggggaacgtcttctcatgctccgtgatgcatgaggctctgcacaaccactacacgcagaagagcctctc
cctgtctccgggtaaatga

VL-CLKAPPA – DNA (SEQ ID NO:3)
GACATCCAGATGACACAGTCTCCAGCTTCCCTGTCTGCATCTCTGGGAGAAACTGT
CACCATCGAATGT<u>CGAACAAGTGAGGACATTTACAATGGTTTAGC</u>ATGGTATCAGC
AGAAGCCAGGGAAATCTCCTCAGCTCCTGGTCTAT<u>AGTGCAAATAGCTTACATATT</u>
GGGGTCCCATCACGGTTCAGTGGCAGTGGATCTGGTACACAGTATTCTCTCAAGA
TAAACAGCCTGCAATTTGAAGATGTCGCAAGTTATTTCTGT<u>CAACAGTATTACGATT</u>
<u>ATCCGCTCGCGTTCGGTTCTGGGACCAAGCTGGAGATCAAACGG</u>acggtggctgcaccat
ctgtcttcatcttcccgccatctgatgagcagttgaaatctggaactgcctctgttgtgtgcctgctgaataacttctatcccaga
gaggccaaagtacagtggaaggtggataacgccctccaatcgggtaactcccaggagagtgtcacagagcaggaca
gcaaggacagcacctacagcctcagcagcaccctgacgctgagcaaagcagactacgagaaacacaaagtctacgc
ctgcgaagtcacccatcagggcctgagctcgcccgtcacaaagagcttcaacaggggagagtgttag

VH-FcG1M (E333A) – Protein (SEQ ID NO:2)
AVQLVESGGGLVQPGGSLKLSCAVSG<u>FTLSDYYMA</u>WVRQAPKKGLEWVA<u>TISASGLRTYYPDSVKG</u>RFTISR
DDAKRSLFLQMTSLKSEDTATYYCAR<u>PMSAHYGFNYFDY</u>WGQGVMVTVSSastkgpsvfplapsskstsggtaalg
clvkdyfpepvtvswnsgaltsgvhtfpavlqssglyslssvvtvpsslgtqtyicnvnhkpsntkvdkkvepkscdkthtcppcpape
llggpsvflfppkpkdtlmisrtpevtcvvvdvshedpevkfnwyvdgvevhnaktkpreeqynstyrvvsvltvlhqdwlngkeykc
kvsnkalpapiaktiskakgqprepqvytlppsreemtknqvsltclvkgfypsdiavewesngqpennykttppvldsdgsfflyskl
tvdksrwqqgnvfscsvmhealhnhytqkslslspgk*

VL-CLKAPPA – Protein (SEQ ID NO:4)
DIQMTQSPASLSASLGETVTIEC<u>RTSEDIYNGLA</u>WYQQKPGKSPQLLVY<u>SANSLHI</u>GVPSRFSGSGSGTQYSLK
INSLQFEDVASYFC<u>QQYYDYPLAF</u>GSGTKLEIKRtvaapsvfifppsdeqlksgtasvvcllnnfypreakvqwkvdnalqsg
nsqesvteqdskdstyslsstltlskadyekhkvyacevthqglsspvtksfnrgec*

Figure 10

VH-FCG4M (S228P) – DNA (SEQ ID NO: 5)
GCGGTGCAGCTGGTGGAGTCTGGGGGAGGCCTAGTGCAGCCTGGAGGGTCCCTGAA
ACTCTCCTGTGCAGTCTCAGGA<u>TTCACTCTCAGTGACTATTACATGGCC</u>TGGGTCCGC
CAGGCTCCAAAGAAGGGTCTGGAATGGGTCGCA<u>ACCATTAGTGCCAGTGGGCTCAGA</u>
<u>ACTTACTATCCAGACTCCGTGAAGGGC</u>CGCTTCACTATCTCCAGAGATGATGCAAAA
GGAGCCTCTTCCTGCAAATGACCAGTCTGAAGTCTGAGGACACGGCCACTTATTACTG
TGCAAGA<u>CCGATGTCTGCACACTATGGTTTTAACTACTTTGATTAC</u>TGGGGCCAAGGA
GTCATGGTCACAGTCTCCTCAgctagcaccaagggcccatcggtcttccccctggcgccctgctccaggagca
cctccgagagcacagccgccctgggctgcctggtcaaggactacttccccgaaccggtgacggtgtcgtggaactcaggcgc
cctgaccagcggcgtgcacaccttcccggctgtcctacagtcctcaggactctactccctcagcagcgtggtgaccgtgccctcc
agcagcttgggcacgaagacctacacctgcaacgtagatcacaagcccagcaacaccaaggtggacaagagagttgagtc
caaatatggtcccccatgcccaccatgcccagcacctgagttcctggggggaccatcagtcttcctgttccccccaaaacccaa
ggacactctcatgatctcccggacccctgaggtcacgtgcgtggtggtggacgtgagccaggaagaccccgaggtccagttc
aactggtacgtggatggcgtggaggtgcataatgccaagacaaagccgcgggaggagcagttcaacagcacgtaccgtgtg
gtcagcgtcctcaccgtcctgcaccaggactggctgaacggcaaggagtacaagtgcaaggtctccaacaaaggcctcccgt
cctccatcgagaaaaccatctccaaagccaaagggcagccccgagagccacaggtgtacaccctgcccccatcccaggag
gagatgaccaagaaccaggtcagcctgacctgcctggtcaaaggcttctaccccagcgacatcgccgtggagtgggagagc
aatgggcagccggagaacaactacaagaccacgcctcccgtgctggactccgacggctccttcttcctctacagcaggctaa
ccgtggacaagagcaggtggcaggaggggaatgtcttctcatgctccgtgatgcatgaggctctgcacaaccactacacaca
gaagagcctctccctgtctccgggtaaatga
VL-CLKAPPA – DNA (SEQ ID NO: 7)
GACATCCAGATGACACAGTCTCCAGCTTCCCTGTCTGCATCTCTGGGAGAAACTGTCA
CCATCGAATGT<u>CGAACAAGTGAGGACATTTACAATGGTTTAGC</u>ATGGTATCAGCAGAA
GCCAGGGAAATCTCCTCAGCTCCTGGTCTAT<u>AGTGCAAATAGCTTACATATT</u>GGGGTC
CCATCACGGTTCAGTGGCAGTGGATCTGGTACACAGTATTCTCTCAAGATAAACAGCC
TGCAATTTGAAGATGTCGCAAGTTATTTCTGT<u>CAACAGTATTACGATTATCCGCTCGCG</u>
TTCGGTTCTGGGACCAAGCTGGAGATCAAACGgacggtggctgcaccatctgtcttcatcttcccgccatc
tgatgagcagttgaaatctggaactgcctctgttgtgtgcctgctgaataacttctatcccagagaggccaaagtacagtggaag
gtggataacgccctccaatcgggtaactcccaggagagtgtcacagagcaggacagcaaggacagcacctacagcctcag
cagcaccctgacgctgagcaaagcagactacgagaaacacaaagtctacgcctgcgaagtcacccatcagggcctgagct
cgcccgtcacaaagagcttcaacaggggagagtgttag
VH-FCG4M (S228P) – Protein (SEQ ID NO: 6)
AVQLVESGGGLVQPGGSLKLSCAVSG<u>FTLSDYYMA</u>WVRQAPKKGLEWVA<u>TISASGLRTYYPDSVKG</u>RFTISRDD
AKRSLFLQMTSLKSEDTATYYCAR<u>PMSAHYGFNYFDY</u>WGQGVMVTVSSastkgpsvfplapcsrstsestaalgclvkdyf
pepvtvswnsgaltsgvhtfpavlqssglyslssvvtvpssslgtktytcnvdhkpsntkvdkrveskygppcppcpapefIggpsvflfppk
pkdtlmisrtpevtcvvvdvsqedpevqfnwyvdgvevhnaktkpreeqfnstyrvvsvltvlhqdwlngkeykckvsnkglpssiektis
kakgqprepqvytlppsqeemtknqvsltclvkgfypsdiavewesngqpennykttppvldsdgsfflysrltvdksrwqegnvfscsv
mhealhnhytqkslslspgk*
VL-CLKAPPA – Protein (SEQ ID NO: 8)
DIQMTQSPASLSASLGETVTIEC<u>RTSEDIYNGLA</u>WYQQKPGKSPQLLVY<u>SANSLHI</u>GVPSR
FSGSGSGTQYSLKINSLQFEDVASYFC<u>QQYYDYPLA</u>FGSGTKLEIKRtvaapsvfifppsdeqlksg
tasvvcllnnfypreakvqwkvdnalqsgnsqesvteqdskdstyslsstltlskadyekhkvyacevthqglsspvtksfnrge
c*

Figure 11

Fc sequences

Human IgG1 (Uniprot P01857; SEQ ID NO: 31):
ASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

Human IgG2 (Uniprot P01859; SEQ ID NO: 32):
ASTKGPSVFPLAPCSRSTSESTAALGCLVKDYFPEPVTVSWNSGALTSGVHTFPAV
LQSSGLYSLSSVVTVPSSNFGTQTYTCNVDHKPSNTKVDKTVERKCCVECPPCPAP
PVAGPSVFLFPPKPKDTLMISRTPEVTCVVVDVSHEDPEVQFNWYVDGVEVHNA
KTKPREEQFNSTFRVVSVLTVVHQDWLNGKEYKCKVSNKGLPAPIEKTISKTKGQP
REPQVYTLPPSREEMTKNQVSLTCLVKGFYPSDISVEWESNGQPENNYKTTPPML
DSDGSFFLYSKLTVDKSRWQQGNVFSCSVMHEALHNHYTQKSLSLSPGK

Human IgG4 (Uniprot P01861; SEQ ID NO: 33):
ASTKGPSVFPLAPCSRSTSESTAALGCLVKDYFPEPVTVSWNSGALTSGVHTFPAV
LQSSGLYSLSSVVTVPSSSLGTKTYTCNVDHKPSNTKVDKRVESKYGPPCPSCPAPE
FLGGPSVFLFPPKPKDTLMISRTPEVTCVVVDVSQEDPEVQFNWYVDGVEVHNA
KTKPREEQFNSTYRVVSVLTVLHQDWLNGKEYKCKVSNKGLPSSIEKTISKAKGQP
REPQVYTLPPSQEEMTKNQVSLTCLVKGFYPSDIAVEWESNGQPENNYKTTPPVL
DSDGSFFLYSRLTVDKSRWQEGNVFSCSVMHEALHNHYTQKSLSLSLGK

Rat IgG1 (Uniprot P20759; SEQ ID NO: 34) used in N13B2
AETTAPSVYPLAPGTALKSNSMVTLGCLVKGYFPEPVTVTWNSGALSSGVHTFPA
VLQSGLYTLTSSVTVPSSTWPSQTVTCNVAHPASSTKVDKKIVPRNCGGDCKPCIC
TGSEVSSVFIFPPKPKDVLTITLTPKVTCVVVDISQDDPEVHFSWFVDDVEVHTAQ
TRPPEEQFNSTFRSVSELPILHQDWLNGRTFRCKVTSAAFPSPIEKTISKPEGRTQV
PHVYTMSPTKEEMTQNEVSITCMVKGFYPPDIYVEWQMNGQPQENYKNTPPT
MDTDGSYFLYSKLNVKKEKWQQGNTFTCSVLHEGLHNHHTEKSLSHSPGK

Figure 12

A.
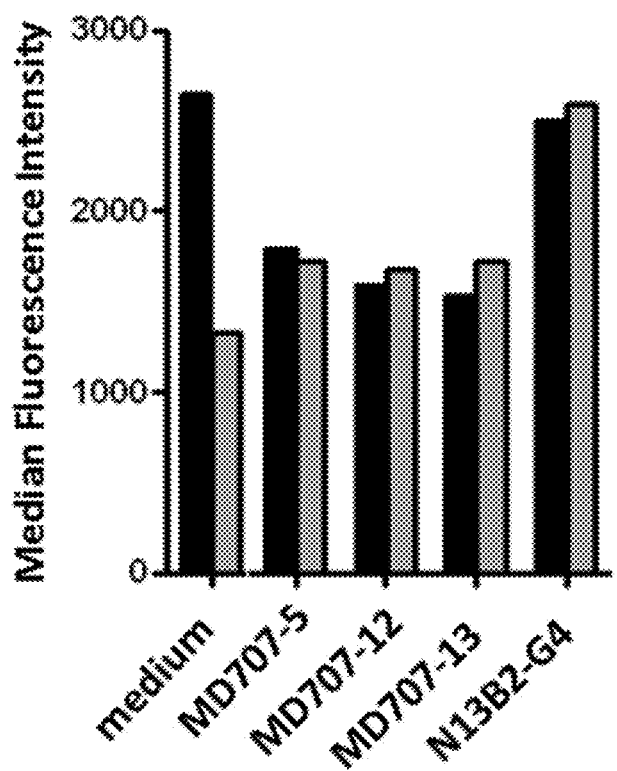
B.
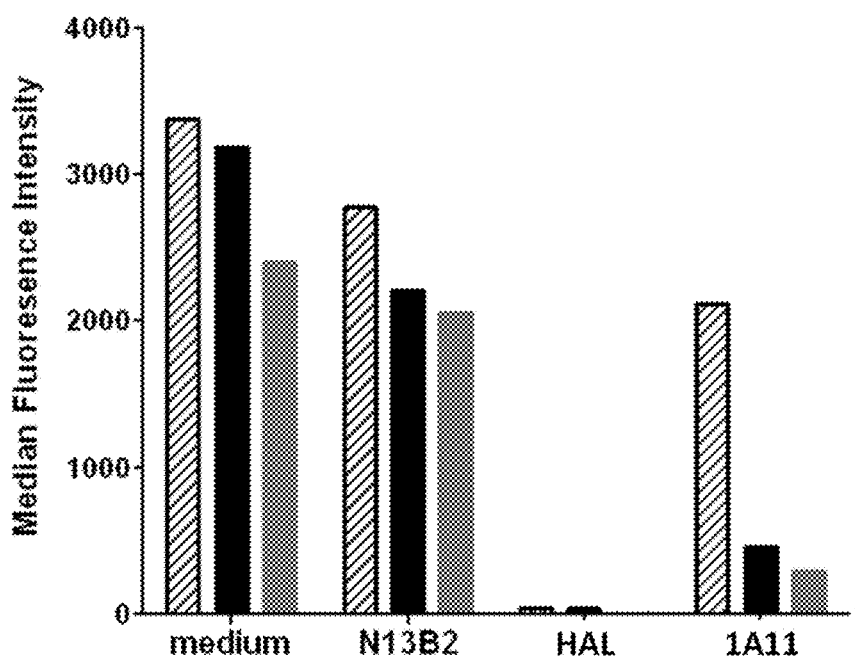
Figure 16

A.
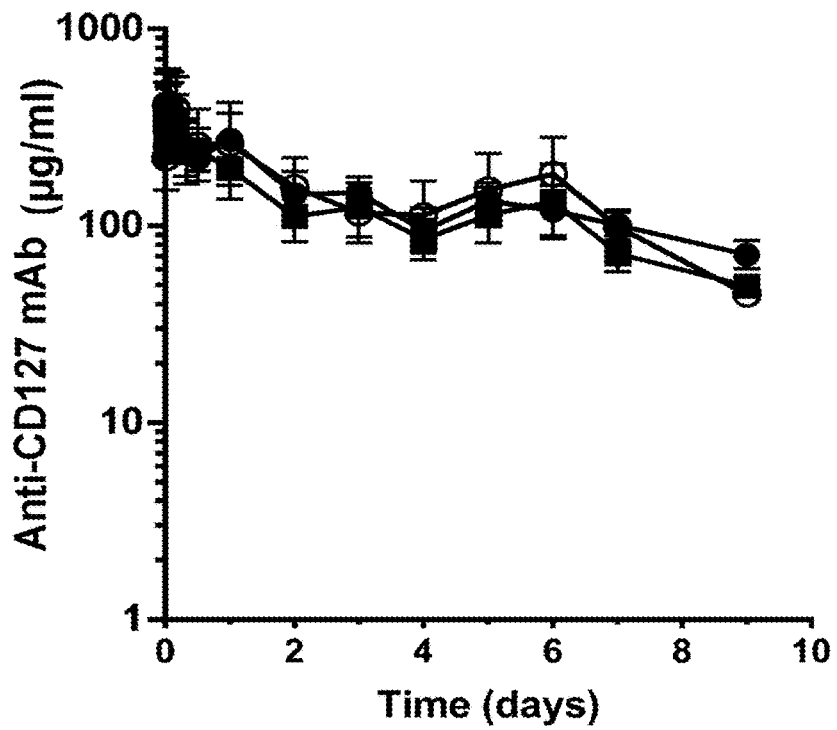
B.
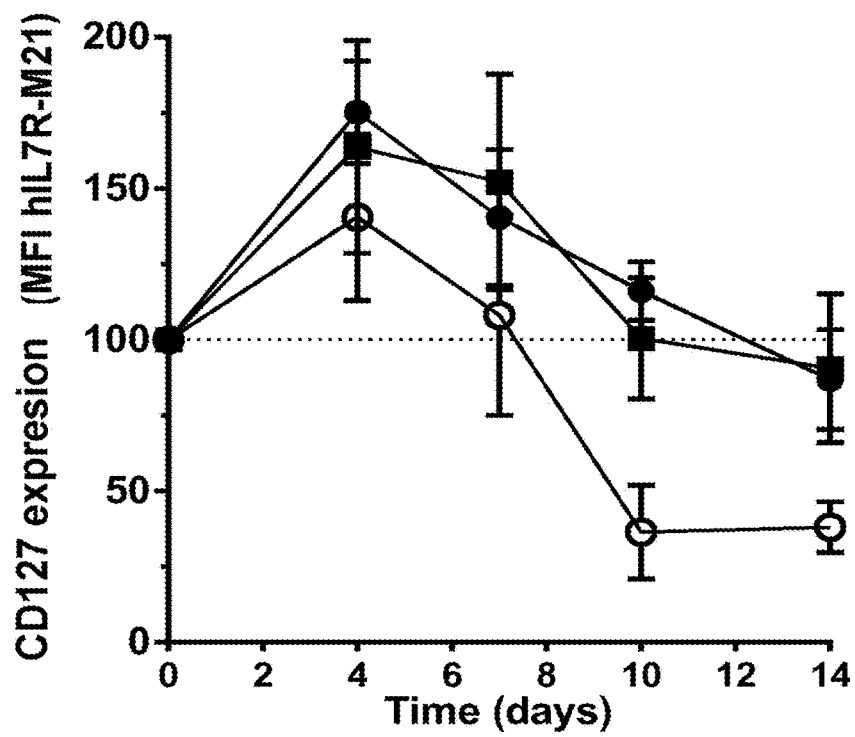
Figure 17

QVQLVESGGGLVKPGGSLRLSCAVSGFTLSDYYMAWIRQAPG
KGLEWVSTISASGLRTYYPDSVKGRFTISRDNAKNSLYLQMNS
LRAEDTAVYYCARPLSAHYGFNYFDYWGQGTLVTVSSASTKGP
SVFPLAPCSRSTSESTAALGCLVKDYFPEPVTVSWNSGALTSGV
HTFPAVLQSSGLYSLSSVVTVPSSSLGTKTYTCNVDHKPSNTKV
DKRVESKYGPPCPPCPAPEFLGGPSVFLFPPKPKDTLMISRTPE
VTCVVVDVSQEDPEVQFNWYVDGVEVHNAKTKPREEQFNST
YRVVSVLTVLHQDWLNGKEYKCKVSNKGLPSSIEKTISKAKGQ
PREPQVYTLPPSQEEMTKNQVSLTCLVKGFYPSDIAVEWESNG
QPENNYKTTPPVLDSDGSFFLYSRLTVDKSRWQEGNVFSCSV
MHEALHNHYTQKSLSLSPGK*

Figure 23

EIVMTQSPATLSVSPGERATLSCRTSEDIYQGLAWYQQKPGQA
PRLLIYSANTLHIGIPARFSGSGSGTEFTLTISSLQSEDFAVYYCQ
QYYDYPLAFGGGTKVEIKTVAAPSVFIFPPSDEQLKSGTASVVC
LLNNFYPREAKVQWKVDNALQSGNSQESVTEQDSKDSTYSLS
STLTLSKADYEKHKVYACEVTHQGLSSPVTKSFNRGEC*

Figure 24

~~MTILGTTFGMVFSLLQVVSG~~ESGYAQNGDLEDAELDDYSFS
CYSQLEVNGSQHSLTCAFEDPDVNTTNLEFEICGALVEVKC
LNFRKLQEIYFIETKKFLLIGKSNICVKVGEKSLTCKKIDL
TTIVKPEAPFDLSVIYREGANDFVVTFNTSHLQKKYVKVLM
HDVAYRQEKDENKWTHVNLSSTKLTLLQRKLQPAAMYEIKV
RSIPDHYFKGFWSEWSPSYYFRTPEINNSSGEMDPILLTIS
ILSFFSVALLVILACVLWKKRIKPIVWPSLPDHKKTLEHLC
KKPRKNLNVSFNPESFLDCQIHRVDDIQARDEVEGFLQDTF
PQQLEESEKQRLGGDVQSPNCPSEDVVITPESFGRDSSLTC
LAGNVSACDAPILSSSRSLDCRESGKNGPHVYQDLLLSLGT
TNSTLPPPFSLQSGILTLNPVAQGQPILTSLGSNQEEAYVT
MSSFYQNQ

Figure 27

SEQUENCE LISTING

```
Sequence total quantity: 132
SEQ ID NO: 1            moltype = DNA  length = 1359
FEATURE                 Location/Qualifiers
misc_feature            1..1359
                        note = Synthetic sequence
source                  1..1359
                        mol_type = other DNA
                        organism = synthetic construct
SEQUENCE: 1
gcggtgcagc tggtggagtc tggggggaggc ctagtgcagc ctggagggtc cctgaaactc    60
tcctgtgcag tctcaggatt cactctcagt gactattaca tggcctgggt ccgccaggct   120
ccaaagaagg gtctggaatg ggtcgcaacc attagtgcca gtgggctcag aacttactat   180
ccagactccg tgaagggccg cttcactatc tccagagatg atgcaaaaag gagcctcttc   240
ctgcaaatga ccagtctgaa gtctgaggac acggccactt attactgtgc aagaccgatg   300
tctgcacact atggttttaa ctactttgat tactggggcc aaggagtcat ggtcacagtc   360
tcctcagcta gcaccaaggg cccatcggtc ttccccctgg cacctcctc caagagcacc    420
tctgggggca cagcggccct gggctgcctg gtcaaggact acttccccga accggtgacg   480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacc   600
cagacctaca tctgcaacgt gaatcacaag cccagcaaca ccaaggtgga caagaaagtt   660
gagcccaaat cttgtgacaa aactcacaca tgcccaccgt gcccagcacc tgaactcctg   720
gggggaccgt cagtcttcct cttccccca aaacccaagg acaccctcat gatctcccgg    780
acccctgagg tcacatgcgt ggtggtggac gtgagccacg aagaccctga ggtcaagttc   840
aactggtacg tggacggcgt ggaggtgcat aatgccaaga caaagccgcg ggaggagcag   900
tacaacagca cgtaccgtgt ggtcagcgtc ctcaccgtcc tgcaccagga ctggctgaat   960
ggcaaggagt acaagtgcaa ggtctccaac aaagccctcc cagcccccat cgcgaaaacc  1020
atctccaaag ccaaagggca gccccgagaa ccacaggtgt acaccctgcc cccatcccgg  1080
gaggagatga ccaagaacca ggtcagcctg acctgcctg tcaaaggctt ctatcccagc   1140
gacatcgccg tggagtggga gagcaatggg cagccggaga caaactacaa gaccacgcct  1200
cccgtgctgg actccgacgg ctccttcttc ctctacagca agctcaccgt ggacaagagc  1260
aggtggcagc aggggaacgt cttctcatgc tccgtgatgc atgaggctct gcacaaccac  1320
tacacgcaga gagcctctc cctgtctccg ggtaaatga                          1359

SEQ ID NO: 2            moltype = AA  length = 452
FEATURE                 Location/Qualifiers
REGION                  1..452
                        note = Synthetic sequence
source                  1..452
                        mol_type = protein
                        organism = synthetic construct
SEQUENCE: 2
AVQLVESGGG LVQPGGSLKL SCAVSGFTLS DYYMAWVRQA PKKGLEWVAT ISASGLRTYY    60
PDSVKGRFTI SRDDAKRSLF LQMTSLKSED TATYYCARPM SAHYGFNYFD YWGQGVMVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIAKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 3            moltype = DNA  length = 645
FEATURE                 Location/Qualifiers
misc_feature            1..645
                        note = Synthetic sequence
source                  1..645
                        mol_type = other DNA
                        organism = synthetic construct
SEQUENCE: 3
gacatccaga tgacacagtc tccagcttcc ctgtctgcat ctctgggaga aactgtcacc    60
atcgaatgtc gaacaagtga ggacatttac aatggtttag catggtatca gcagaagcca   120
gggaaatctc ctcagctcct ggtctatagt gcaaatagct acatattggg gtcccatca    180
cggttcagtg gcagtggatc tggtacacag tattctctca agataaacag cctgcaattt   240
```

```
gaagatgtcg caagttattt ctgtcaacag tattacgatt atccgctcgc gttcggttct  300
gggaccaagc tggagatcaa acggacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg ataacgccc tccaatcggg taactcccag   480
gagagtgtca cagagcagga cagcaaggac agcacctaca gcctcagcag cacccttgacg  540
ctgagcaaaa cagactacga gaaacacaaa gtctacgcct gcgaagtcac ccatcagggc  600
ctgagctcgc ccgtcacaaa gagcttcaac aggggagagt gttag                  645

SEQ ID NO: 4              moltype = AA   length = 214
FEATURE                   Location/Qualifiers
REGION                    1..214
                          note = Synthetic sequence
source                    1..214
                          mol_type = protein
                          organism = synthetic construct
SEQUENCE: 4
DIQMTQSPAS LSASLGETVT IECRTSEDIY NGLAWYQQKP GKSPQLLVYS ANSLHIGVPS   60
RFSGSGSGTQ YSLKINSLQF EDVASYFCQQ YYDYPLAFGS GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 5              moltype = DNA   length = 1350
FEATURE                   Location/Qualifiers
misc_feature              1..1350
                          note = Synthetic sequence
source                    1..1350
                          mol_type = other DNA
                          organism = synthetic construct
SEQUENCE: 5
gcggtgcagc tggtggagtc tgggggaggc ctagtgcagc ctggagggtc cctgaaactc    60
tcctgtgcag tctcaggatt cactctcagt gactattaca tggcctgggt ccgccaggct  120
ccaaagaagg gtctggaatg ggtcgcaacc attagtgcca gtgggctcag aacttactat  180
ccagactccg tgaagggccg cttcactatc tccagagatg atgcaaaaag gagcctcttc  240
ctgcaaatga ccagtctgaa gtctgaggac acggccactt attactgtgc aagaccgatg  300
tctgcacact atggttttaa ctactttgat tactgggggc aaggagtcat ggtcacagtg  360
tcctcagcta gcaccaaggg cccatcggtc ttccccctgg cgccctgctc caggagcacc  420
tccgagagca cagccgccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggtccccc atgcccacca tgcccagcac ctgagttcct ggggggacca  720
tcagtcttcc tgttcccccc aaaacccaag gacactctca tgatctcccg gacccctgag  780
gtcacgtgcg tggtggtgga cgtgagccag gaagacccg aggtccagtt caactggtac   840
gtggatggcg tggaggtgca taatgccaag acaaagccgc gggaggagca gttcaacagc  900
acgtaccgtg tggtcagcgt cctcaccgtc ctgcaccagg actggctgaa cggcaaggag  960
tacaagtgca aggtctccaa caaaggcctc ccgtcctcca tcgagaaaac catctccaaa 1020
gccaaagggc agccccgaga gccacaggtg tacaccctgc ccccatccca ggaggagatg 1080
accaagaacc aggtcagcct gacctgcctg gtcaaaggct tctacccag cgacatcgcc  1140
gtggagtggg agagcaatgg gcagccggag aacaactaca agaccacgcc tcccgtgctg 1200
gactccgacg gctccttctt cctctacagc aggctaaccg tggacaagag caggtggcag 1260
gaggggaatg tcttctcatg ctccgtgatg catgaggctc tgcacaacca ctacacacag 1320
aagagcctct ccctgtctcc gggtaaatga                                  1350

SEQ ID NO: 6              moltype = AA   length = 449
FEATURE                   Location/Qualifiers
REGION                    1..449
                          note = Synthetic sequence
source                    1..449
                          mol_type = protein
                          organism = synthetic construct
SEQUENCE: 6
AVQLVESGGG LVQPGGSLKL SCAVSGFTLS DYYMAWVRQA PKKGLEWVAT ISASGLRTYY   60
PDSVKGRFTI SRDDAKRSLF LQMTSLKSED TATYYCARPM SAHYGFNYFD YWGQGVMVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSPGK                                    449

SEQ ID NO: 7              moltype = DNA   length = 645
FEATURE                   Location/Qualifiers
misc_feature              1..645
                          note = Synthetic sequence
source                    1..645
                          mol_type = other DNA
                          organism = synthetic construct
SEQUENCE: 7
gacatccaga tgacacagtc tccagcttcc ctgtctgcat ctctgggaga aactgtcacc    60
```

```
atcgaatgtc gaacaagtga ggacatttac aatggtttag catggtatca gcagaagcca    120
gggaaatctc ctcagctcct ggtctatagt gcaaatagct tacatattgg ggtcccatca    180
cggttcagtg gcagtggatc tggtacacag tattctctca agataaacag cctgcaattt    240
gaagatgtcg caagttattt ctgtcaacag tattacgatt atccgctcgc gttcggttct    300
gggaccaagc tggagatcaa acggacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645

SEQ ID NO: 8                moltype = AA  length = 214
FEATURE                     Location/Qualifiers
REGION                      1..214
                            note = Synthetic sequence
source                      1..214
                            mol_type = protein
                            organism = synthetic construct
SEQUENCE: 8
DIQMTQSPAS LSASLGETVT IECRTSEDIY NGLAWYQQKP GKSPQLLVYS ANSLHIGVPS     60
RFSGSGSGTQ YSLKINSLQF EDVASYFCQQ YYDYPLAFGS GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 9                moltype = DNA  length = 27
FEATURE                     Location/Qualifiers
misc_feature                1..27
                            note = Synthetic sequence
source                      1..27
                            mol_type = other DNA
                            organism = synthetic construct
SEQUENCE: 9
ttcactctca gtgactatta catggcc                                         27

SEQ ID NO: 10               moltype = AA  length = 9
FEATURE                     Location/Qualifiers
REGION                      1..9
                            note = Synthetic sequence
source                      1..9
                            mol_type = protein
                            organism = synthetic construct
SEQUENCE: 10
FTLSDYYMA                                                             9

SEQ ID NO: 11               moltype = DNA  length = 51
FEATURE                     Location/Qualifiers
misc_feature                1..51
                            note = Synthetic sequence
source                      1..51
                            mol_type = other DNA
                            organism = synthetic construct
SEQUENCE: 11
accattagtg ccagtgggct cagaacttac tatccagact ccgtgaaggg c              51

SEQ ID NO: 12               moltype = AA  length = 17
FEATURE                     Location/Qualifiers
REGION                      1..17
                            note = Synthetic sequence
source                      1..17
                            mol_type = protein
                            organism = synthetic construct
SEQUENCE: 12
TISASGLRTY YPDSVKG                                                    17

SEQ ID NO: 13               moltype = DNA  length = 39
FEATURE                     Location/Qualifiers
misc_feature                1..39
                            note = Synthetic sequence
source                      1..39
                            mol_type = other DNA
                            organism = synthetic construct
SEQUENCE: 13
ccgatgtctg cacactatgg ttttaactac tttgattac                            39

SEQ ID NO: 14               moltype = AA  length = 13
FEATURE                     Location/Qualifiers
REGION                      1..13
                            note = Synthetic sequence
source                      1..13
```

```
                        mol_type = protein
                        organism = synthetic construct
SEQUENCE: 14
PMSAHYGFNY FDY                                                        13

SEQ ID NO: 15           moltype = DNA  length = 33
FEATURE                 Location/Qualifiers
misc_feature            1..33
                        note = Synthetic sequence
source                  1..33
                        mol_type = other DNA
                        organism = synthetic construct
SEQUENCE: 15
cgaacaagtg aggacattta caatggttta gca                                  33

SEQ ID NO: 16           moltype = AA  length = 11
FEATURE                 Location/Qualifiers
REGION                  1..11
                        note = Synthetic sequence
source                  1..11
                        mol_type = protein
                        organism = synthetic construct
SEQUENCE: 16
RTSEDIYNGL A                                                          11

SEQ ID NO: 17           moltype = DNA  length = 21
FEATURE                 Location/Qualifiers
misc_feature            1..21
                        note = Synthetic sequence
source                  1..21
                        mol_type = other DNA
                        organism = synthetic construct
SEQUENCE: 17
agtgcaaata gcttacatat t                                               21

SEQ ID NO: 18           moltype = AA  length = 7
FEATURE                 Location/Qualifiers
REGION                  1..7
                        note = Synthetic sequence
source                  1..7
                        mol_type = protein
                        organism = synthetic construct
SEQUENCE: 18
SANSLHI                                                               7

SEQ ID NO: 19           moltype = DNA  length = 27
FEATURE                 Location/Qualifiers
misc_feature            1..27
                        note = Synthetic sequence
source                  1..27
                        mol_type = other DNA
                        organism = synthetic construct
SEQUENCE: 19
caacagtatt acgattatcc gctcgcg                                         27

SEQ ID NO: 20           moltype = AA  length = 9
FEATURE                 Location/Qualifiers
REGION                  1..9
                        note = Synthetic sequence
source                  1..9
                        mol_type = protein
                        organism = synthetic construct
SEQUENCE: 20
QQYYDYPLA                                                             9

SEQ ID NO: 21           moltype = DNA  length = 366
FEATURE                 Location/Qualifiers
misc_feature            1..366
                        note = Synthetic sequence
source                  1..366
                        mol_type = other DNA
                        organism = synthetic construct
SEQUENCE: 21
gcggtgcagc tggtggagtc tgggggaggc ctagtgcagc ctggagggtc cctgaaactc      60
tcctgtgcag tctcaggatt cactctcagt gactattaca tggcctgggt ccgccaggct     120
ccaaagaagg gtctggaatg ggtcgcaacc attagtgcca gtgggctcag aacttactat     180
ccagactccg tgaagggccg cttcactatc tccagagatg atgcaaaaag gagcctcttc     240
ctgcaaatga ccagtctgaa gtctgaggac acggccactt attactgtgc aagaccgatg     300
tctgcacact atggttttaa ctactttgat tactggggcc aaggagtcat ggtcacagtc     360
```

```
tcctca                                                                      366

SEQ ID NO: 22           moltype = AA   length = 122
FEATURE                 Location/Qualifiers
REGION                  1..122
                        note = Synthetic sequence
source                  1..122
                        mol_type = protein
                        organism = synthetic construct
SEQUENCE: 22
AVQLVESGGG LVQPGGSLKL SCAVSGFTLS DYYMAWVRQA PKKGLEWVAT ISASGLRTYY           60
PDSVKGRFTI SRDDAKRSLF LQMTSLKSED TATYYCARPM SAHYGFNYFD YWGQGVMVTV          120
SS                                                                        122

SEQ ID NO: 23           moltype = DNA   length = 324
FEATURE                 Location/Qualifiers
misc_feature            1..324
                        note = Synthetic sequence
source                  1..324
                        mol_type = other DNA
                        organism = synthetic construct
SEQUENCE: 23
gacatccaga tgacacagtc tccagcttcc ctgtctgcat ctctgggaga aactgtcacc           60
atcgaatgtc gaacaagtga ggacatttac aatggtttag catggtatca gcagaagcca         120
gggaaatctc ctcagctcct ggtctatagt gcaaatagct acatattggg gtcccatca          180
cggttcagtg gcagtggatc tggtacacag tattctctca agataaacag cctgcaattt         240
gaagatgtcg caagttattt ctgtcaacag tattacgatt atccgctcgc gttcggttct         300
gggaccaagc tggagatcaa acgg                                                324

SEQ ID NO: 24           moltype = AA   length = 108
FEATURE                 Location/Qualifiers
REGION                  1..108
                        note = Synthetic sequence
source                  1..108
                        mol_type = protein
                        organism = synthetic construct
SEQUENCE: 24
DIQMTQSPAS LSASLGETVT IECRTSEDIY NGLAWYQQKP GKSPQLLVYS ANSLHIGVPS           60
RFSGSGSGTQ YSLKINSLQF EDVASYFCQQ YYDYPLAFGS GTKLEIKR                      108

SEQ ID NO: 25           moltype = DNA   length = 993
FEATURE                 Location/Qualifiers
misc_feature            1..993
                        note = Synthetic sequence
source                  1..993
                        mol_type = other DNA
                        organism = synthetic construct
SEQUENCE: 25
gctagcacca agggcccatc ggtcttcccc ctggcaccct cctccaagag cacctctggg           60
ggcacagcgg ccctgggctg cctggtcaag gactacttcc ccgaaccggt gacggtgtcg         120
tggaactcag gcgccctgac cagcggcgtg cacaccttcc cggctgtcct acagtcctca         180
ggactctact ccctcagcag cgtggtgacc gtgccctcca gcagcttggg cacccagacc         240
tacatctgca acgtgaatca caagcccagc aacaccaagg tggacaagaa agttgagccc         300
aaatcttgtg acaaaactca cacatgccca ccgtgcccag cacctgaact cctgggggga         360
ccgtcagtct tcctcttccc cccaaaaccc aaggacaccc tcatgatctc ccggacccct         420
gaggtcacat gcgtggtggt ggacgtgagc cacgaagacc ctgaggtcaa gttcaactgg         480
tacgtggacg gcgtggaggt gcataatgcc aagacaaagc cgcgggagga gcagtacaac         540
agcacgtacc gtgtggtcag cgtcctcacc gtcctgcacc aggactggct gaatggcaag         600
gagtacaagt gcaaggtctc caacaaagcc ctcccagccc ccatcgcgcg aaaccatctc         660
aaagccaaag ggcagccccg agaaccacag gtgtacaccc tgcccccatc ccggagggag         720
atgaccaaga accaggtcag cctgacctgc ctggtcaaag gcttctatcc cagcgacatc         780
gccgtggagt gggagagcaa tgggcagccg gagaacaact acaagaccac gcctcccgtg         840
ctggactccg acggctcctt cttcctctac agcaagctca ccgtggacaa gagcaggtgg         900
cagcagggga acgtcttctc atgctccgtg atgcatgagg ctctgcacaa ccactacacg         960
cagaagagcc tctccctgtc tccgggtaaa tga                                      993

SEQ ID NO: 26           moltype = AA   length = 330
FEATURE                 Location/Qualifiers
REGION                  1..330
                        note = Synthetic sequence
source                  1..330
                        mol_type = protein
                        organism = synthetic construct
SEQUENCE: 26
ASTKGPSVFP LAPSSKSTSG GTAALGCLVK DYFPEPVTVS WNSGALTSGV HTFPAVLQSS           60
GLYSLSSVVT VPSSSLGTQT YICNVNHKPS NTKVDKKVEP KSCDKTHTCP PCPAPELLGG         120
PSVFLFPPKP KDTLMISRTP EVTCVVVDVS HEDPEVKFNW YVDGVEVHNA KTKPREEQYN         180
STYRVVSVLT VLHQDWLNGK EYKCKVSNKA LPAPIAKTIS KAKGQPREPQ VYTLPPSREE         240
MTKNQVSLTC LVKGFYPSDI AVEWESNGQP ENNYKTTPPV LDSDGSFFLY SKLTVDKSRW         300
```

QQGNVFSCSV MHEALHNHYT QKSLSLSPGK                             330

SEQ ID NO: 27           moltype = DNA   length = 984
FEATURE                 Location/Qualifiers
misc_feature            1..984
                        note = Synthetic sequence
source                  1..984
                        mol_type = other DNA
                        organism = synthetic construct
SEQUENCE: 27
gctagcacca agggcccatc ggtcttcccc ctggcgccct gctccaggag cacctccgag    60
agcacagccg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacgaagacc   240
tacacctgca acgtagatca caagcccagc aacaccaagg tggacaagag agttgagtcc   300
aaatatggtc cccatgccc accatgccca gcacctgagt tcctgggggg accatcagtc   360
ttcctgttcc ccccaaaacc caaggacact ctcatgatct cccggacccc tgaggtcacg   420
tgcgtggtgg tggacgtgag ccaggaagac cccgaggtcc agttcaactg gtacgtggat   480
ggcgtggagg tgcataatgc caagacaaag ccgcgggagg agcagttcaa cagcacgtac   540
cgtgtggtca gcgtcctcac cgtcctgcac caggactggc tgaacggcaa ggagtacaag   600
tgcaaggtct ccaacaaagg cctcccgtcc tccatcgaga aaaccatctc caaagccaaa   660
gggcagcccc gagagccaca ggtgtacacc ctgcccccat cccaggagga gatgaccaag   720
aaccaggtca gcctgacctg cctggtcaaa ggcttctacc ccagcgacat cgccgtggaa   780
tgggagagca atgggcagcc ggagaacaac tacaagacca cgcctcccgt gctggactcc   840
gacggctcct tcttcctcta cagcaggcta accgtggaca agagcaggtg gcaggagggg   900
aatgtcttct catgctccgt gatgcatgag gctctgcaca accactacac acagaagagc   960
ctctccctgt ctccgggtaa atga                                         984

SEQ ID NO: 28           moltype = AA   length = 327
FEATURE                 Location/Qualifiers
REGION                  1..327
                        note = Synthetic sequence
source                  1..327
                        mol_type = protein
                        organism = synthetic construct
SEQUENCE: 28
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSPGK                                      327

SEQ ID NO: 29           moltype = DNA   length = 321
FEATURE                 Location/Qualifiers
misc_feature            1..321
                        note = Synthetic sequence
source                  1..321
                        mol_type = other DNA
                        organism = synthetic construct
SEQUENCE: 29
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                            321

SEQ ID NO: 30           moltype = AA   length = 106
FEATURE                 Location/Qualifiers
REGION                  1..106
                        note = Synthetic sequence
source                  1..106
                        mol_type = protein
                        organism = synthetic construct
SEQUENCE: 30
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                 106

SEQ ID NO: 31           moltype = AA   length = 330
FEATURE                 Location/Qualifiers
REGION                  1..330
                        note = Synthetic sequence
source                  1..330
                        mol_type = protein
                        organism = synthetic construct
SEQUENCE: 31
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120

```
PSVFLPPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                    330

SEQ ID NO: 32              moltype = AA   length = 326
FEATURE                    Location/Qualifiers
REGION                     1..326
                           note = Synthetic sequence
source                     1..326
                           mol_type = protein
                           organism = synthetic construct
SEQUENCE: 32
ASTKGPSVFP LAPCSRSTSE STAALGCLVK DYFPEPVTVS WNSGALTSGV HTFPAVLQSS     60
GLYSLSSVVT VPSSNFGTQT YTCNVDHKPS NTKVDKTVER KCCVECPPCP APPVAGPSVF    120
LFPPKPKDTL MISRTPEVTC VVVDVSHEDP EVQFNWYVDG VEVHNAKTKP REEQFNSTFR    180
VVSVLTVVHQ DWLNGKEYKC KVSNKGLPAP IEKTISKTKG QPREPQVYTL PPSREEMTKN    240
QVSLTCLVKG FYPSDISVEW ESNGQPENNY KTTPPMLDSD GSFFLYSKLT VDKSRWQQGN    300
VFSCSVMHEA LHNHYTQKSL SLSPGK                                        326

SEQ ID NO: 33              moltype = AA   length = 327
FEATURE                    Location/Qualifiers
REGION                     1..327
                           note = Synthetic sequence
source                     1..327
                           mol_type = protein
                           organism = synthetic construct
SEQUENCE: 33
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPSCP APEFLGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLGK                                       327

SEQ ID NO: 34              moltype = AA   length = 326
FEATURE                    Location/Qualifiers
REGION                     1..326
                           note = Synthetic sequence
source                     1..326
                           mol_type = protein
                           organism = synthetic construct
SEQUENCE: 34
AETTAPSVYP LAPGTALKSN SMVTLGCLVK GYFPEPVTVT WNSGALSSGV HTFPAVLQSG     60
LYTLTSSVTV PSSTWPSQTV TCNVAHPASS TKVDKKIVPR NCGGDCKPCI CTGSEVSSVF    120
IFPPKPKDVL TITLTPKVTC VVVDISQDDP EVHFSWFVDD VEVHTAQTRP PEEQFNSTFR    180
SVSELPILHQ DWLNGRTFRC KVTSAAFPSP IEKTISKPEG RTQVPHVYTM SPTKEEMTQN    240
EVSITCMVKG FYPPDIYVEW QMNGQPENY KNTPPTMDTD GSYFLYSKLN VKKEKWQQGN    300
TFTCSVLHEG LHNHHTEKSL SHSPGK                                        326

SEQ ID NO: 35              moltype = DNA   length = 366
FEATURE                    Location/Qualifiers
misc_feature               1..366
                           note = Synthetic sequence
source                     1..366
                           mol_type = other DNA
                           organism = synthetic construct
SEQUENCE: 35
caggtgcagc tggtcgaatc tggagggggt ctggtcaagc ccggagggtc actgcgtctg     60
tcatgcgccg tctcagggtt cacactgtct gactactata tggcttgggt gcgacaggca    120
ccaggcaagg gactgagtg ggtcgccact atctctgcta gtggcctgag gacctactat    180
cctgatagtg tgaagggaag gttcacaatt tcacggacg atgcaaaaaa ctccctgtac    240
ctgcagatga atagcctgag agcagaagac accgccgtct actattgcgc cgcccaatg    300
agcgctcact atggcttcaa ctactttgat tattgggggc agggtaccct ggtgacagtc    360
tccagc                                                              366

SEQ ID NO: 36              moltype = AA   length = 122
FEATURE                    Location/Qualifiers
REGION                     1..122
                           note = Synthetic sequence
source                     1..122
                           mol_type = protein
                           organism = synthetic construct
SEQUENCE: 36
QVQLVESGGG LVKPGGSLRL SCAVSGFTLS DYYMAWVRQA PGKGLEWVAT ISASGLRTYY     60
PDSVKGRFTI SRDDAKNSLY LQMNSLRAED TAVYYCARPM SAHYGFNYFD YWGQGTLVTV    120
SS                                                                   122

SEQ ID NO: 37              moltype = DNA   length = 366
```

```
FEATURE                 Location/Qualifiers
misc_feature            1..366
                        note = Synthetic sequence
source                  1..366
                        mol_type = other DNA
                        organism = synthetic construct
SEQUENCE: 37
caggtgcagc tggtcgaatc tgggggggga ctggtcaaac ccggaggctc actgcgtctg    60
tcatgtgccg tctcaggctt tacactgagc gactactata tggcatggat ccgacaggca   120
ccaggcaagg gactggagtg ggtgtctact atttctgcca gtggcctgag gacctactat   180
cctgacagtg tcaagggaag gttcacaatc tcacgggata cgctaaaaa ttccctgtac    240
ctgcagatga acagcctgag agccgaagac accgctgtgt actattgcgc tcgcccaatg   300
tccgcacact atggcttcaa ttactttgat tattgggggc agggtaccct ggtgacagtc   360
tccagc                                                              366

SEQ ID NO: 38           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 38
QVQLVESGGG LVKPGGSLRL SCAVSGFTLS DYYMAWIRQA PGKGLEWVST ISASGLRTYY    60
PDSVKGRFTI SRDNAKNSLY LQMNSLRAED TAVYYCARPM SAHYGFNYFD YWGQGTLVTV   120
SS                                                                  122

SEQ ID NO: 39           moltype = DNA  length = 366
FEATURE                 Location/Qualifiers
misc_feature            1..366
                        note = Synthetic sequence
source                  1..366
                        mol_type = other DNA
                        organism = synthetic construct
SEQUENCE: 39
caggtgcagc tggtcgaatc aggggggga ctggtcaaac ccggggggctc actgcgtctg    60
tcatgtgccg tctcaggctt cacactgagc gactactata tggcatggat ccgacaggca   120
ccaggcaagg gactggagtg ggtgtctact atttctgcca gtggcctgag gacctactat   180
cctgacagtg tcaagggaag gttcacaatc tcacgggata cgctaaaaa ttccctgtac    240
ctgcagatga acagcctgag agccgaagac accgctgtgt actattgcgc tcgcccactg   300
tccgcacact atggcttcaa ttactttgat tattgggggc agggtaccct ggtgacagtc   360
tccagc                                                              366

SEQ ID NO: 40           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 40
QVQLVESGGG LVKPGGSLRL SCAVSGFTLS DYYMAWIRQA PGKGLEWVST ISASGLRTYY    60
PDSVKGRFTI SRDNAKNSLY LQMNSLRAED TAVYYCARPL SAHYGFNYFD YWGQGTLVTV   120
SS                                                                  122

SEQ ID NO: 41           moltype = DNA  length = 321
FEATURE                 Location/Qualifiers
misc_feature            1..321
                        note = Synthetic sequence
source                  1..321
                        mol_type = other DNA
                        organism = synthetic construct
SEQUENCE: 41
gaaattgtga tgactcagtc tcccgctacc ctgtcagtct ctcccggcga acgtgctacc    60
ctgtcctgcc gaacctcaga agatatctac aacgggctgg cttggtatca gcagaagccc   120
ggacaggccc ctaggctgct ggtgtactcc gctaattctc tgcacatcgg cattccagca   180
cggttctctg gtagtggctc aggaactgag tataccctga caatctccag cctgcagagc   240
gaaagacttcg cagtgtactt ttgccagcag tactatgatt atccccctggc ctttggcgga   300
gggaccaagg tcgagatcaa g                                              321

SEQ ID NO: 42           moltype = AA  length = 107
FEATURE                 Location/Qualifiers
REGION                  1..107
                        note = Synthetic sequence
source                  1..107
                        mol_type = protein
                        organism = synthetic construct
SEQUENCE: 42
EIVMTQSPAT LSVSPGERAT LSCRTSEDIY NGLAWYQQKP GQAPRLLVYS ANSLHIGIPA    60
```

```
RFSGSGSGTE YTLTISSLQS EDFAVYFCQQ YDYDYPLAFGG GTKVEIK                    107

SEQ ID NO: 43               moltype = DNA   length = 321
FEATURE                     Location/Qualifiers
misc_feature                1..321
                            note = Synthetic sequence
source                      1..321
                            mol_type = other DNA
                            organism = synthetic construct
SEQUENCE: 43
gaaatcgtga tgactcagtc tcctgctact ctgtccgtgt ccctggtga acgtgctact        60
ctgtcctgtc gtacctccga agatatttac aacgggctgg cttggtatca gcagaagccc     120
ggacaggccc ctaggctgct gatctactcc gctaattctc tgcacatcgg cattccagca     180
cggttctctg gtagtggctc aggaactgag tttacccctga caatttccag cctgcagagc    240
gaagacttcg cagtgtacta ttgccagcag tactatgatt atccccctggc ctttggcgga    300
gggaccaagg tcgagatcaa a                                                321

SEQ ID NO: 44               moltype = AA   length = 107
FEATURE                     Location/Qualifiers
REGION                      1..107
                            note = Synthetic sequence
source                      1..107
                            mol_type = protein
                            organism = synthetic construct
SEQUENCE: 44
EIVMTQSPAT LSVSPGERAT LSCRTSEDIY NGLAWYQQKP GQAPRLLIYS ANSLHIGIPA       60
RFSGSGSGTE FTLTISSLQS EDFAVYYCQQ YDYDYPLAFGG GTKVEIK                   107

SEQ ID NO: 45               moltype = DNA   length = 321
FEATURE                     Location/Qualifiers
misc_feature                1..321
                            note = Synthetic sequence
source                      1..321
                            mol_type = other DNA
                            organism = synthetic construct
SEQUENCE: 45
gaaattgtga tgactcagag ccctgctaca ctgtccgtca gccctggaga acgtgctaca       60
ctgtcctgtc gcacctcaga agatatttac caggggctgg cttggtatca gcagaagccc     120
ggacaggccc ctaggctgct gatctactcc gctaacactc tgcacatcgg cattccagca     180
cggttctctg gtagtggctc aggaaccgag tttacccctga caatttccag cctgcagtct    240
gaagacttcg cagtgtacta ttgccagcag tactatgatt atccccctggc ctttggcgga    300
gggacaaagg tcgagatcaa a                                                321

SEQ ID NO: 46               moltype = AA   length = 107
FEATURE                     Location/Qualifiers
REGION                      1..107
                            note = Synthetic sequence
source                      1..107
                            mol_type = protein
                            organism = synthetic construct
SEQUENCE: 46
EIVMTQSPAT LSVSPGERAT LSCRTSEDIY QGLAWYQQKP GQAPRLLIYS ANTLHIGIPA       60
RFSGSGSGTE FTLTISSLQS EDFAVYYCQQ YDYDYPLAFGG GTKVEIK                   107

SEQ ID NO: 47               moltype = DNA   length = 39
FEATURE                     Location/Qualifiers
misc_feature                1..39
                            note = Synthetic sequence
source                      1..39
                            mol_type = other DNA
                            organism = synthetic construct
SEQUENCE: 47
ccactgtccg cacactatgg cttcaattac tttgattat                              39

SEQ ID NO: 48               moltype = AA   length = 13
FEATURE                     Location/Qualifiers
REGION                      1..13
                            note = Synthetic sequence
source                      1..13
                            mol_type = protein
                            organism = synthetic construct
SEQUENCE: 48
PLSAHYGFNY FDY                                                          13

SEQ ID NO: 49               moltype = DNA   length = 36
FEATURE                     Location/Qualifiers
misc_feature                1..36
                            note = Synthetic sequence
source                      1..36
```

```
                        mol_type = other DNA
                        organism = synthetic construct
SEQUENCE: 49
tgtcgcacct cagaagatat ttaccagggg ctggct                              36

SEQ ID NO: 50           moltype = AA   length = 12
FEATURE                 Location/Qualifiers
REGION                  1..12
                        note = Synthetic sequence
source                  1..12
                        mol_type = protein
                        organism = synthetic construct
SEQUENCE: 50
CRTSEDIYQG LA                                                        12

SEQ ID NO: 51           moltype = DNA   length = 21
FEATURE                 Location/Qualifiers
misc_feature            1..21
                        note = Synthetic sequence
source                  1..21
                        mol_type = other DNA
                        organism = synthetic construct
SEQUENCE: 51
tccgctaaca ctctgcacat c                                              21

SEQ ID NO: 52           moltype = AA   length = 7
FEATURE                 Location/Qualifiers
REGION                  1..7
                        note = Synthetic sequence
source                  1..7
                        mol_type = protein
                        organism = synthetic construct
SEQUENCE: 52
SANTLHI                                                              7

SEQ ID NO: 53           moltype = DNA   length = 1350
FEATURE                 Location/Qualifiers
misc_feature            1..1350
                        note = Synthetic sequence
source                  1..1350
                        mol_type = other DNA
                        organism = synthetic construct
SEQUENCE: 53
caggtgcagc tggtcgaatc aggggggga ctggtcaaac ccggggctc actgcgtctg      60
tcatgtgccg tctcaggctt cacactgagc gactactata tggcatggat ccgacaggca   120
ccaggcaagg gactggagtg ggtgtctact atttctgcca gtggcctgag gacctactat   180
cctgacagtg tcaagggaag gttcacaatc tcacgggata acgctaaaaa ttcccctgtac 240
ctgcagatga acagcctgag agccgaagac accgctgtgt actattgcgc tcgcccactg   300
tccgcacact atggcttcaa ttactttgat tattggggc agggtaccct ggtgacagtc    360
tccagcgcta gcaccaaggg cccatcggtc ttcccctgg cgccctgctc caggagcacc    420
tccgagagca cagccgcct gggctgcctg gtcaaggact acttcccga accggtgacg     480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacg   600
aagacctaca cctgcaacgt agatcacaag cccagcaaca ccaaggtgga caagagagtt   660
gagtccaaat atggtccccc atgcccacca tgcccagctg ctgagttcct gggggaccca   720
tcagtcttcc tgttccccc aaaacccaag gacactctca tgatctcccg gacccctgag   780
gtcacgtgcg tggtggtgga cgtgagccag gaagacccg aggtccagtt caactggtac    840
gtggatggcg tggaggtgca taatgccaag acaaagccgc gggaggagca gttcaacagc   900
acgtaccgtg tggtcagcgt cctcaccgtc ctgcaccagg actggctgaa cggcaaggag   960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctacccag cgacatcgcc   1140
gtggagtggg agagcaatgg gcagccggag aacaactaca agaccacgcc tcccgtgctg  1200
gactccgacg gctccttctt cctctacagc aggctaaccg tggacaagag caggtggcag  1260
gaggggaatg tcttctcatg ctccgtgatg catgaggctc tgcacaacca ctacacacag  1320
aagagcctct ccctgtctcc gggtaaatga                                   1350

SEQ ID NO: 54           moltype = AA   length = 449
FEATURE                 Location/Qualifiers
REGION                  1..449
                        note = Synthetic sequence
source                  1..449
                        mol_type = protein
                        organism = synthetic construct
SEQUENCE: 54
QVQLVESGGG LVKPGGSLRL SCAVSGFTLS DYYMAWIRQA PGKGLEWVST ISASGLRTYY    60
PDSVKGRFTI SRDNAKNSLY LQMNSLRAED TAVYYCARPL SAHYGFNYFD YWGQGTLVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFLGGP   240
```

```
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSPGK                                     449

SEQ ID NO: 55              moltype = DNA  length = 642
FEATURE                    Location/Qualifiers
misc_feature               1..642
                           note = Synthetic sequence
source                     1..642
                           mol_type = other DNA
                           organism = synthetic construct
SEQUENCE: 55
gaaattgtga tgactcagag ccctgctaca ctgtccgtca gccctggaga acgtgctaca     60
ctgtcctgtc gcacctcaga agatatttac caggggctgg cttggtatca gcagaagccc    120
ggacaggccc ctaggctgct gatctactcc gctaacactc tgcacatcgg cattccagca    180
cggttctctg gtagtggctc aggaaccgag tttaccctga caatttccag cctgcagtct    240
gaagacttcg cagtgtacta ttgccagcag tactatgatt atcccctggc cttttggcgga    300
gggacaaagg tcgagatcaa acgtggctgg tgcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgcctcc aatcgggtaa ctcccaggag      480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgtt ag                      642

SEQ ID NO: 56              moltype = AA  length = 213
FEATURE                    Location/Qualifiers
REGION                     1..213
                           note = Synthetic sequence
source                     1..213
                           mol_type = protein
                           organism = synthetic construct
SEQUENCE: 56
EIVMTQSPAT LSVSPGERAT LSCRTSEDIY QGLAWYQQKP GQAPRLLIYS ANTLHIGIPA     60
RFSGSGSGTE FTLTISSLQS EDFAVYYCQQ YYDYPLAFGG GTKVEIKTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                 213

SEQ ID NO: 57              moltype = AA  length = 439
FEATURE                    Location/Qualifiers
source                     1..439
                           mol_type = protein
                           organism = Homo sapiens
SEQUENCE: 57
ESGYAQNGDL EDAELDDYSF SCYSQLEVNG SQHSLTCAFE DPDVNTTNLE FEICGALVEV     60
KCLNFRKLQE IYFIETKKFL LIGKSNICVK VGEKSLTCKK IDLTTIVKPE APFDLSVIYR    120
EGANDFVVTF NTSHLQKKYV KVLMHDVAYR QEKDENKWTH VNLSSTKLTL LQRKLQPAAM    180
YEIKVRSIPD HYFKGFWSEW SPSYYFRTPE INNSSGEMDP ILLTISILSF FSVALLVILA    240
CVLWKKRIKP IVWPSLPDHK KTLEHLCKKP RKNLNVSFNP ESFLDCQIHR VDDIQARDEV    300
EGFLQDTFPQ QLEESEKQRL GGDVQSPNCP SEDVVITPES FGRDSSLTCL AGNVSACDAP    360
ILSSSRSLDC RESGKNGPHV YQDLLLSLGT TNSTLPPPFS LQSGILTLNP VAQGQPILTS    420
LGSNQEEAYV TMSSFYQNQ                                                 439

SEQ ID NO: 58              moltype = AA  length = 15
FEATURE                    Location/Qualifiers
REGION                     1..15
                           note = Synthetic sequence
source                     1..15
                           mol_type = protein
                           organism = synthetic construct
SEQUENCE: 58
ESGYAQNGDL EDAEL                                                     15

SEQ ID NO: 59              moltype = AA  length = 15
FEATURE                    Location/Qualifiers
REGION                     1..15
                           note = Synthetic sequence
source                     1..15
                           mol_type = protein
                           organism = synthetic construct
SEQUENCE: 59
AQNGDLEDAE LDDYS                                                     15

SEQ ID NO: 60              moltype = AA  length = 15
FEATURE                    Location/Qualifiers
REGION                     1..15
                           note = Synthetic sequence
source                     1..15
                           mol_type = protein
```

```
                        organism = synthetic construct
SEQUENCE: 60
DLEDAELDDY SFSCY                                                                    15

SEQ ID NO: 61           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 61
AELDDYSFSC YSQLE                                                                    15

SEQ ID NO: 62           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 62
DYSFSCYSQL EVNGS                                                                    15

SEQ ID NO: 63           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 63
SCYSQLEVNG SQHSL                                                                    15

SEQ ID NO: 64           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 64
QLEVNGSQHS LTCAF                                                                    15

SEQ ID NO: 65           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 65
NGSQHSLTCA FEDPD                                                                    15

SEQ ID NO: 66           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 66
HSLTCAFEDP DVNTT                                                                    15

SEQ ID NO: 67           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 67
CAFEDPDVNT TNLEF                                                                    15

SEQ ID NO: 68           moltype = AA  length = 15
FEATURE                 Location/Qualifiers
REGION                  1..15
                        note = Synthetic sequence
source                  1..15
```

```
                        mol_type = protein
                        organism = synthetic construct
SEQUENCE: 68
DPDVNTTNLE FEICG                                                      15

SEQ ID NO: 69           moltype = AA   length = 15
FEATURE                 Location/Qualifiers
REGION                  1..15
                        note = Synthetic sequence
source                  1..15
                        mol_type = protein
                        organism = synthetic construct
SEQUENCE: 69
NTTNLEFEIC GALVE                                                      15

SEQ ID NO: 70           moltype = AA   length = 15
FEATURE                 Location/Qualifiers
REGION                  1..15
                        note = Synthetic sequence
source                  1..15
                        mol_type = protein
                        organism = synthetic construct
SEQUENCE: 70
LEFEICGALV EVKCL                                                      15

SEQ ID NO: 71           moltype = AA   length = 15
FEATURE                 Location/Qualifiers
REGION                  1..15
                        note = Synthetic sequence
source                  1..15
                        mol_type = protein
                        organism = synthetic construct
SEQUENCE: 71
ICGALVEVKC LNFRK                                                      15

SEQ ID NO: 72           moltype = AA   length = 15
FEATURE                 Location/Qualifiers
REGION                  1..15
                        note = Synthetic sequence
source                  1..15
                        mol_type = protein
                        organism = synthetic construct
SEQUENCE: 72
LVEVKCLNFR KLQEI                                                      15

SEQ ID NO: 73           moltype = AA   length = 15
FEATURE                 Location/Qualifiers
REGION                  1..15
                        note = Synthetic sequence
source                  1..15
                        mol_type = protein
                        organism = synthetic construct
SEQUENCE: 73
KCLNFRKLQE IYFIE                                                      15

SEQ ID NO: 74           moltype = AA   length = 15
FEATURE                 Location/Qualifiers
REGION                  1..15
                        note = Synthetic sequence
source                  1..15
                        mol_type = protein
                        organism = synthetic construct
SEQUENCE: 74
FRKLQEIYFI ETKKF                                                      15

SEQ ID NO: 75           moltype = AA   length = 15
FEATURE                 Location/Qualifiers
REGION                  1..15
                        note = Synthetic sequence
source                  1..15
                        mol_type = protein
                        organism = synthetic construct
SEQUENCE: 75
QEIYFIETKK FLLIG                                                      15

SEQ ID NO: 76           moltype = AA   length = 15
FEATURE                 Location/Qualifiers
REGION                  1..15
                        note = Synthetic sequence
```

```
source                    1..15
                          mol_type = protein
                          organism = synthetic construct
SEQUENCE: 76
FIETKKFLLI GKSNI                                                    15

SEQ ID NO: 77             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 77
KKFLLIGKSN ICVKV                                                    15

SEQ ID NO: 78             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 78
LIGKSNICVK VGEKS                                                    15

SEQ ID NO: 79             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 79
SNICVKVGEK SLTCK                                                    15

SEQ ID NO: 80             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 80
VKVGEKSLTC KKIDL                                                    15

SEQ ID NO: 81             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 81
EKSLTCKKID LTTIV                                                    15

SEQ ID NO: 82             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 82
TCKKIDLTTI VKPEA                                                    15

SEQ ID NO: 83             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 83
IDLTTIVKPE APFDL                                                    15

SEQ ID NO: 84             moltype = AA  length = 15
FEATURE                   Location/Qualifiers
REGION                    1..15
```

```
                        note = Synthetic sequence
source                  1..15
                        mol_type = protein
                        organism = synthetic construct
SEQUENCE: 84
TIVKPEAPFD LSVIY                                                          15

SEQ ID NO: 85           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 85
PEAPFDLSVI YREGA                                                          15

SEQ ID NO: 86           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 86
FDLSVIYREG ANDFV                                                          15

SEQ ID NO: 87           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 87
VIYREGANDF VVTFN                                                          15

SEQ ID NO: 88           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 88
EGANDFVVTF NTSHL                                                          15

SEQ ID NO: 89           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 89
DFVVTFNTSH LQKKY                                                          15

SEQ ID NO: 90           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 90
TFNTSHLQKK YVKVL                                                          15

SEQ ID NO: 91           moltype = AA  length = 15
FEATURE                 Location/Qualifiers
REGION                  1..15
                        note = Synthetic sequence
source                  1..15
                        mol_type = protein
                        organism = synthetic construct
SEQUENCE: 91
SHLQKKYVKV LMHDV                                                          15

SEQ ID NO: 92           moltype = AA  length = 15
FEATURE                 Location/Qualifiers
```

```
REGION                    1..15
                          note = Synthetic sequence
source                    1..15
                          mol_type = protein
                          organism = synthetic construct
SEQUENCE: 92
KKYVKVLMHD VAYRQ                                                            15

SEQ ID NO: 93             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 93
KVLMHDVAYR QEKDE                                                            15

SEQ ID NO: 94             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 94
HDVAYRQEKD ENKWT                                                            15

SEQ ID NO: 95             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 95
YRQEKDENKW THVNL                                                            15

SEQ ID NO: 96             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 96
KDENKWTHVN LSSTK                                                            15

SEQ ID NO: 97             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 97
KWTHVNLSST KLTLL                                                            15

SEQ ID NO: 98             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 98
VNLSSTKLTL LQRKL                                                            15

SEQ ID NO: 99             moltype = AA  length = 15
FEATURE                   Location/Qualifiers
REGION                    1..15
                          note = Synthetic sequence
source                    1..15
                          mol_type = protein
                          organism = synthetic construct
SEQUENCE: 99
STKLTLLQRK LQPAA                                                            15

SEQ ID NO: 100            moltype = AA  length = 15
```

```
FEATURE             Location/Qualifiers
REGION              1..15
                    note = Synthetic sequence
source              1..15
                    mol_type = protein
                    organism = synthetic construct
SEQUENCE: 100
TLLQRKLQPA AMYEI                                                    15

SEQ ID NO: 101      moltype = AA  length = 15
FEATURE             Location/Qualifiers
REGION              1..15
                    note = Synthetic sequence
source              1..15
                    mol_type = protein
                    organism = synthetic construct
SEQUENCE: 101
RKLQPAAMYE IKVRS                                                    15

SEQ ID NO: 102      moltype = AA  length = 15
FEATURE             Location/Qualifiers
REGION              1..15
                    note = Synthetic sequence
source              1..15
                    mol_type = protein
                    organism = synthetic construct
SEQUENCE: 102
PAAMYEIKVR SIPDH                                                    15

SEQ ID NO: 103      moltype = AA  length = 15
FEATURE             Location/Qualifiers
REGION              1..15
                    note = Synthetic sequence
source              1..15
                    mol_type = protein
                    organism = synthetic construct
SEQUENCE: 103
YEIKVRSIPD HYFKG                                                    15

SEQ ID NO: 104      moltype = AA  length = 15
FEATURE             Location/Qualifiers
REGION              1..15
                    note = Synthetic sequence
source              1..15
                    mol_type = protein
                    organism = synthetic construct
SEQUENCE: 104
VRSIPDHYFK GFWSE                                                    15

SEQ ID NO: 105      moltype = AA  length = 15
FEATURE             Location/Qualifiers
REGION              1..15
                    note = Synthetic sequence
source              1..15
                    mol_type = protein
                    organism = synthetic construct
SEQUENCE: 105
PDHYFKGFWS EWSPS                                                    15

SEQ ID NO: 106      moltype = AA  length = 15
FEATURE             Location/Qualifiers
REGION              1..15
                    note = Synthetic sequence
source              1..15
                    mol_type = protein
                    organism = synthetic construct
SEQUENCE: 106
FKGFWSEWSP SYYFR                                                    15

SEQ ID NO: 107      moltype = AA  length = 15
FEATURE             Location/Qualifiers
REGION              1..15
                    note = Synthetic sequence
source              1..15
                    mol_type = protein
                    organism = synthetic construct
SEQUENCE: 107
WSEWSPSYYF RTPEI                                                    15
```

```
SEQ ID NO: 108            moltype = AA   length = 15
FEATURE                   Location/Qualifiers
REGION                    1..15
                          note = Synthetic sequence
source                    1..15
                          mol_type = protein
                          organism = synthetic construct
SEQUENCE: 108
SPSYYFRTPE INNSS                                                       15

SEQ ID NO: 109            moltype = AA   length = 15
FEATURE                   Location/Qualifiers
REGION                    1..15
                          note = Synthetic sequence
source                    1..15
                          mol_type = protein
                          organism = synthetic construct
SEQUENCE: 109
YFRTPEINNS SGEMD                                                       15

SEQ ID NO: 110            moltype = AA   length = 31
FEATURE                   Location/Qualifiers
REGION                    1..31
                          note = Synthetic sequence
source                    1..31
                          mol_type = protein
                          organism = synthetic construct
SEQUENCE: 110
KCLNFRKLQE IYFIETKKFL LIGKSNICVK V                                     31

SEQ ID NO: 111            moltype = AA   length = 31
FEATURE                   Location/Qualifiers
REGION                    1..31
                          note = Synthetic sequence
source                    1..31
                          mol_type = protein
                          organism = synthetic construct
SEQUENCE: 111
YEIKVRSIPD HYFKGFWSEW SPSYYFRTPE I                                     31

SEQ ID NO: 112            moltype = AA   length = 327
FEATURE                   Location/Qualifiers
REGION                    1..327
                          note = Synthetic sequence
source                    1..327
                          mol_type = protein
                          organism = synthetic construct
SEQUENCE: 112
ASTKGPSVFP LAPCSRSTSE STAALGCLVK DYFPEPVTVS WNSGALTSGV HTFPAVLQSS       60
GLYSLSSVVT VPSSSLGTKT YTCNVDHKPS NTKVDKRVES KYGPPCPPCP APEFLGGPSV      120
FLFPPKPKDT LMISRTPEVT CVVVDVSQED PEVQFNWYVD GVEVHNAKTK PREEQFNSTY      180
RVVSVLTVLH QDWLNGKEYK CKVSNKGLPS SIEKTISKAK GQPREPQVYT LPPSQEEMTK      240
NQVSLTCLVK GFYPSDIAVE WESNGQPENN YKTTPPVLDS DGSFFLYSRL TVDKSRWQEG      300
NVFSCSVMHE ALHNHYTQKS LSLSPGK                                          327

SEQ ID NO: 113            moltype = AA   length = 459
FEATURE                   Location/Qualifiers
REGION                    1..459
                          note = Synthetic sequence
source                    1..459
                          mol_type = protein
                          organism = synthetic construct
SEQUENCE: 113
MTILGTTFGM VFSLLQVVSG ESGYAQNGDL EDAELDDYSF SCYSQLEVNG SQHSLTCAFE       60
DPDVNTTNLE FEICGALVEV KCLNFRKLQE IYFIETKKFL LIGKSNICVK VGEKSLTCKK      120
IDLTTIVKPE APFDLSVIYR EGANDFVVTF NTSHLQKKYV KVLMHDVAYR QEKDENKWTH      180
VNLSSTKLTL LQRKLQPAAM YEIKVRSIPD HYFKGFWSEW SPSYYFRTPE INNSSGEMDP      240
ILLTISILSF FSVALLVILA CVLWKKRIKP IVWPSLPDHK KTLEHLCKKP RKNLNVSFNP      300
ESFLDCQIHR VDDIQARDEV EGFLQDTFPQ QLEESEKQRL GGDVQSPNCP SEDVVITPES      360
FGRDSSLTCL AGNVSACDAP ILSSSRSLDC RESGKNGPHV YQDLLLSLGT TNSTLPPPFS      420
LQSGILTLNP VAQGQPILTS LGSNQEEAYV TMSSFYQNQ                             459

SEQ ID NO: 114            moltype = AA   length = 219
FEATURE                   Location/Qualifiers
REGION                    1..219
                          note = Synthetic sequence
source                    1..219
                          mol_type = protein
                          organism = synthetic construct
```

```
SEQUENCE: 114
ESGYAQNGDL EDAELDDYSF SCYSQLEVNG SQHSLTCAFE DPDVNTTNLE FEICGALVEV    60
KCLNFRKLQE IYFIETKKFL LIGKSNICVK VGEKSLTCKK IDLTTIVKPE APFDLSVIYR   120
EGANDFVVTF NTSHLQKKYV KVLMHDVAYR QEKDENKWTH VNLSSTKLTL LQRKLQPAAM   180
YEIKVRSIPD HYFKGFWSEW SPSYYFRTPE INNSSGEMD                         219

SEQ ID NO: 115          moltype = AA   length = 7
FEATURE                 Location/Qualifiers
REGION                  1..7
                        note = Synthetic sequence
source                  1..7
                        mol_type = protein
                        organism = synthetic construct
SEQUENCE: 115
FIETKKF                                                              7

SEQ ID NO: 116          moltype = AA   length = 6
FEATURE                 Location/Qualifiers
REGION                  1..6
                        note = Synthetic sequence
source                  1..6
                        mol_type = protein
                        organism = synthetic construct
SEQUENCE: 116
DLSVIY                                                               6

SEQ ID NO: 117          moltype = AA   length = 4
FEATURE                 Location/Qualifiers
REGION                  1..4
                        note = Synthetic sequence
source                  1..4
                        mol_type = protein
                        organism = synthetic construct
SEQUENCE: 117
FKGF                                                                 4

SEQ ID NO: 118          moltype = AA   length = 14
FEATURE                 Location/Qualifiers
REGION                  1..14
                        note = Synthetic sequence
source                  1..14
                        mol_type = protein
                        organism = synthetic construct
SEQUENCE: 118
RKLQEIYFIE TKKF                                                     14

SEQ ID NO: 119          moltype = AA   length = 16
FEATURE                 Location/Qualifiers
REGION                  1..16
                        note = Synthetic sequence
source                  1..16
                        mol_type = protein
                        organism = synthetic construct
SEQUENCE: 119
NFRKLQEIYF IETKKF                                                   16

SEQ ID NO: 120          moltype = AA   length = 17
FEATURE                 Location/Qualifiers
REGION                  1..17
                        note = Synthetic sequence
source                  1..17
                        mol_type = protein
                        organism = synthetic construct
SEQUENCE: 120
DLSVIYREGA NDFVVTF                                                  17

SEQ ID NO: 121          moltype = AA   length = 13
FEATURE                 Location/Qualifiers
REGION                  1..13
                        note = Synthetic sequence
source                  1..13
                        mol_type = protein
                        organism = synthetic construct
SEQUENCE: 121
VVTFNTSHLQ KKY                                                      13

SEQ ID NO: 122          moltype = AA   length = 15
FEATURE                 Location/Qualifiers
REGION                  1..15
```

```
                          note = Synthetic sequence
source                    1..15
                          mol_type = protein
                          organism = synthetic construct
SEQUENCE: 122
EIKVRSIPDH YFKGF                                                         15

SEQ ID NO: 123            moltype = AA  length = 16
FEATURE                   Location/Qualifiers
REGION                    1..16
                          note = Synthetic sequence
source                    1..16
                          mol_type = protein
                          organism = synthetic construct
SEQUENCE: 123
EIKVRSIPDH YFKGFW                                                        16

SEQ ID NO: 124            moltype = AA  length = 19
FEATURE                   Location/Qualifiers
REGION                    1..19
                          note = Synthetic sequence
source                    1..19
                          mol_type = protein
                          organism = synthetic construct
SEQUENCE: 124
EIKVRSIPDH YFKGFWSEW                                                     19

SEQ ID NO: 125            moltype = AA  length = 23
FEATURE                   Location/Qualifiers
REGION                    1..23
                          note = Synthetic sequence
source                    1..23
                          mol_type = protein
                          organism = synthetic construct
SEQUENCE: 125
EIKVRSIPDH YFKGFWSEWS PSY                                                23

SEQ ID NO: 126            moltype = AA  length = 8
FEATURE                   Location/Qualifiers
REGION                    1..8
                          note = Synthetic sequence
source                    1..8
                          mol_type = protein
                          organism = synthetic construct
SEQUENCE: 126
FKGFWSEW                                                                 8

SEQ ID NO: 127            moltype = AA  length = 23
FEATURE                   Location/Qualifiers
REGION                    1..23
                          note = Synthetic sequence
source                    1..23
                          mol_type = protein
                          organism = synthetic construct
SEQUENCE: 127
IYFIETKKFL LIGKSNICVK VGE                                                23

SEQ ID NO: 128            moltype = AA  length = 28
FEATURE                   Location/Qualifiers
REGION                    1..28
                          note = Synthetic sequence
source                    1..28
                          mol_type = protein
                          organism = synthetic construct
SEQUENCE: 128
KSLTCKKIDL TTIVKPEAPF DLSVIYRE                                           28

SEQ ID NO: 129            moltype = AA  length = 19
FEATURE                   Location/Qualifiers
REGION                    1..19
                          note = Synthetic sequence
source                    1..19
                          mol_type = protein
                          organism = synthetic construct
SEQUENCE: 129
LTTIVKPEAP FDLSVIYRE                                                     19

SEQ ID NO: 130            moltype = AA  length = 11
FEATURE                   Location/Qualifiers
```

```
                            -continued
REGION                  1..11
                        note = Synthetic sequence
source                  1..11
                        mol_type = protein
                        organism = synthetic construct
SEQUENCE: 130
APFDLSVIYR E                                                            11

SEQ ID NO: 131          moltype = AA  length = 27
FEATURE                 Location/Qualifiers
REGION                  1..27
                        note = Synthetic sequence
source                  1..27
                        mol_type = protein
                        organism = synthetic construct
SEQUENCE: 131
NKWTHVNLSS TKLTLLQRKL QPAAMYE                                           27

SEQ ID NO: 132          moltype = AA  length = 17
FEATURE                 Location/Qualifiers
REGION                  1..17
                        note = Synthetic sequence
source                  1..17
                        mol_type = protein
                        organism = synthetic construct
SEQUENCE: 132
IKVRSIPDHY FKGFWSE                                                      17
```

ANTIBODIES DIRECTED AGAINST CD127

CROSS-REFERENCE TO RELATED APPLICATIONS

This application is a Continuation of U.S. patent application Ser. No. 16/532,000, filed Aug. 5, 2019, now U.S. Pat. No. 11,440,964, issued on Sep. 13, 2022, which is a Divisional of U.S. patent application Ser. No. 15/317,355, filed Dec. 8, 2016, now U.S. Pat. No. 10,428,152, issued Oct. 1, 2019, which is a National Phase of PCT/EP2015/062993, filed Jun. 10, 2015, which claims the benefit of U.S. Provisional Application No. 62/010,117, filed Jun. 10, 2014, which claims priority to EP 15305078.6, filed Jan. 23, 2015, all of which are incorporated herein by reference in their entireties.

REFERENCE TO SEQUENCE LISTING SUBMITTED ELECTRONICALLY

The content of the electronically submitted sequence listing in XLM file (Name B10744BAA_SEQ LIST_ST26.xml; Size: 182,925 bytes; and Date of Creation: Jun. 2, 2023) filed with the application is incorporated herein by reference in its entirety.

SUMMARY

The invention concerns the field of antibodies directed against the alpha subunit of the receptor for interleukin7 (IL-7), designated CD127 or p90 IL-7R or IL-7Ralpha or IL-7Rα- sometimes also noted IL-7Ra-, especially of the alpha chain of the receptor for human IL-7 expressed on human cells. These antibodies have antagonist properties for IL-7-IL-7R interaction, may present cytotoxic activity against CD127 positive cells but do not increase the maturation of dendritic cells (DCs) induced by TSLP, a cytokine also using CD127 as part of its receptor. Alternatively, or in addition, these antibodies do not induce the internalization of CD127 and/or inhibit the IL7-induced internalization of CD127. According to another aspect of the invention antibodies are provided which recognize a human CD127 epitope comprising sequences from the 2b site of CD127, in particular the epitope comprises human CD127 sequences of domain D1 and of the 2b site of CD127, in particular the epitope comprises at least one sequence from D1 comprising SEQ ID No: 115 (in particular comprising SEQ ID No: 110) and a sequence from the 2b site comprising the sequence of SEQ ID No: 116 and optionally also comprises SEQ ID No: 117 (in particular comprises SEQ ID No: 111).

Accordingly the antibodies of the invention are suitable for use in order to remedy to a condition diagnosed in a human patient which results from pathogenesis related to lymphopoiesis, when IL-7 signalling pathways provide contribution to said pathogenesis, especially when an increase in the maturation, more precisely the upregulation of costimulatory molecules, of dendritic cells is undesirable.

Biochemistry

CD127 is common to the IL-7 receptor (IL-7R) and to the TSLP receptor (TSLPR). The IL-7R is constituted of a heterodimer of CD127 and the common gamma chain (γc) of interleukin receptors. The common gamma chain γc is sometime referred to herein and in the literature as CD132. IL-7R is bound by Interleukin 7. The TSLP receptor is a heterodimer of CD127 and cytokine receptor-like factor 2 (CRLF2). The TSLP receptor is bound by TSLP. In the literature, TSLPR is sometimes used to designate both the CRLF2 chain of the receptor, and the CD127/CRLF2 complex. In order to avoid confusion, in what follows TSLPR usually designates the complex.

CD127 (Swiss Prot accession number P16871) may exist in four isoforms. The canonical isoform, also termed H20 (Swiss Prot P16871.1) is a single-pass transmembrane protein and has 459 amino acids consisting, from N- to C-terminal, of a 20 amino-acid signal peptide, a 219 amino acid extracellular domain, a 25 amino-acid transmembrane domain and a 195 amino-acid intracellular domain. Other isoforms share the sequence of all of (or most of) the extracellular domain of H20 and display varied C-terminal sequences. Isoforms 2 and 4 are secreted (Swiss Prot P16871-4 and P16871-3), while isoform 3 (Swiss Prot P16871-2) is also a transmembrane protein. The sequence of CD127, without the signal peptide, is provided herein as SEQ ID No: 57. When referring to numbered amino acids of CD127 in the present application, said sequence will serve as reference for the numbering. CD127 is reported to have the sequence of SEQ ID No:113, and its extracellular domain, when the signal peptide is removed, has the sequence of SEQ ID No: 114. Unless otherwise stated, the numbering used herein for amino acids of CD127 is the numbering from SEQ ID No:114.

CD127 is a Cytokine Receptor Homology class I (CRH I) receptor. As is well known in the art, the extracellular domain of these receptors consists of two fibronectin 3 domains, termed D1 and D2. The precise crystallographic structure of CD127 has been published and discussed in e.g. McElroy et al., 2009; McElroy et al., 2012 and Walsh, 2012 and in particular has been disclosed as protein structure data in the Research Collaboratory for Structural Bioinformatics Protein Data Bank (RCSB PDB) database, with the accession number 3UP1. D1 is generally considered to be involved in the binding with IL-7, while D2 is involved in the binding to the γc chain (and also with IL-7). Importantly, the site 2b of domain D2, essentially consisting of amino acids 109 to 127 of SEQ ID No: 114 (see Walsh, 2012) is critical for the CD127-γc interaction, in particular to allow or increase binding of CD127 with γc in the presence of IL-7. In particular, mutations at P112 and L115, which have been identified in patients suffering from Severe combined immunodeficiency (SCID), are thought to destabilize the hydrophobic core of the D2 domain which likely results in their pathogenic feature. As said above, the 2b site consists essentially of amino acids 109 to 127; the skilled person will appreciate that the extremities of such a domain may not necessarily be defined unambiguously with a single-base precision and that the 2b site may be understood to comprise, at either or both ends of the mentioned sequence, 1, 2, or 3 more or less amino acids. Therefore, when referring herein to the 2b site of CD127, this should be understood to refer to a sequence of CD127 starting at position 106, 107, 108, 109, 110, 111 or 112 and ending at position 124, 125, 126 or 127; in particular to such a sequence which is thought or shown to constitute an essential binding site with the γc chain of the IL7-R, in particular in the presence of IL-7.

IL-7R signalling. Binding of IL-7 to IL-7R triggers the activation of several signalling pathways, including the Janus kinases (JAK)-1 and -3, signal transducer and activator of transcription 5 (STAT5) and phosphatidylinositol 3-kinase (PI3-k). STAT1 and STAT3 pathways are reported to be activated, although they do not seem to be the main pathways. The activation of the STAT5 pathway is required for the induction of the anti-apoptotic protein Bcl-2 and the prevention of the entry of the pro-apoptotic protein Bax in the mitochondrion and thus for survival of thymic developing T cell precursors. The activation of the PI3-k pathway results in the phosphorylation and cytoplasmic retention of the pro-apoptotic protein Bad.

TSLPR signalling. Thymic Stromal Lymphopoietin, (TSLP) is an epithelial Cell Cytokine that is active in lymphopoiesis and in particular is involved in regulation of development of cells of the immune system, said regulation impacting in particular the maturation of said cells. Human TSLP (Genbank accession number AF338732) is a factor which exerts polarization of dendritic cells and promotes T and B cell proliferation and differentiation. TSLP also suppresses the generation of Treg cells (Lei et al., 2011).

TSLP-induced signaling pathways have been shown to be different, at the molecular level, from IL-7-induced pathways. In particular, while TSLP binding to its receptor also activates Jak-1, it does not activate Jak-3 but does activate Jak-2. These differences are consistent with the observation that Jak-1 associates with CD127, shared by both receptors while Jak-2 associates with CRLF2 and Jak-3 with γc (Rochman et al., 2010). The activation of the STAT5 pathway is also reported for TSLP-induced signaling (Zhong et al., 2014). One major effect of TSLP is to lead to the activation of dendritic cells, inducing the overexpression of costimulatory molecules such as CD80, thereby promoting TH-2 mediated inflammatory responses (Reche et al., 2001).

Cellular Biology

"CD127-positive cells" designates cells expressing CD127 at their cell surface. In most cases, CD127-positive cells express CD127 in a complex forming the IL-7R (IL-7R-positive cells) and/or in a complex forming the TSLPR (TSLPR-positive cells). CD127 is expressed by various cells, including by both memory and naive T cells. CD127 is in particular expressed by effector T cells (Teff), including resting and memory T cells, and by immature B cells, but is especially not expressed by resting natural regulatory T cells (natural Treg). IL-7Rα is essential for promoting thymocyte differenciation and clonal expansion of lymphocytes.

The importance of the IL7-CD127 pathway for naïve T-cell homeostasis is underlined by several recent studies showing that expression levels of membrane-bound IL-7Rα on conventional CD4+ T cells correlate with frequencies of recent thymic emigrant (RTE)-CD4+ T cells in healthy individuals and HIV-infected patients as well as in patients with MS (Albuquerque et al., 2007) (Broux et al., 2010). IL-7Rα is also a component of the TSLP receptor. The secretion of TSLP by Hassall's corpuscles, structures composed of epithelial cells in the thymic medulla, has been demonstrated to condition CD11c+ myeloid dendritic cells (MDCs) to induce the differentiation of thymocytes into Treg (Watanabe et al., 2005a). Accordingly, signals from the IL-7 receptor are required for Treg development as shown in IL-7Rα knockout mice (Mazzucchelli et al., 2008). In (Haas et al., 2011), the authors showed a reduced IL-7Rα expression on conventional T cells and upregulated IL-7 plasma levels together with reduction of recent thymic emigrant-Treg frequencies and Treg function in MS, without clear genetic influence (Haas et al., 2011).

Dissecting how IL-7 regulates its cognate receptor membrane trafficking is crucial to the in-depth understanding of the role of IL-7/IL-7R in lymphocyte function. Previous studies have suggested that IL-7 stimulation of T cells leads to surface down-modulation of CD127 within 30 minutes, possibly because of receptor internalization. At later time points (2-6 hours), IL-7 was shown to induce transcriptional down-regulation of CD127. However, the actual dynamics of CD127 internalization and the regulation of trafficking mechanisms by IL-7 remain to be elucidated (Henriques et al., 2010). It was also suggested that IL-7-induced signaling is dependent on CD127 internalization and that subsequent receptor degradation relies on JAK3 activity and is mediated by both proteasomes and lysosomes.

Physiopathology

Dendritic cells express high levels of costimulatory molecules after maturation, such as CD80, which promotes T cell mediated immune responses. They also produce the cytokine TARC (CCL17), which induces chemotaxis in T cells. As such, mature dendritic cells contribute to the physiopathology of several immune-mediated diseases where T cell responses are at play, as for example in asthma, rheumatoid arthritis, colitis, multiple sclerosis and uveitis. Mature dendritic cells also play a key role in the rejection process of cells, tissues or organ allografts. Therefore many therapeutic strategies aim at preventing dendritic cells maturation.

The presence or absence of costimulatory molecules on antigen-presenting cells (APCs), such as dendritic cells significantly influences the qualitative and quantitative nature of an immune response. Overexpression of CD80 by dendritic cells causes DC maturation and inceases memory T cell activation (Bour-Jordan et al., 2011). Mechanistically, interaction of CD28 with CD80 occupies the central cluster of the immunological synapse and is colocalized with the engaged TCR, thereby stabilizing the immune synapse (Dustin and Shaw, 1999) (Grakoui et al., 1999). The interaction between CD28 and CD80 actually generates the appropriate spacing for TCR to efficiently interact with HLA molecules (Shaw and Dustin, 1997).

Multiple sclerosis (MS) is an inflammatory demyelinating disease of the central nervous system (CNS). The appearance of demyelinating patches in the CNS of patients with MS is associated with an inflammatory infiltrate mainly composed of macrophages and T lymphocytes. On a mechanistic level, the MS is considered as a autoimmune disease. MS is typically considered as a disease primarily mediated by CD4+ T cells. Particular subsets of CD4+: Th1 and more recently Th17, were implicated in the pathophysiology of the disease. At present, it is still difficult to assign specific roles to each subpopulation Th1 and Th17. Furthermore, inhibition of leucocyte trafficking by antagonism of the alpha4 (α4)-integrin has now been validated as a therapeutic approach for the treatment of inflammatory diseases such as MS and inflammatory bowel disease (IBD) and as well for the treatment of atherosclerosis (Zhi et al., 2014). α4β7 is expressed on a more restricted set of leucocytes including activated macrophage, subsets of lymphocytes, NK cells, mast cells and eosinophils.

Human IL-7 induces strong expression of α4 and β7 integrins in vitro on human T lymphocytes and dramatically increases the frequency of human T lymphocytes expressing α4, β7 and α4/β7 integrins (FIG. 19), which are required for T lymphocytes homing and retention in non-lymphoid tissues such as intestine, brain and skin (Denucci et al., 2009; Gorfu et al., 2009).

Naive T cells are partly responsible for acute rejection of transplanted organs and tissues. These cells can be controlled by current immunosuppressive drugs (calcineurin inhibitors) and by monoclonal antibodies that block costimulation (anti-adhesion, CD80/86 inhibitors). Memory T cells are also responsible for transplant rejection. Memory T cells accumulate in man due to the acquired immune history, mainly former reactions against viruses. It has been shown that memory T cells can be reactivated by alloantigens as a result of "heterologous immunity", which is the cross-reaction of our anti-viral defenses with alloantigens (Adams et al., 2003). Heterologous immunity represents a potent barrier to tolerance induction since memory T cells, in contrast to naive T cells, are programmed to activate quickly, with a reduced requirement for costimulatory signals. Memory T cells may also be involved in chronic rejection. Beside their role in organ and tissue transplantation, naïve and memory T cells are also co-responsible for many autoimmune diseases. This is the case for ulcerative colitis (Shinohara et al., 2011), rheumatoid arthritis, psoriasis or graft-versus-host disease.

Furthermore, several malignant cells have been shown to display IL-7R. This is the case for Sezary cutaneous lymphoma (60% of them), or childhood acute lymphoblastic leukemia in which about 15% of the cases develop gain-of-function mutation in CD127, rendering these tumors partially IL-7 dependent (Shochat et al., 2011).

The depletion of T lymphocytes has been an obvious immunosuppressive approach to counteract allograft rejection or fight autoimmunity. However, total T cell depletion might not be favorable for the induction of immunological tolerance. Targeting T cell subpopulations or selectively activated T cells, without modifying Treg cells, could constitute a pro-tolerogenic approach (Haudebourg et al., 2009). CD127 may thus be regarded as a potential attractive therapeutic target for monoclonal antibodies (Mabs) aimed at modulating immune responses since such monoclonal antibodies could have the potential of depleting effector but not regulatory lymphocytes. It has been assumed accordingly that they might show efficacy in transplantation, autoimmunity (Michel et al., 2008) and malignancies by antagonizing access of IL-7 to IL-7-R and thereby limiting T and B cell function and growth.

A therapy with a monoclonal antibody against CD127$^+$ cells that interferes with the IL-7 pathway could fulfill that goal by eliminating/neutralizing naïve and memory T cells and/or reducing their number while preserving Treg cells or by eliminating or reducing the number of CD127-positive malignant cells. A therapy with a monoclonal antibody against CD127$^+$ cells might however act as a double edge sword if it leads to dendritic cells activation. Indeed, CD127 is also expressed by dendritic cells in association with CRLF2, forming the TSLP receptor. In the presence of TSLP, dendritic cells get activated and promote T cell-mediated immune responses. Some monoclonal antibodies against CD127, presumably by modifying the way TSLP interacts with TSLP receptor, have the property to increase the maturation of dendritic cells induced by TSLP (as shown FIG. 7 with the medium condition). As a consequence, a therapy with a monoclonal antibody against CD127 that would not increase the maturation of dendritic cells induced by TSLP would present a therapeutic advantage. It would present the benefit of IL7R blockade without the drawback of activating dendritic cells in an inflamed environment containing TSLP.

In a publication (Racapé et al., 2009) the authors analysed the interest of IL-7 receptor alpha (IL7Rα) as a potential therapeutic target in transplantation. Having reviewed the expression of IL-7Rα on various T cells and IL-7 responsive cells, the authors determined whether targeting memory T cells expressing IL-7Rα could prolong allograft survival in mice and conclude that targeting IL-7 or IL-7Rα would advantageously spare Treg cells. Among the perspectives, the authors pointed out that targeting either IL-7 or IL-7Rα in therapeutic treatment might have different consequences on the survival of the cells expressing CD127 and might elicit different type of lymphopenia. The question of the effects of antibodies that would be directed against IL-7Rα depending upon whether they would be blocking or neutralizing or cytotoxic antibodies was also posed from a conceptual point of view. The authors nevertheless did not show having obtained and assayed such antibodies and rather expressed the need for further study to assess the relevancy of the hypothesis.

In view of the drawbacks of available therapeutic approaches in immune related diseases and other diseases involving the IL-7/IL-7Rα such as different types of cancers, including some breast cancers, there is still a need for further drug candidates, especially for candidates active with respect to more selective targets for the purpose of controlling e.g. modulating immune activation in human patients.

In this context, monoclonal antibodies against IL-7Rα having antagonist properties toward IL-7Rα have been disclosed in WO2010/017468 and their humanized versions in WO2011/094259 with a view to treat autoimmune diseases like multiple sclerosis. The described antibodies are said to be antagonist for IL-7 binding to its receptor, and active against $T_H17$ and $T_H1$ cells expansion and survival which were said to require IL-7 interaction with their CD127 receptor. The effect of these antibodies on the maturation of immune cells, and particularly of dendritic cells, has not been considered. Besides, these antibodies are said not to inhibit TSLP-induced production of TARC (p. 107 of WO2011/094259). Similarly, anti-CD127 antibodies reported in WO2011/104687 or in WO2013/056984, which are contemplated for use in the treatment of diabetes, lupus, rheumatoid arthritis and other autoimmune diseases, have not been discussed with respect to their possible effect on the maturation of dendritic cells and their interaction with TSLP-induced signalling has not been reported. In addition, as published by Kern et al (Kern et al., 2013; Kern et al., 2015) and as shown herein, the anti-CD127 antibodies of the prior art induce internalization of the receptor. Since antagonist anti-CD127 antibodies that also induce internalization of CD127 fail to control cutaneous type IV hypersensitivity (FIG. 10), whereas antagonist anti-CD127 antibodies that do not induce internalization do, it might be that the internalization process activates the signalling pathway, mitigating the antagonist effect of the antibodies. Last, the antibodies of the prior art recognize an epitope which does not comprise any sequence from the 2b site of CD127 (i.e. in particular from amino acids 109-127 of SEQ ID No:114); and have not been shown to disrupt the binding of CD127 with the γc chain of the IL7-R.

Despite recent interest in the development of CD127 antibodies, efforts have thus concentrated on the inhibition of IL7-induced IL-7R signalling. Nonetheless, TSLP and the TSLPR have been involved in a number of pathologies. TSLP has been shown to play a role in skin and lung diseases (He and Geha, 2010) and to associate to various pathologies including airway inflammatory disease and atopic dermatitis in human and mice (Ying et al., 2008) (Jariwala et al., 2011). In addition TSLP has been shown to associate to regulation of intestinal immunity and inflammation (Taylor et al., 2009). Other pathologies involving TSLP and the TSLPR include pediatric B-cell leukemia (van Bodegom et al., 2012), lung- and skin-specific allergic disorders, autoimmunity-related diseases (Roan et al., 2012) and cancer, including breast cancer (Olkhanud et al., 2011).

Therefore, while it is abundantly acknowledged in the prior art that anti-CD127 antibodies are promising candidates for the treatment of immunity-related diseases through antagonism of the IL-7-induced and/or IL-7-R mediated mechanisms, and that such antibodies would also bind CD127 in the context of the TSLP receptor and interfere with TSLP-induced and/or TSLP receptor-mediated mechanisms, their possible involvement in maturation of dendritic cells was not questioned and the improvement consisting in obtaining antibodies that do not display the effect of increasing the maturation of dendritic cells and/or that do not induce internalization of CD127 and/or that inhibit IL7-induced internalization, was never suggested in the prior art.

Following their surprising discovery of the undesired increase induced by existing anti-CD127 antibodies in the maturation of dendritic cells induced by TSLP (although the antibodies inhibit TSLP-induced production of TARC), the inventors have developed antibodies which do not display such increase and thus are more suitable for treatment of diseases, in particular of autoimmune diseases. Moreover, the inventors have discovered that antibodies which do not induce internalization and/or inhibit IL7-induced internalization of CD127 have high efficiency, especially in vivo compared to prior art antibodies such as MD707-13.

The invention provides means suitable in this context, relating to monoclonal antibodies against IL-7Rα that interfere only negatively with the TSLP pathway. Accordingly the monoclonal antibodies (Mabs) of the invention do not increase TSLP-induced dendritic cell maturation, contrary to what was observed by the inventors with conventional anti-CD127 antibodies. In addition or alternatively, the antibodies of the invention do not induce internalization of CD127 and/or inhibit IL7-induced internalization of CD127. In a particular embodiment, the antibodies provided in the invention combine these DC maturation- and/or internalization-related properties with antagonist activity toward IL-7/IL-7-R signaling. In particular embodiments, the antibodies of the invention inhibit IL7-induced expression of α4, β7 and α4/β7 integrins in T cells, in particular in vivo. These Mabs with novel mechanisms of action therefore constitute new products for evaluating therapeutic benefits of CD127 targeting.

Furthermore, the inventors disclose the epitope recognized by a preferred antibody of the invention, thus allowing for straightforward development of alternative antibodies and/or fragments or antigen-binding domains thereof or structurally-related antigen-binding domains from other types of polypeptides, which bind the relevant epitope and preserve the desired features.

Epitopes from CD127 recognized by N13B2 were identified by array-based oligo-peptide scanning (sometimes called overlapping peptide scan or pepscan analysis) and comprise the amino acid sequences of human CD127 consisting of the sequences of ep1 (SEQ ID No: 110), ep2 (SEQ ID No: 111) and ep3 (SEQ ID No:86). This technique uses a library of oligo-peptide sequences from overlapping and non-overlapping segments of a target protein and tests for their ability to bind the antibody of interest. By combining non-adjacent peptide sequences from different parts of the target protein and enforcing conformational rigidity onto this combined peptide (such as by using CLIPS scaffolds) (Timmerman et al., 2007), discontinuous epitopes can be mapped with very high reliability and precision (Cragg, 2011) (Gaseitsiwe et al., 2010). Further determination of the epitope, using proteolysis protection procedures, allowed to determine that the conformational epitope comprises the amino acid sequences of human CD127 having the sequences of SEQ ID No: 115, SEQ ID No: 116 and SEQ ID No: 117. The epitope therefore comprises sequences from the 2b site of CD127. Furthermore, the epitope comprises sequences in both domains D1 and D2 of CD127 and more specifically sequences from the D1 domain along with sequences from the 2b site. Epitopes according to the invention are described in more detail below. In particular, said epitopes consist of SEQ ID No:115 (or SEQ ID No:110), SEQ ID No:116 (or SEQ ID No:86) and SEQ ID No:117 (or SEQ ID No:111) in their conformational arrangement in the native CD127.

In a particular embodiment, the monoclonal antibodies also exert a cytotoxic action against target CD127+ cells that also physically reduce their number (contraction of the subpopulation).

The invention thus concerns a macromolecule, such as an antibody, an antigen-binding fragment of an antibody or a chimeric molecule comprising an antibody or a fragment thereof, which (i) binds specifically the alpha chain of the receptor to IL-7 (designated CD127) through antibody-antigen interaction, especially of the alpha chain of the IL-7 receptor expressed by human CD127 positive cells, and which (ii) does not increase the maturation of dendritic cells induced by TSLP (characterized e.g. by increased expression of cell surface antigens CD80 and/or CD40) and/or (iii) does not induce internalization of CD127 and/or inhibits IL7-induced internalization of CD127.

In a particular embodiment of the invention, said macromolecule comprises a VH chain comprising at least one of the following amino acid sequences:
  VHCDR1 SEQ ID No:10;
  VHCDR2 SEQ ID No:12;
  VHCDR3 SEQ ID No:14 or SEQ ID No: 48;
  VH SEQ ID No:22
and/or a VL chain comprising at least one of the following amino acid sequences:
  VLCDR1 SEQ ID No:16 or SEQ ID No: 50;
  VLCDR2 SEQ ID No:18 or SEQ ID No: 52;
  VLCDR3 SEQ ID No:20;
  VL SEQ ID No:24.

In particular embodiments, the macromolecule exhibits cytotoxic activity against human T cells expressing CD127 (CD127+ cells). In other embodiments, the macromolecule does not exhibit cytotoxic activity against human T cells expressing CD127 (CD127+ cells).

The invention also concerns compositions comprising said macromolecule, methods of obtaining said macromolecules and uses of said macromolecules and compositions.

As used herein, a macromolecule designates any molecule, especially a molecule of biological origin or a molecule comprising fragments of biological origin, having a molecular weight of more than 500 Da. Macromolecules include, but are not limited to, polypeptides and modified polypeptides such as glycosylated polypeptides and conjugates thereof. As used herein, a macromolecule which "binds specifically CD127 through antibody-antigen interactions" means that the interactions between said macromolecule and CD127 essentially consist in the same interactions as these between an antibody specific to CD127 and CD127. In particular, said macromolecule may comprise the residues of the antibody that are involved in said interaction, in a spatial configuration allowing the formation of the same chemical bounds with the CD127 protein. In a particular embodiment, the macromolecule comprises at least one CDR sequence of a VH chain and/or of a VL chain of an antibody. In a preferred embodiment, the macromolecule comprises all of the CDR sequences of the VH chain and/or of the VL chain of an antibody. In a preferred embodiment, the macromolecule comprises the entire VH chain and/or the entire VL chain of an antibody.

In particular embodiments, the macromolecule is produced, designed or selected to recognize an epitope defined as follows (defined by at least one of the following features):

(a) the epitope comprises sequences, in particular at least 3, 4, 5, 6 or 7 consecutive amino acids, taken from the 2b site of CD127, in particular from amino acids 109-127 of SEQ ID No:114, more particularly from amino acids 110-125, 110-120, 112-120 of SEQ ID No:114, more particularly from amino acids 114-119 of SEQ ID No: 114 (corresponding to SEQ ID No: 116); in particular, the epitope comprises SEQ ID No:116, in particular comprises SEQ ID No:86; in particular, the epitope comprises P112 or L115 of CD127;

(b) in addition to the features of (a) above, the epitope comprises sequences, in particular at least 3, 4, 5, 6 or 7 consecutive amino acids, taken from the D1 domain of CD127, in particular from amino acids 1-98 of SEQ ID No:114; in particular, the epitope comprises the amino acid sequences of SEQ ID No: 115 (in particular comprises the amino acid sequence of ep1 (SEQ ID No:110)

(c) in addition to the features of (a), and optionally of (b) above, the epitope comprises sequences, in particular 3, 4, 5, 6 or 7 consecutive amino acids, taken from amino acids 180-220 of SEQ ID No:114, in particular from amino acids 190 to 200; in particular the epitope comprises the amino acid sequence of SEQ ID No:117; in particular comprises the amino acid sequence of ep2 (SEQ ID No:111);

(d) the epitope comprises the sequences of SEQ ID No:115 and the sequences of SEQ ID No:116, or the epitope comprises the sequence of SEQ ID No:117 and the sequences of SEQ ID No:116; in particular the epitope comprises the sequences of SEQ ID No:115, SEQ ID No:116 and SEQ ID No:117;

(e) the epitope comprises sequences of CD127 as defined in (a), (b) (c) and/or (d) above, and no other amino acid sequences (of more than 3, 4, or 5 consecutive amino acids) of CD127 than the ones explicitly mentioned, i.e. in particular, the epitope comprises only the following sequences from CD127:
  one sequence taken from site 2b, in particular consisting of amino acids 109-127 of SEQ ID No:114, or amino acids 110-125, 110-120, or 112-120 of SEQ ID No:114, or amino acids 114-119 of SEQ ID No:114 (corresponding to SEQ ID No:116), or the sequence corresponding to SEQ ID No:86, and/or consisting of a sequence of 3 amino acids or more than 3, 4, 5, 6, 7 amino acids and of 19 amino acids or less than 19, 18, 15, 11 amino acids taken from site 2b, in particular such a sequence comprising P112 or L115 of CD127;
  optionally, in addition to the sequence of site 2b, one sequence taken from domain D1 of CD127, in particular from amino acids 98 of SEQ ID No:114, in particular one sequence consisting of SEQ ID No:110 or of SEQ ID No:115, and/or consisting of a sequence of 3 amino acids or more than 3, 4, 5, 6, 7 amino acids and of 20 amino acids or less than 20, 18, 16, 11 amino acids comprising SEQ ID No:115 or comprised in the sequence of SEQ ID No:115;
  optionally, in addition to the sequence of site 2b and to the optional sequence from domain D1 if present, one sequence taken from amino acids 180 to 220 of SEQ ID No:114; in particular one sequence consisting of SEQ ID No:111 or of SEQ ID No:117, and/or consisting of a sequence of 3 amino acids or more than 3, 4, 5, 6, 7 amino acids and of 20 amino acids or less than 20, 18, 16, 11 amino acids comprising SEQ ID No:117 or comprised in the sequence of SEQ ID No: 117;
  said epitope possibly comprising additional amino acids, provided these additional amino acids are not taken from the sequence of CD127 (i.e. provided the epitope does not comprise more than 3, 4 or 5 consecutive amino acids from the sequence of CD127 apart from the sequence from site 2b and possibly the optional sequences from domain D1 and from amino acids 180-220 of SEQ ID No: 114 described above);

(f) the epitope, in addition to the feature described in (a), (b), (c) or (d) above, does not comprise more than 3, 4 or 5 consecutive amino acids taken from the region 99-108 of SEQ ID No:114, does not comprise more than 3, 4 or 5 consecutive amino acids taken from the region 128-179 of SEQ ID No: 114 and/or does not comprise more than 3, 4 or 5 consecutive amino acids from the region 220-239 of SEQ ID No:114, in particular does not comprise more than 3, 4 or 5 consecutive amino acids from either region 99-108, 128-179 and 220-239 of SEQ ID No:114;

(g) the epitope comprises the combination of sequences of CD127 as defined in (a), (b), (c), (d), (e) and/or (f) above, wherein some amino acids have been mutated, in particular deleted and/or substituted, in particular substituted by an amino acid with similar properties (conservative substitutions); in particular, the epitope consists of or comprises sequences having at least 80%, 85%, 90%, or 95% sequence identity with the sequences of CD127 as defined in (a), (b), (c), (d), (e) and/or (f) above, in combination as defined in (b), (c) or (d) where relevant;

(h) the epitope is a conformational epitope having the features defined in (a), (b), (c), (d), (e), (f) and/or (g) above, i.e. comprises or consists of the sequences as defined in (a), (b), (c), (d), (e), (f) and/or (g) above in a conformation which mimics the conformation of said sequences within the native CD127 (either as a monomer or as a dimer with γc and/or associated with IL-7);

(i) the epitope comprises a fragment of CD127 (i.e. a stretch of consecutive amino acids) with the features of (a), (b), (c), (d), (g) and/or (h) above;

(j) the epitope has the features defined in (g) above and is obtained by a technology such as the CLIPS technology which allows the synthesis of peptide assemblies with predictable structure.

In particular embodiments of epitopes with the features of (b) and (c), the epitope includes the amino acid sequence of CD127 which is intercalated between the two sequences ep1 and ep2, and optionally do not extend to include any, or do not extend to include more than one amino acid of the sequence of the human CD127 sequence upstream (i.e. N-terminal of the sequence of ep1) and/or downstream (i.e. C-terminal of the sequence of ep2) of these sequences. In other particular embodiments, the epitope is such that none of the ep1 or ep2 sequences is extended to include any of their adjacent amino acids in the human CD127 sequence, or to include more than 7, 5 or 1 consecutive amino acids from their adjacent amino acids in the sequence of human CD127 which is intercalated between ep1 and ep2; the extension of the ep1 and ep2 sequences may in this case also be limited upstream (of ep1) or downstream (of ep2) as above. In particular embodiments, the sequences of CD127 which comprise the epitope sequences above are not extended to comprise their adjacent amino acids from the human CD127 sequence by more than 1 amino acid N-terminal or by more than 7 amino acids C-terminal adjacent to ep1, or by more than 30 amino acids N-terminal or 30 amino acids C-terminal adjacent to ep2.

In embodiments where the macromolecule is produced, designed or selected to recognize an epitope comprising several non-contiguous amino acid sequences of CD127 (i.e. sequences which are not contiguous in the primary sequence of CD127), it is possible to produce or select antibodies which recognizes an epitope comprising one of said CD127 sequences, and then select among these antibodies those that recognize the other CD127 sequence(s) (said later selection may also be performed by successive selections if more than two non-adjacent CD127 sequences are to be recognized).

The present invention also includes the conformational epitope recognized by the antagonist antibodies of the invention. The present invention also includes antibodies that bind this conformational epitope. The embodiments include a CD127 conformational epitope comprising (i) the domain having at least 80%, 85%, 90%, or 95% sequence identity with SEQ ID NO. 115 and/or the domain having at least 80%, 85%, 90%, or 95% sequence identity with SEQ ID NO. 117 and (ii) the domain having at least 80%, 85%, 90%, or 95% sequence identity with SEQ ID NO. 116. More particularly, the CD127 conformational epitope comprising amino acid residues 73-79 and/or 114-119 and amino acid residues 193-196 of SEQ ID No:114. The present invention includes antibodies that bind this conformational epitope. In particular embodiments, the macromolecule is produced, designed or selected to recognize a conformational epitope comprising the amino acid sequences of human CD127 having the sequences of SEQ ID No: 115, SEQ ID No: 116 and SEQ ID No: 117.

In particular, in the above embodiments, the antibody is raised against an immunogen which consists of or comprises an epitope as described, i.e. is initially produced by immunization of an animal which is not a human, in particular a mammal, with an antigen comprising or consisting of said epitope. Accordingly, the invention also relates to an antigen of which the epitope is as described above, in particular to its use as an immunogen in the production of antibodies and/or to its use in selection and/or testing methods to produce an antibody or antigen-binding fragment or other macromolecule. The invention also relates to said methods using said antigen. Since antigens may comprise non-peptidic constituents in addition to peptidic constituents and/or may comprise peptidic constituents which do not form part of the epitope, it should be understood herein that, unless otherwise stated or obvious from the context, when referring to the sequence of an antigen and/or to the features of said sequence, said sequence or features should be understood to designate the sequence (or features thereof) of the epitope part of the antigen. If the antigen comprises amino acids which do not form part of the epitope, said amino acids preferably do not comprise more than 3, 4 or 5 consecutive amino acids of CD127.

Accordingly and unless it appears technically irrelevant, the definitions and features disclosed herein with respect to the antibodies or their fragments similarly apply to any macromolecule of the invention.

Binding of CD127

In accordance with the invention, "binding" to the IL-7Rα protein refers to an antigen-antibody type interaction and encompasses "specific binding" properties of the antibodies or antigen-binding fragments thereof which specific binding means that the antibodies or antigen-binding fragments bind to the IL-7Rα protein while they do not bind or bind with a significantly weaker affinity to other proteins (e.g. the common cytokine receptor γ-chain). Specific binding is preferably defined and/or determined in physiological conditions, especially in terms of pH and salt content of the testing solution. Binding and binding specificity can be assayed in accordance with the tests disclosed in the Examples and in particular can be assayed by Biacore, ELISA, or Western Blot analysis.

In a particular embodiment of the invention, the antibodies or antigen-binding fragments thereof target and bind the IL-7-R alpha chain when it is complexed in the TSLP-Receptor (with CCRF2; Genbank accession Number AF338733; Reche et al., 2001).

In a particular embodiment, the antibodies or fragments thereof or chimeric molecules of the invention bind to CD127 as an isolated protein with a dissociation constant (Kd) lower than 5E-10 M. In a preferred embodiment, the dissociation constant (Kd) is lower than 1E-10 M or lower than 9E-11 M, or lower than 5E-11 M.

In particular embodiments, the antibodies or fragments thereof or chimeric molecule or other macromolecule of the invention binds to an antigen of human CD127 comprising the sequences of ep1 (SEQ ID No: 110) and/or ep2 (SEQ ID No: 111). In particular embodiments, the antigen comprises a fragment of human CD127 comprising both ep1 and ep2 (i.e. the antigen comprises the sequences of ep1 and ep2 and the intercalated sequences of human CD127). In other embodiments, the antigen comprises only ep1 and ep2 sequences from human CD127, possibly in addition to other sequences from other origin, which are distinct from human CD127 sequences. In yet other embodiments, ep1 and/or ep2 sequences are extended to include a few additional amino acids from human CD127, in particular up to one amino acid N-terminal to ep1, up to 7 amino acids C-terminal to ep1, up to 1, 10, 20 or 30 amino acids N-terminal to ep2, up to 7; 10, 20 or 30 amino acids C-terminal to ep2. Particular antigens include: an antigen as above, preferably comprising both ep1 and ep2, wherein the sequence of CD127 comprising ep1 does not extend to comprise the amino acids adjacent to said sequence in the sequence of human CD127, or does not extend to comprise more than 1 amino acid N-terminal or more than 7 amino acids C-terminal of ep1 in the sequence of human CD127; and an antigen as above wherein the sequence of CD127 comprising ep2 does not extend to comprise the amino acids adjacent to said sequence in the sequence of human CD127, or does not extend to comprise more than 30 amino acids N-terminal or more than 30 amino acids C-terminal of ep2 in the sequence of human CD127; and antigens having both these features. In particular embodiments, the antibodies or fragments thereof or chimeric molecule or other macromolecule of the invention binds to an antigen of human CD127 comprising the sequences of SEQ ID No: 115, SEQ ID No: 116 and SEQ ID No: 117.

In some embodiments, the antigen does not overlap with or does not comprise an epitope of IL-7R that is recognized by a monoclonal antibody selected from the group consisting of C1GM, C2M3, P3A9, P4B3, P2D2, P2E11, HAL403a and HAL403b (described in WO 2011104687 A1). In some embodiments, the antibody is raised against an antigen or binds to an epitope which does not comprise any, or does not comprise some of residues I82, K84, K100, T105, and Y192 of interleukin-7 receptor alpha, in particular does not comprise K100 and/or does not comprise T105. In some embodiments, the antigen or epitope does not comprise K194, or does not comprise any or does not comprise all of the residues selected from the group consisting of residues D190, H191, and K194 of human IL-7R. In particular embodiments, the antigen or epitope comprises neither I82 nor K84, or comprises neither K100 nor T105, or does not comprise Y192, or comprises neither D190, H191, Y192 nor K194.

While CD127 is common to both the IL-7R and the TSLPR, it must be noted that an anti-CD127 antibody will not necessarily recognize (i.e. bind to in suitable conditions) CD127 in both contexts. Moreover, even if the antibody binds to CD127 both in the context of the IL-7R and the TSLPR, it will not necessarily have the same effect on the IL-7-IL-7R interaction and the TSLP-TSLPR interaction. It could, for example, prevent the binding of IL-7 to IL-7R and not the binding of TSLP to TSLPR. Furthermore, the binding of the antibody to either receptor may have different effects, beyond the different effects on ligand-receptor interaction. Indeed, the binding of the antibody might modify the conformation of the receptor, independently of the ligand or in combination with the ligand, and thereby activate or inactivate the receptor. The effect may be different for either receptor and it may actually be inverted: an antibody which inactivates the IL-7R may activate the TSLPR, and vice-versa.

As used herein, activating a receptor means triggering at least some of the biochemical changes that occur upon binding of the ligand to its receptor. These changes may include modification of the receptor structure (e.g. dimerization); phosphorylation of the receptor and recruitment and/or phosphorylation of receptor-bound proteins (such as Janus kinases, STAT transcription factors etc) and/or changes to the cellular localization of the receptor (e.g. receptor internalization). As used herein, deactivating a receptor means preventing, or reverting, at least some of the biochemical modifications associated with the binding of its ligand to the receptor. For instance, a receptor may be constitutively activated (i.e. activated even in the absence of a ligand) and deactivated in the presence of an agent such as the antibody of the invention. Alternatively, or additionally, ligand-induced activation may be completely, or partially, inhibited by deactivating the receptor. Deactivation may therefore occur, among other mechanisms, through preventing binding of the ligand (and subsequent "activation" events), and/or preventing structural changes associated with the binding of the ligand (e.g. dimerization) and/or modification of the cellular location of the receptor (e.g. the deactivating agent may trigger receptor internalization and/or degradation and thus prevent activation by the ligand).

Absence of Increased TSLP-Induced Dendritic Cell Maturation

Antibodies of the invention may bind CD127 in the TSLP receptor (i.e. may bind CD127 when it is in a complex with the CRLF2, forming the TSLP receptor). Therefore, the antibodies of the invention may interfere with TSLP-induced and/or TSLP receptor-mediated signaling.

The inventors have surprisingly found that existing antibodies directed against (or which recognize) CD127 in the TLSP receptor and which display some antagonism with TSLP-TSLPR interaction nevertheless increase the maturation of dendritic cells induced by TSLP: said maturation is higher in cells treated with TSLP and the antibodies than in cells treated with TSLP alone. These conventional antibodies increase TSLP-dependent dendritic cell maturation. In preferred embodiments, the antibodies or fragments of the invention do not synergize with TSLP for the maturation of immune cells, in particular dendritic cells. In other words, the antibodies of the invention do not increase the maturation of immune cells induced by TSLP. This effect is particularly desired on the maturation of dendritic cells.

It should be emphasized that the capacity of anti-CD127 antibodies to inhibit TSLP-induced production of TARC cannot be considered a valid predictor of a negative (or at least non-positive) effect of the antibodies on TSLP-induced signaling and its downstream consequences (in particular the maturation of dendritic cells). Indeed, as the inventors have discovered, even antibodies efficiently inhibiting TSLP-induced production of TARC may increase TSLP-dependent maturation of dendritic cells as measured by expression of CD40 or CD80 with the TSLPR.

TSLP-induced dendritic cell maturation can be measured by the expression of cell marker CD40 and/or CD80 (Inaba et al., 1995; Watanabe et al., 2005b) as a marker which is a determinant of the maturation of some immune cells, especially of the so-called TH-2 differentiation observed in some autoimmune diseases, asthma and transplantation. In particular embodiments, the increase in dendritic cell maturation induced by TSLP is assessed by determining an elevated expression of the cell surface marker(s) CD40 and/or CD80 in TSLPR-positive cells treated with TSLP and with the macromolecule of the invention compared with TSLPR-positive cells treated with TSLP alone.

In a particular embodiment, the macromolecules, in particular the antibodies or fragment thereof, which do not increase TSLP-induced dendritic cell maturation do not increase expression of CD80 by more than 25% when compared to stimulation with TSLP alone (without macromolecule). Preferably, the expression of CD80 is not increased by more than 20%, preferably not by more than 10% and even more preferably not by more than 5%. In a particular preferred embodiment, the expression of CD80 is not increased or is decreased in cells stimulated with TSLP and with the macromolecule when compared to cells stimulated with TSLP alone.

In a particular embodiment, the macromolecules which do not increase TSLP-induced dendritic cell maturation do not increase expression of CD40 by more than 50% when compared to stimulation with TSLP alone (without macromolecule). Preferably, the expression of CD40 is not increased by more than 25%, preferably not by more than 10% and even more preferably not by more than 5%. In a particular preferred embodiment, the expression of CD40 is not increased or is decreased in cells stimulated with TSLP and with the macromolecule when compared to cells stimulated with TSLP alone.

Measurement of dendritic cells maturation is also illustrated in the examples (see in particular Example 9) and can be performed according to any standard method known from the skilled person, in particular any method suitable to determine CD80 and/or CD40 expression on dendritic cells, as a marker of dendritic cell maturation.

In order to assay the properties of anti-CD127 antibodies with respect to absence of unwanted potentiation of TSLP signaling, cells expressing the TSLPR, such as mammalian pro B cells (such as BA/F3 cells illustrated herein), may be used.

Inhibition of IL7-Induced Expression of $\alpha 4$, $\beta 7$ and $\alpha 4/\beta 7$ Integrins In particular embodiments, the antibodies (or macromolecules) of the invention inhibit IL7-induced expression of $\alpha 4$, $\beta 7$ and $\alpha 4/\beta 7$ integrins in vitro. IL7-induced expression of $\alpha 4$, $\beta 7$ and $\alpha 4/\beta 7$ integrins, as used herein, designates either or both the increase in the level of expression of $\alpha 4$ and $\beta 7$ integrins and the increase in the number or ratio of T lymphocytes expressing $\alpha 4$, $\beta 7$ and/or $\alpha 4/\beta 7$ integrins.

The inhibition may be partial, i.e. the level of expression of α4, β7 and α4/β7 integrins in the presence of IL7 is increased over baseline level (i.e. the level with neither antibody nor IL7) in the presence of antibodies, but less than in the absence of antibodies; or the inhibition may be complete, i.e. the level of expression of α4, β7 and α4/β7 integrins in the presence of IL7 and of the antibody is no higher than baseline level.

In particular embodiments, the antibodies of the invention inhibit expression of α4, β7 and/or α4/β7 integrins in vitro, i.e. the level of expression of α4, β7 and/or α4/β7 integrins is lower in cells treated with antibodies (and with and/or without IL7) than in untreated cells (i.e. without antibody or IL7). The extent of inhibition may be dose-dependent. The inhibition of expression may be measured as set forth in the Examples section, which the skilled person may adapt e.g. to specific antibodies, antibody fragments or antigen-binding domains or other macromolecules disclosed herein and/or to specific disease models as needed.

In preferred embodiments, the antibodies (or macromolecules) of the invention inhibit expression of α4, β7 and/or α4/β7 integrins in vivo. As used herein, this expression means that (i) the expression of α4, β7 and/or α4/β7 integrins, (ii) the number and/or ratio of α4, β7 and/or α4/β7-positive T-lymphocytes and/or (iii) the engraftment of α4, β7 and/or α4/β7-positive T-lymphocytes is reduced in samples obtained from animals treated with antibodies relative to untreated animals. As used herein, engraftment designates the incorporation of grafted tissue or cells into the body of the host, a process which typically occurs over a time period of a few hours to a few days. In particular embodiments, the animal is a mammal, in particular a non-human mammal, especially a mouse. In particular embodiments, the animal is a human. In particular embodiments, the effect is observed on human lymphocytes injected in a recipient animal, preferably an immunodeficient mouse. In particular embodiments, two weeks after injection of human PBMC in immunodeficient mice, the average percentage of integrin β7-positive T cells is reduced by at least 25%, preferably by at least 50%, in antibody-treated mice relative to untreated mice. In particular embodiments, two weeks after injection of human PBMC in immunodeficient mice, the average percentage of integrin β7-positive engrafted T cells is reduced by at least 25%, preferably by at least 50%, and even more preferably at least 70% in antibody-treated mice relative to untreated mice. The effect of the antibody or macromolecule of the invention may be determined using the methods put forth in the Examples section, in particular Example 16 for the expression of α4/β7 integrins and engraftment, which the skilled person may adapt as needed e.g. to the specific antibody, fragment or antigen-binding domain thereof or other macromolecule and/or to a specific disease model.

Inhibitors of CD127 Internalization

Internalization is the cellular process by which a cell surface receptor such as CD127 is transported inside the cell cytoplasmic space (possibly in/at the surface of intracellular compartments or membranes) and thus is no longer accessible from the extracellular space, i.e. the internalized receptor may not be directly contacted by a ligand in the extracellular space. A ligand, whether a natural ligand of the receptor or any artificial ligand or other molecule bound to the receptor, may be internalized together with the receptor. Most receptors undergo constant internalization and their cell surface expression is maintained constant either through the replacement of internalized and degraded receptors by newly synthesized/maturated receptors or through direct recycling, i.e. transport of the internalized receptor back to the cell surface.

Some stimuli may lead to increased rate of internalization and/or decreased rate of replacement/recycling, thus leading to a net decrease in cell surface expression of the receptor. As used herein, IL7-induced internalization of CD127 designates the decrease of cell surface expression of CD127 induced by the presence of IL7 (or observed in the presence of IL-7) in the extracellular medium, as observed in vitro after a limited time of incubation in order to exclude longer-term effects such as transcriptional down-regulation. Said limited time is typically in the order of tens of minutes, preferably less than 2 hours, more preferably less than 1 hour and even more preferably 45 minutes or less, 30 minutes or less or 15 minutes or less.

In a preferred embodiment, the antibody of the invention inhibits the IL7-induced internalization of CD127. Thus, when incubated with the antibody of the invention, the presence of IL7 induces no decrease in the cell surface expression of CD127, or induces a less strong decrease in the cell surface expression of CD127 than cells incubated without antibodies. In particular embodiments, when incubated with antibodies of the invention, the level of CD127 cell surface expression when cells are incubated at 37° C. for 15 minutes with 5 ng/mL IL7 is at least 80%, preferably at least 90% of the cell surface expression level in cells incubated without IL7. In vitro, the cell surface expression is preferably measured after a limited time as indicated above. Besides, as most cellular internalization processes are inhibited at low temperature, the effect is usually best observed at physiological temperature, in particular 37° C. However, it is also contemplated to incubate cells at low temperature, in particular 4° C.

It is known that antibodies to a receptor may induce internalization of the receptor, meaning that the cell surface expression of the receptor is decreased in the presence of the antibody. This may arise in particular by inducing a change in the conformation of the receptor which mimics that induced by the natural, internalization-inducing, ligand, and this effect may depend on the epitope recognized by the antibodies. As used herein, 'an antibody induces the internalization of CD127' means that cells incubated in the presence of an antibody display decreased cell surface expression of CD127 compared to cells incubated in the absence of the antibody. Cell surface expression is preferably measured in vitro after a limited incubation time and in temperature conditions as mentioned above. In a preferred embodiment, the antibody of the invention does not induce the internalization of CD127. Thus, the cell surface expression of CD127 in cells incubated in the presence of the antibody is not reduced, or is not significantly reduced, relative to cell surface expression in cells incubated in otherwise identical conditions, but in the absence of the antibody. In particular embodiments, when incubated at 37° C. for 30 to 45 minutes in the presence of 50 ng/mL of antibody, the level of CD127 cell surface expression is at least 80%, preferably at least 90% of its level in cells incubated in the absence of the antibody. This effect may be observed in the absence of IL7 (in both antibody-treated and -untreated cells), in the presence of IL7, and/or both.

Either of the two CD127 internalization-related feature described above (i.e. inhibition of IL7-induced internalization or non-induction of internalization) may contribute to increased efficiency of the antibodies, while the combination of both features is possibly even more efficient. Disclosed herein is an antibody representing a preferred embodiment, wherein in the presence of both IL7 and said antibody, the cell surface expression of CD127 is not significantly decreased. In such preferred embodiments, after a 45-minute incubation in the presence of 50 ng/mL of antibody, including 15 minutes in the presence of 5 ng/mL IL7, at 37° C., the level of CD127 cell surface expression is at least 80%, preferably at least 90% of its level in control cells, incubated in medium containing no antibody or IL7.

Disruption of CD127—γc Chain Interaction

According to a particular embodiment, the macromolecule, in particular an antibody or antigen-binding fragment thereof, of the invention may disrupt the binding of CD127 to the γc chain of the IL7-R. This means that, under conditions (in particular chemical and physical conditions) where CD127 and γc chain are bound together in the absence of antibody, and in particular in the presence of IL-7, the presence of the antibody significantly reduces said bond. In particular embodiments, in the presence of antibody and of IL-7, CD127 does not bind to γc. In particular, in the presence of the antibody and of IL-7, the amount of γc chain found associated with (or bound to) CD127 is less than 80%, preferably less than 50%, even more preferably less than 25% or 10% of the amount bound in the absence of the antibody (or in the presence of another anti CD-127 antibody such as MD707-13) in otherwise identical conditions, in particular in the presence of IL-7. Such a feature of the antibody may be assessed in particular by co-immunoprecipitation methods, well known to the skilled person for testing the interaction of proteins and illustrated herein in Example 21. In particular, cells may be incubated in the presence or absence of the tested antibody, then solubilized in conditions allowing for the preservation of protein complexes, and the resulting lysate may be subjected to an anti-CD127 immunoprecipitation and the presence of γc in the CD127-containing immunoprecipitated complex assessed by western blotting using anti-γc antibodies (conversely, the immunoprecipitation may be performed using anti-γc antibodies and the presence of CD127 assessed using anti-CD127 antibodies).

One method for obtaining such antibodies is to raise said antibodies against an epitope comprising sequences from the 2b site of CD127, or to select antibodies which recognize such an epitope. Indeed, the binding of the antibody to this site, critical for interaction with γc, is likely to disrupt, e.g. by competition or steric hindrance, the interaction of γc with CD127.

It is also possible, in particular, to select antibodies having this desirable feature, from anti-CD127 antibodies, e.g. from an antibody library (including when this library was not obtained by using an immunogen comprising sequences of the 2b site), through conventional screening procedures known to the skilled person and readily adaptable to such end. In particular, for example, CD127 (or its extracellular domain alone) may be bound to 96-well plates or similar substrates commonly used for such screening. The antibodies constituting the library may be added individually, each in one well, and the γc chain added to each well. After washing the plates, the presence of γc in each well may be tested, e.g. by methods based on fluorescence. In wells containing an antibody with the desired feature, no γc (or small amounts thereof) will be detected. It is obviously possible to modify this procedure, e.g. to rather spot the antibodies on a solid substrate in individual spots; allow CD127 to bind to the spotted antibodies, and allow γc chain to bind to the thus immobilized CD127 chains.

Antagonist Towards IL-7-IL-7R Interaction

According to a particular embodiment, a macromolecule, in particular an antibody or antigen-binding fragment thereof, of the invention further has antagonist properties toward interleukin 7 (IL-7) thereby antagonizing access, i.e. binding of IL-7 to CD127 on CD127 positive cells.

"Antagonist properties towards IL-7-IL-7R interaction" means that antibodies or antigen-binding fragments thereof of the invention, which target the IL-7Ralpha, have the effect of preventing the accessibility of the IL-7 receptor expressed on CD127 cells, especially human effector T cells, in particular human memory T cells, for its binding partner IL-7, especially human IL-7. As a result of antagonizing binding of IL-7, the antibodies of the invention or their functional fragments lead to lymphopenia by preventing IL-7-dependent thymic T cells generation.

The antagonist properties may be in particular antagonism toward IL-7R signaling induced by IL-7. An antagonist of IL-7R signaling induced by IL-7 can be identified by measuring the inhibition of STAT5 phosphorylation as described in the Examples. The IL7-induced phosphorylation of STAT5 is a marker of IL7R activation and an antibody antagonizing IL7-IL7R interaction is expected to decrease IL7-induced phosphorylation of STAT5.

In particular embodiments, the macromolecule of the invention is an antagonist of IL-7R signaling induced by IL-7. In a particular embodiment, the macromolecule of the invention inhibits IL7-induced phosphorylation of STAT5. In preferred embodiments, the inhibition of STAT5 phosphorylation is greater than 50% at antibody concentrations as low as 50 ng/ml and/or the inhibition of STAT5 phosphorylation is greater than 80% at antibody concentrations as low as 100 ng/ml. Inhibition of STAT5 phosphorylation may be assessed by methods known to the skilled person and in particular by the method set forth in the examples section (in particular Example 3).

"Antagonist for Binding of TSLP"

Since the antibodies of the invention bind CD127 in the IL-7R, they may also bind CD127 in the TSLPR and, particularly by steric hindrance and/or by competition on common binding sites, they may inhibit the binding of TSLP to the TSLPR. In other words, the antibodies of the invention may present antagonist activity for the binding of TSLP.

"Inhibitor of TSLP-Induced TARC Production"

In a particular embodiment, the antibodies of the invention may inhibit TSLP-induced TARC production of CD127-positive cells. As mentioned above, TSLP-stimulated dendritic cells produce elevated levels of TARC. This may result from their binding to the TSLPR and their potential action as antagonists of TSLP binding.

In a particular embodiment, the antibodies of the invention, and their antigen-binding fragments have been selected for their ability to not increase their maturation (maturation being e.g. determined an increased expression of CD40 and/or CD80 cell surface marker).

The level of TSLP-induced TARC production may be lower in cells treated with TSLP together with the anti-CD127 antibodies or fragments thereof or chimeric molecules as described herein than in cells treated with TSLP alone. In other words, the macromolecules of the invention may be inhibitors of TSLP-induced TARC production. In an embodiment of the invention, the antibody or fragment thereof or chimeric molecule as described herein decreases the levels of TARC production. In a particular embodiment of the invention, the level of TARC production in cells treated with TSLP and the antibody, fragment or chimeric molecule is reduced by more than 10%, preferably more than 20%, compared to the level in cells treated with TSLP alone, at antibody concentrations as low as 1 μg/ml. Measurement of TARC production is illustrated in the examples (in particular Example 9) and can be carried out on CD127-positive immune cells, in particular dendritic cells, from a blood sample using any standard method known from the skilled person.

"Cytotoxic Activity"

In a particular embodiment of the invention, the antibodies of the invention or their antigen-binding fragments directed against the CD127 molecule present in the IL-7 receptor have furthermore the property of being cytotoxic against human cells, especially human T cells expressing said receptor. Human cells expressing CD127 as a chain of IL-7 receptor, which are the target of the antibodies of the invention and fragments thereof, are mainly T lymphocytes and more precisely are subpopulations of effector T lymphocytes including naïve and memory T cells but are not regulatory T cells (Treg), especially not resting natural Treg. Memory T cells are generated as a result of antigen priming and mainly defined by their functional characteristics, including ability to undergo recall proliferation upon re-activation and differentiation into secondary effector and memory cells. Similarly, the targeted TSLP receptor (as a complex including the IL-7-R alpha chain) regulates T helper lymphocyte, B cell and dendritic cell differentiation.

According to an embodiment of the invention, the antibodies and antigen-binding fragments thereof, having "cytotoxic activity against T cells" or cytotoxic properties (cytotoxic antibodies) give rise to depletion in the effector T cell population by killing these cells and accordingly reduce the number of these cells when administered. To the contrary, these antibodies do not alter the subpopulation of regulatory T cells or do not alter it to a significant extent, allowing the Treg cells to perform their function. In this context, in a particular embodiment, it has been observed that the ratio of regulatory T (Treg) versus effector T (Teff) cells raises following administration of antibodies of the invention. In a particular embodiment, antibodies of the invention enable to raise said ratio of about 10% or more. In a particular embodiment, the increase in the ratio of Treg versus Teff is of about 20%.

According to a particular embodiment of the invention, the cytotoxic antibodies show Antibody-Dependant Cellular Cytotoxicity (ADCC). According to another embodiment, the antibodies of the invention have no ADCC properties. Antibody ADCC potential was considered positive when specific cytoxicity was superior to 10%. ADCC properties can be evaluated in an ADCC assay such as the test described in the Examples (in particular Example 10). When the antibody is a rat antibody the effector cells used in the ADCC assay are LAK (Lymphokine-activated killer) cells of rat. When the antibodies are humanized the ADCC assay can be carried out on human NK cells.

The antibodies of the invention which have both cytotoxic and antagonist properties for CD127 positive cells enable cumulative effects of these properties with respect to the depletion of effector T cells, especially of memory T cells especially, thereby enabling a stronger depletion (exhaustion of the pool of CD127+ cells) and corresponding reduction in the number of target T cells.

The paragraphs above as well as the Examples describe how to test for these functional characteristics. The following sections will detail various structural characteristics and possible modifications of the antibodies or fragments or chimeric molecules. In light of these guidances, the skilled person will be able to obtain antibodies or fragments having the structural characteristics below along with the desired functional characteristics, in particular starting from an antibody which has the desired functional characteristics, such as N13B2, because in some cases it can be predicted that adopting some of the structural features will not modify the functional features and/or by testing for the loss of functional characteristics after the introduction of a new structural characteristic. Furthermore, with the disclosure herein of the epitope recognized by the antibody, the development of other antibodies sharing the same functional features is a routine procedure, since antibodies raised against the same or a similar epitope could be selected for their ability to provoke similar effects upon binding to CD127. Again, straightforward testing procedures being disclosed herein, the skilled person may use these tests to select suitable antibodies.

In a preferred embodiment of the invention, the macromolecule is N13B2 or an antibody having at least one of the CDRs of N13B2, or the fragments are fragments of N13B2. Accordingly, the invention relates to an antibody or fragment thereof which VH comprises at least one of the following amino acid sequences, or one of their preferable humanized variants described below:

VHCDR1 SEQ ID No:10;
VHCDR2 SEQ ID No:12;
VHCDR3 SEQ ID No:14;

and/or which VL comprises at least one of the following amino acid sequences, or one of their preferable humanized variants described below:

VLCDR1 SEQ ID No:16;
VLCDR2 SEQ ID No:18;
VLCDR3 SEQ ID No:20.

In a particular embodiment, the macromolecule comprises at least 2, 3, 4 or 5 of the CDR sequences of N13B2 i.e. VHCDR1 SEQ ID No:10, VHCDR2 SEQ ID No:12, VHCDR3 SEQ ID No:14, VLCDR1 SEQ ID No:16, VLCDR2 SEQ ID No:18 and VLCDR3 SEQ ID No:20, any number of which may be replaced by one of their preferable humanized variants described below. In a particular embodiment, the macromolecule comprises all six CDR sequences of N13B2, any number of which may be replaced by one of their preferable humanized variants described below. In particular embodiments, the macromolecule comprises the VH chain having the amino acid sequence of SEQ ID No:22 and/or the VL chain having the amino acid sequence of SEQ ID No:24. In particular embodiments, the macromolecule comprises the heavy chain having the amino acid acid sequence of SEQ ID No:2 and/or of SEQ ID No:6 and/or the light chain having the amino acid sequence of SEQ ID No:4. Other particular embodiments relative to the VH and VL chains are humanized variants disclosed below. In a particular embodiment, the constant chain has the sequence of the rat IgG1 Fc chain of FIG. 12 (Uniprot P20759) and/or the sequence of SEQ ID No:34.

Fragments

An "antigen-binding fragment" of an antibody of the invention is a part of the antibody, i.e. a molecule corresponding to a portion of the structure of the antibody of the invention that exhibits antigen-binding capacity for alpha chain of the IL-7 receptor for human IL-7, possibly in its native form; such fragment especially exhibits the same or substantially the same antigen-binding specificity for said antigen compared to the antigen-binding specificity of the corresponding four-chain antibody. Advantageously, the antigen-binding fragments have a similar binding affinity as the corresponding 4-chain antibodies. However, antigen-binding fragment that have a reduced antigen-binding affinity with respect to corresponding 4-chain antibodies are also encompassed within the invention. The antigen-binding capacity can be determined by measuring the affinity of the antibody and of the considered fragment. These antigen-binding fragments may also be designated as functional fragments of antibodies.

Antigen-binding fragments of antibodies are fragments which comprise their hypervariable domains designated CDRs (Complementary Determining Regions) or part(s) thereof encompassing the recognition site for the antigen, i.e., IL-7Ra of human IL-7, thereby defining antigen recognition specificity. Each Light and Heavy chain (respectively VL and VH) of a four-chain immunoglobulin has three CDRs, designated VL-CDR1, VL-CDR2, VL-CDR3 and VH-CDR1, VH-CDR2, VH-CDR3, respectively. Thus the invention relates in particular to fragments of antibodies of the invention, which comprise or consist in all or a selection of CDRs among VL-CDR1 (SEQ ID No:16), VL-CDR2 (SEQ ID No:18), VL-CDR3 (SEQ ID No:20) and VH-CDR1 (SEQ ID No:10), VH-CDR2 (SEQ ID No:12) and VH-CDR3 (SEQ ID No:14), their humanized variants disclosed below, or functional portions thereof, i.e. portions that exhibit the desired binding specificity preferably with a high affinity for IL-7Ra of human IL-7.

Particular antigen-binding fragments of the invention are fragments of the VH chain of an antibody of the invention that combine its CDR1, CDR2 and CDR3 domains, in particular those having the amino acid sequence disclosed herein, including the humanized variants disclosed below. Other fragments of the invention are fragments of the VL chain of an antibody of the invention that combine its CDR1, CDR2 and CDR3 domains, in particular those having the amino acid sequence disclosed herein, including the humanized variants disclosed below. Fragments that comprise or consist in VH-CDR3 and/or VL-CDR3, in particular those having the amino acid sequence disclosed herein, including the humanized variants disclosed below, or functional portions thereof are especially preferred when CDR3 regions appear to be determinant in antigen recognition specificity.

The skilled person will be able to determine the location of the various regions/domains of antibodies by reference to the standard definitions in this respect set forth, including a reference numbering system (Martin, 2001) or by reference to the numbering system of Kabat (Kabat et al., 1992) or by application of the IMGT "collier de perle" algorithm (http://www.imgt.org/IMGTindex/Colliers.html, Lefranc et al., 1999). In this respect, for the definition of the sequences of the invention, it is noted that the delimitation of the regions/domains may vary from one reference system to another. Accordingly, the regions/domains as defined in the present invention encompass sequences showing variations in length or localization of the concerned sequences within the full-length sequence of the variable domains of the antibodies, of approximately +/−10%.

In addition, de-immunization residues may be present in the variable CDR domains of the antibodies or antigen-binding fragments thereof. In a particular embodiment, the antibody or fragment thereof is deimmunized.

Based on the structure of four-chain immunoglobulins, antigen-binding fragments can thus be defined by comparison with sequences of antibodies in the available databases and prior art (Martin, 2001), and especially by comparison of the location of the functional domains in these sequences, noting that the positions of the framework and constant domains are well defined for various classes of antibodies, especially for IgGs, in particular for mammalian IgGs. Such comparison also involves data relating to 3-dimensional structures of antibodies.

For illustration purpose of specific embodiments of the invention, antigen-binding fragments of an antibody that contain the variable domains comprising the CDRs of said antibody encompass Fv, dsFv, scFv, Fab, Fab', F(ab')2 which are well defined with reference to (Kabat et al., 1992), (Martin, 2001) and also (Delves et al., 2011) Fv fragments consist of the VL and VH domains of an antibody associated together by hydrophobic interactions; in dsFv fragments, the VH:VL heterodimer is stabilised by a disulphide bond; in scFv fragments, the VL and VH domains are connected to one another via a flexible peptide linker thus forming a single-chain protein. Fab fragments are monomeric fragments obtainable by papain digestion of an antibody; they comprise the entire L chain, and a VH-CH1 fragment of the H chain, bound together through a disulfide bond. The F(ab')2 fragment can be produced by pepsin digestion of an antibody below the hinge disulfide; it comprises two Fab' fragments, and additionally a portion of the hinge region of the immunoglobulin molecule. The Fab' fragments are obtainable from F(ab')2 fragments by cutting a disulfide bond in the hinge region. F(ab')2 fragments are divalent, i.e. they comprise two antigen-binding sites, like the native immunoglobulin molecule; on the other hand, Fv (a VH-VL dimmer constituting the variable part of Fab), dsFv, scFv, Fab, and Fab' fragments are monovalent, i.e. they comprise a single antigen-binding site.

Chimeric Antibodies

According to another embodiment of the invention, the antibodies are modified and are, as a result, chimeric antibodies, comprising domains or strand(s) of amino acid residues of different antibodies, in particular antibodies obtained from different animal species, combined together in a functional antibody. In a particular embodiment, the macromolecule of the invention is a chimeric antibody consisting in an assembly of antibody fragments from at least two different species. In a particular embodiment, a chimeric antibody comprises the constant region of a human antibody. Such constant regions are illustrated in the examples by Fc fragments G1 (SEQ ID No:26) or Fc fragments G4 (SEQ ID No:28) or CL kappa fragment (SEQ ID No:30). Alternatively, human Fc fragments depicted in FIG. 12 (Uniprot P01857, Uniprot P01859, Uniprot P01861) and/or with the sequences of SEQ ID No:31, SEQ ID No:32, SEQ ID No:33 or SEQ ID No:112 may be used. In a particular embodiment, a chimeric antibody comprises the variable region of a rodent antibody and the constant region of a human antibody. In a particular embodiment, a chimeric antibody comprises the VH chain with the sequence of SEQ ID No:2 (N13B2-G1m-VH-FcG1m(E333A)) or the sequence of SEQ ID No:6 (N13B2-G4m-VH-FcG4m (S228P)) and the VL chain with the sequence of SEQ ID No:4 (N13B2-G1m-VL-CLkappa).

Affitins, Anticalins and Other Antibody Mimetics

Macromolecules of the invention also comprise artificial proteins with the capacity to bind antigens mimicking that of antibodies, also termed herein antigen-binding antibody mimetic. Such proteins comprise affitins and anticalins. Affitins are artificial proteins with the ability to selectively bind antigens. They are structurally derived from the DNA binding protein Sac7d, found in *Sulfolobus acidocaldarius*, a microorganism belonging to the archaeal domain. By randomizing the amino acids on the binding surface of Sac7d, e.g. by generating variants corresponding to random substitutions of 11 residues of the binding interface of Sac7d, an affitin library may be generated and subjecting the resulting protein library to rounds of ribosome display, the affinity can be directed towards various targets, such as peptides, proteins, viruses and bacteria. Affitins are antibody mimetics and are being developed as tools in biotechnology. They have also been used as specific inhibitors for various enzymes (Krehenbrink et al., 2008). The skilled person may readily develop affitins with the required binding properties using methods know in the art, in particular as disclosed in patent application WO2008068637 and the above-cited publication, in particular the generation of phage display and/or ribosome display libraries and their screening using an antigen as disclosed herein. Anticalins are artificial proteins that are able to bind to antigens, either to proteins or to small molecules. They are antibody mimetic derived from human lipocalins which are a family of naturally binding proteins. Anticalins are about eight times smaller with a size of about 180 amino acids and a mass of about 20 kDa (Skerra, 2008). Anticalin phage display libraries have been generated which allow for the screening and selection, in particular of anticalins with specific binding properties. The skilled person may readily develop affitins with the required binding properties using methods know in the art, in particular as disclosed in EP patent EP1270725 B1, U.S. Pat. No. 8,536, 307 B2, (Schlehuber and Skerra, 2002) and the above-cited publication, in particular the generation of phage display and/or ribosome display libraries and their screening using an antigen as disclosed herein. Anticalins and affitins may be both be produces in a number of expression system comprising bacterial express in systems. Thus, the invention provides affitins, anticalins and other similar antibody mimetics with the features of the antibodies described herein, in particular with regard to binding to CD127, non-induction and/or inhibition of CD127 internalization, maturation of DCs, all of which are contemplated as macromolecules of the invention. Humanization In a particular embodiment, the macromolecules of the invention are humanized antibodies or antigen-binding fragments thereof. Accordingly having been originally obtained in animals, especially in rodents and in particular in rats, following immunization of animals and production of monoclonal antibodies from hybridoma, the antibodies of the invention are modified in their VH and/or VL sequences by substitution of amino acid residues, in the framework and optionally in addition in the CDR sequences. The humanization can be performed by resurfacing or by CDR grafting according to known techniques. Resurfacing is especially achieved by the substitution of rodent residues for human amino acid residues. The substitution is performed in a way that maintains the framework structure of the original antibody and also the CDRs presentation, thereby enabling that the frameworks and CDRs interactions in the resurfaced antibody preserve native conformation of the surface contacting the antigen so that it retains antigen binding affinity.

Preferred embodiments of the antibody of the invention are represented by the humanized versions of the (rat) N13B2 antibody comprising the following light and heavy chains:

The heavy chain of N13B2-h1, having the sequence of SEQ ID No: 36, wherein the CDR sequences of the rat N13B2 have been conserved, as well as a few other amino acids outside the CDR sequences, and wherein all other amino acids match the sequence of a human antibody. This heavy chain has 87.8% identity with a human antibody heavy chain. The following residues outside the CDR sequences have been conserved: V at Kabat position H24 (position 24 in FIG. 23; A in the human sequence), V at Kabat position H37 (position 37 in FIG. 23; I in the human sequence), A at Kabat position H49 (position 49 in FIG. 23; S in the human sequence) and D at Kabat position H73 (position 74 in FIG. 23; N in the human sequence);

The heavy chain of N13B2-h2, having the sequence of SEQ ID No: 38, wherein, compared with the heavy chain of N13B2-h1, amino acids at Kabat positions H37, H49 and H73, outside the CDR sequences, have been modified to match the sequence of a human antibody heavy chain;

The heavy chain of N13B2-h3, having the sequence of SEQ ID No: 40, wherein, compared with the heavy chain of N13B2-h2, the M at Kabat position H96 (position 100 in FIG. 23), within the CDR3 sequence, has been mutated to L to match the sequence of a human antibody heavy chain and/or to avoid post-translational modification. Other possible residues for this position include in particular A, F and I and more preferably F or I. Accordingly, a possible humanized variant for the CDR3 sequence of N13B2 VH has the sequence of SEQ ID No: 48.

The light chain of N13B2-h1, having the sequence of SEQ ID No: 42, wherein the CDR sequences of the rat N13B2 have been conserved, as well as a few other amino acids outside the CDR sequences, and wherein all other amino acids match the sequence of a human antibody. This light chain has 80% identity with a human antibody light chain. The following residues outside the CDR sequences have been conserved: V at Kabat position L48 (position 48 in FIG. 24; I in the human sequence), Y at Kabat position L71 (position 71 in FIG. 24; F in the human sequence) and F at Kabat position L87 (position 87 in FIG. 24; Y in the human sequence);

The light chain of N13B2-h2, having the sequence of SEQ ID No: 44, wherein, compared with the light chain of N13B2-h1, the three amino acids at Kabat positions L48, L71 and L87, outside the CDR sequences, have been modified to match the sequence of a human antibody light chain;

The light chain of N13B2-h3, having the sequence of SEQ ID No: 46, wherein, compared with the light chain of N13B2-h2, amino acids Kabat positions L31 (position 31 in FIG. 24) and/or L52 (position 53 in FIG. 24), within the CDR1 and CDR2 sequences respectively, have been mutated from N to Q and from S to T respectively, to match the sequence of a human antibody light chain and/or to avoid post-translational modification. Other possible amino acids for the L31 position include H and R. Other possible mutations for the CDR3 sequence involve conserving the S in position L52 and mutating the N in position L51 (position 52 in FIG. 24) to Q, H, K or R. Accordingly, a possible humanized variant for the CDR1 sequence of N13B2 VL has the sequence of SEQ ID No: 50, and a possible humanized variant for the CDR2 sequence of N13B2 VL has the sequence of SEQ ID No: 52.

Multi-Functional Antibodies or Fragments

These basic antigen-binding fragments of the invention can be combined together to obtain multivalent antigen-binding fragments, such as diabodies, tribodies or tetrabodies. These multivalent antigen-binding fragments are also part of the present invention.

The above-mentioned modifications may be combined where relevant. In particular embodiments, the macromolecule is an antibody which is a chimeric antibody or an humanized antibody and/or a deimmunized antibody.

Methods of Obtaining Antibodies of the Invention

An antibody or an antigen-binding fragment thereof of the invention is in particular advantageously raised against a molecule which is the CD127 expressed by human T cells, possibly raised from an immunization under the form of native polypeptide or recombinant molecule.

Immunization can be carried out according to the protocol disclosed in the Examples below: Recombinant CD127 Fc Chimera (10975-H03H Sino Biological, Beijing, China) was used to immunize rats such as rats of the LOU/C Igk1a strain available at the University of Louvain, Belgium). Alternatively, an antigen comprising the amino acid sequences of SEQ ID No:115 (in particular comprising SEQ ID No: 110) and/or of SEQ ID No:117 (in particular comprising SEQ ID No: 111) and/or of SEQ ID No:116, said antigen additionally comprising other sequences, in particular other sequences of human CD127, or not, as disclosed above,_may be used as the immunogen. Hybridoma were obtained by fusing spleen mononuclear cells with the LOU rat immunocytoma IR983F, a non-secreting and azaguanine resistant cell line, according to a previously described procedure (Chassoux et al., 1988). Hybridoma were first screened according to the capacity of the secreted monoclonal antibodies to bind to recombinant CD127 molecule (CD127 Fc Chimera; 10975-H03H, Sino Biological, Beijing, China). Hybridoma were then screened for the capacity of their monoclonal antibodies to bind to the CD127 expressed by human T cells and for the capacity to inhibit induction of STAT-5 phosphorylation induced by IL-7 on human leukocytes, as exemplified in FIG. 1, and for their capacity not to increase the maturation of dendritic cells induced by TSLP.

According to a particular embodiment of the invention, a humanized antibody of the invention is derived from the antibody designated N13B2 by mutation of one or more of the CDR region(s) of its Variable Heavy chain (VH) and/or of its Variable Light chain (VL), in particular an antibody keeping at least one or two original CDR region among CDR3, CDR2 and CDR1 regions in either of VH and/or VL, said modified antibody having less than 10% of mutated amino acid residues, preferably one or no mutated amino acid residue, in individually considered CDR regions with respect to the original CDR1, CDR2 or CDR3 region, wherein said original CDR regions are
  i. VHCDR1 having the amino acid sequence SEQ ID No 10;
  ii. VHCDR2 having the amino acid sequence SEQ ID No 12;
  iii. VHCDR3 having the amino acid sequence SEQ ID No 14;
  iv. VLCDR1 having the amino acid sequence SEQ ID No:16;
  v. VLCDR2 having the amino acid sequence SEQ ID No:18;
  vi. VLCDR3 having the amino acid sequence SEQ ID No:20;

Accordingly, the VHCDR3 may have the amino acid sequence of SEQ ID No: 48; the VLCDR1 may have the amino acid sequence of SEQ ID No: 50; the VLCDR2 may have the amino acid sequence of SEQ ID No: 52.

In a particular embodiment, an antigen-binding fragment of the invention is an antigen-binding fragment of the N13B2 antibody which is modified as described in the previous paragraphs, said modified antigen-binding fragment having less than 10% of mutated amino acid residues with respect to the original antigen-binding fragment.

In view of the teaching provided by the present invention, in order to express antibodies of the invention, the skilled person will be able to prepare hybridoma or to use alternative technologies such as expression libraries and expression systems, followed by selection of antibodies having the structure of those secreted by the hybridoma and having its properties, in particular its binding and neutralisation properties. cDNA libraries can adequately be prepared from the RNA expressed in hybridoma of the invention and the appropriate sequences selected and expressed. Alternatively, cDNA encoding the antibodies of the invention or their fragments are prepared by synthesis.

"Hybridoma cells" according to the invention are cells generated from fusion of antibody producing cells (B Lymphocytes) from an animal previously immunized with a selected immunogen and fusion partner which are myeloma cells enabling to provide immortality to the resulting fusion cell. Myeloma cells and antibody producing cells (B cells such as splenocytes) can be of the same origin, and are eukaryotic cells in particular mammalian cells of the same animal. They can be alternatively of different origin, thus giving rise to a heterohybridoma. Myeloma cells such as the LOU rat immunocytoma IR983F, a non-secreting and azaguanine resistant cell line are chosen among cells that fail to produce immunoglobulins in order to enable the prepared hybridoma to secrete only monoclonal antibodies of the desired specificity. Other cells suitable for promoting ADCC such as those described in the following pages for the preparation of the antibodies through expression in recombinant cells may be used instead of the rat immunocytoma. Such cells are advantageously cells having a low or no fucosylation capacity.

Preparation of hybridoma suitable for carrying out the invention is performed according to conventional techniques. Embodiments are described in detail in the Examples of the present application of which the particular disclosed features can be adapted to other cells used as fusion partners.

The antigen-binding fragments of the antibody may be obtained starting from the antibody, especially by using enzymatic digestion according to well-known techniques including papain or pepsin digestion, or using any appropriate cleavage technique. They may be alternatively expressed in host cells modified by recombination with nucleic acid sequences encoding the amino acid sequence of said fragments, or may be synthesized, especially chemically synthesized. Accordingly, the antibodies of the invention, including the modified antibodies and the antigen-binging fragments of the antibodies can also be prepared by classical genetic engineering techniques, such as those described by Sambrook et al. (Deininger, 1990) and updated versions). The invention accordingly relates to the versions of the VH and VL polypeptides that encompass the signal peptide or not. The signal peptide may be necessary during the preparation of the polypeptides in cells.

With a view to use the antibody of the invention or their functional fragments for administration to a human patient, it might be beneficial to derive humanized monoclonal antibodies or chimeric monoclonal antibodies and/or de-immunized antibodies, from antibodies of the invention which would be non-primate antibodies such as those illustrated in the Examples, especially to lower the immune reaction of the receiving host or patient against said antibodies. Functional fragments of these variant antibodies may be obtained also as humanized, chimeric or de-immunized variants.

An antibody or an antigen-binding fragment thereof, which is a humanized antibody can also be derived by substitution of amino acid residue(s) present in constant region(s) of variable chains (VH and/or VL) of a non-human antibody of the invention, for human amino acid residue(s) having corresponding location in human antibodies according to standard definition and numbering, wherein the substitution level is from 1% to 20%, in particular from 1% to 18% of the residues in said framework regions. Said constant regions include those of framework regions (FwRs) defined in four-chain antibodies identified in particular by reference to Kabat numbering.

Particular examples of modified antibodies according to the invention encompass chimeric antibodies, humanized antibodies and/or a de-immunized antibodies.

A particular modified antibody has modified amino acid residues in the CDRs regions, said modification resulting in a de-immunisation by loss of the T cell epitopes in the variable domain of the non-human antibody. De-immunisation can be performed after determination of the T cell epitopes in the antibody variable domain, especially by in silico prediction, followed by point mutation in the sequence of the variable chains of the antibody that eliminates the functional T cell epitopes. In a preferred embodiment of the invention, the modification of the CDR(s) regions, especially of the CDR3 regions are limited to the extent necessary to de-immunisation with a view to administration to the human body, e.g. to decrease binding affinity of T cell receptors for HLA-class II/peptide complexes. In a particular embodiment, the CDR3 region(s) of the VH and/or of the VL is(are) not modified. In another embodiment the FR regions and/or the CH regions are also modified, especially humanized.

Antibodies within the frame of the invention encompass accordingly an antibody based on the above defined features, which is a humanized antibody especially one obtained by substitution of amino acid residue(s) present in framework region(s) of an antibody of the invention, for human amino acid residue(s) having corresponding location in human antibodies according to standard definition and numbering. The substitution level of amino acid residues in the framework regions and/or in the CDRs for humanization, including de-immunisation, is from 1% to 20% in particular from 1% to 18% of the residues in said framework regions and/or CDRs regions. As mentioned above, the humanization primarily targets the Framework regions of the original antibodies. In some cases, humanization may alternatively or also concern CDR region(s) especially CDR1 and/or CDR2 region(s) and is more particularly designated as de-immunisation. In particular embodiments, no more than one amino acid is modified in each CDR region. Examples of humanized and/or deimmunized antibodies derived from the rat antibody N13B2 are disclosed herein.

Humanization can hence be achieved considering the human germline Light chain or Heavy chain frameworks that show the highest sequence identity with the sequence of the non-human antibody or fragment, and selecting the amino acid residues, especially residues exposed at the surface in the antibody, to be substituted in said non-human antibody or fragment thereof, in order to conform to the corresponding human residue(s). In a particular embodiment some of or all the FRL and/or some of or all the FRH regions are fully human, i.e., are characteristic of human framework sequences. In another embodiment selected residues in some or all the FR regions are substituted.

Methods for humanizing antibodies are also well known in the art and are described for instance by Routledege et al. (Edward G. Routledge, 1993). These methods can also apply to antigen-binding fragments, such as scFvs. By way of example, the method known as "resurfacing" consists in replacing the set of surface residues in the frameworks of the variable region of a nonhuman antibody with a human set of surface residues, while the method known as CDR grafting consists of transferring the CDRs from a non-human antibody into the framework regions of a human antibody. CDR grafting is generally completed by framework optimization, consisting in the replacement of some residues of the human framework, in order to optimize the binding affinity. The step of framework optimization has been recently simplified by the use of combinatorial libraries (Rosok et al., 1996) (Baca et al., 1997).

The invention relates in particular to humanized antibodies derived by CDR grafting from the rat N13B2 antibody. Human VH and VL sequences having sequences with strong homology to the VH and VL sequences, respectively, of rat N13B2 were selected in a database. The CDR sequences of N13B2 were grafted onto these human sequences. Some residues outside the CDR sequences might have a significant impact on antigen recognition or affinity, in particular residues in immediate proximity to the CDRs and residues known as Vernier residues. As detailed above and in the Examples section, in particular in Example 12, several versions of the humanized antibodies were tested: the most conservative where all rat sequences were conserved for the CDR and the above-mentioned structurally important residues, a version where human sequences were selected for the structurally important residues and the version closest to the human sequences, where, in addition to the structurally important residues outside the CDR, a few residues inside the CDR were modified from the initial rat sequence in order in particular to prevent post translational modifications such as oxidation or deamidation.

Another recent strategy available for antibody humanization preserves only the original nonhuman CDR3 sequences of light and heavy chains while the remaining sequence is selected from naïve human V gene libraries (Rader et al., 1998).

The chimeric, humanized and/or de-immunized antibodies of the invention can belong to any class of immunoglobulins, like the non-modified antibodies. Preferably, they belong to a subclass of the IgG class such as IgG1, IgG2, IgG3 or IgG4.

Methods for preparing recombinant antigen-binding fragments, or chimeric antibodies by combining the variable regions of an antibody with appropriate linkers, or with the constant regions of another antibody, are well known in the art.

The antibodies of the invention are said to be monoclonal antibodies, meaning that a composition of these antibodies is homogeneous, especially identical, in terms of antigen-binding specificity and accordingly in terms of variable region composition. Hence the antibodies may qualify as monoclonal even if they are obtained by techniques alternative to the technique of hybridoma.

According to another embodiment, the invention also relates to a chimeric molecule which comprises an antibody according to any of the definition provided herein or an antigen-binding fragment thereof, wherein said antibody or functional fragment thereof is associated with a functionally different molecule. A chimeric molecule of the invention may be either a fusion chimeric protein or a conjugate resulting from any suitable form of attachment including covalent attachment, grafting, chemical bonding with a chemical or biological group or with a molecule, such as a PEG polymer or another protective group or molecule suitable for protection against proteases cleavage in vivo, for improvement of stability and/or half-life of the antibody or functional fragment. With similar techniques, especially by chemical coupling or grafting, a chimeric molecule can be prepared with a biologically active molecule said active molecule being for example chosen among toxins, in particular Pseudomonas exotoxin A (Risberg et al., 2011), the A-chain of plant toxin ricin (van Oosterhout et al., 2001) or saporintoxin (Flavell et al., 2006), especially a therapeutic active ingredient, a vector (including especially a protein vector) suitable for targeting the antibody or functional fragment to specific cells or tissues of the human body, or it may be associated with a label or with a linker, especially when fragments of the antibody are used.

PEGylation of the antibody or functional fragments thereof is a particular interesting embodiment as it improves the delivery conditions of the active substance to the host, especially for a therapeutic application. PEGylation can be site specific to prevent interference with the recognition sites of the antibodies or functional fragments, and can be performed with high molecular weight PEG. PEGylation can be achieved through free Cysteine residues present in the sequence of the antibody or functional fragment or through added free Cysteine residues in the amino sequence of the antibody or functional fragment.

The invention concerns also a composition comprising antibodies or functional fragments thereof as defined herein, wherein the antibodies or functional fragments thereof are a homogeneous population of antibodies or functional fragments thereof or are monoclonal antibodies or functional fragments thereof.

In some cases it is possible to use a composition of products to obtain the desired effect, where each of the products in the composition generates at least one desired effect. In the present case, for example, it is possible to combine molecules having an inhibitory effect on the IL-7-IL-7R interaction and molecules having cytotoxic effect against CD127 positive cells. Such combinations are included in the invention. Importantly, in the invention, the composition of products should not synergize with TSLP for the maturation of dendritic cells. Usually, this involves combining products of which none individually synergizes with TSLP for the maturation of dendritic cells.

In a particular embodiment, the invention concerns a composition or an assembly of compounds comprising antibodies, fragments or chimeric molecules as described herein, said composition comprising (i) a population of antibodies or antigen-binding fragments thereof or chimeric molecules having cytotoxic activity against CD127 positive cells, especially CD127+ T cells and (ii) a population of antibodies or functional fragments thereof or chimeric molecules having antagonist properties towards human IL-7, these populations of antibodies being either combined in a mixture or separated and, in this latter option, formulated for combined or sequential administration. The antibodies and/or functional fragments and/or chimeric molecules do not synergize with TSLP for the maturation of dendritic cells.

The definitions provided herein especially by reference to the antibodies of the invention, similarly apply to the antigen-binding fragments thereof except where it is technically obviously not relevant. These definitions also apply to macromolecules (in particular chimeric antibodies or chimeric molecules) or compositions comprising these antibodies or antigen-binding fragments thereof or derived from these antibodies, as disclosed in the present application. It is further specified that the antigen-binding fragments of the antibodies of the invention are derived from the antibodies from a conceptual or design point of view but may be prepared through various techniques, not necessarily having recourse to the antibodies as products.

The invention also relates to a nucleic acid molecule encoding a macromolecule according to any of the definitions provided herein. In particular embodiments, the nucleic acid of the invention encodes an amino acid chosen from the group consisting of SEQ ID No:2; SEQ ID No:4; SEQ ID No:6; SEQ ID No:8; SEQ ID No:10; SEQ ID No:12; SEQ ID No:14; SEQ ID No:16; SEQ ID No:18; SEQ ID No:20; SEQ ID No:22, SEQ ID No:24, SEQ ID No:36, SEQ ID No:38, SEQ ID No:40, SEQ ID No:42, SEQ ID No:44, SEQ ID No:46, SEQ ID No:48, SEQ ID No:50, SEQ ID No:52, SEQ ID No:54, SEQ ID No:56, SEQ ID No:110, SEQ ID No:111, SEQ ID No:86, SEQ ID No:115, SEQ ID No:116 and SEQ ID No:117. In particular embodiments, the nucleic acid of the invention comprises or consists in the sequence of SEQ ID No: 1, 3, 5, 7, 9, 11, 13, 15, 17, 19, 21, 23, 35, 37, 39, 41, 43, 45, 47, 49, 51, 53 or 55.

Such a nucleic acid suitable for the preparation of macromolecules of the invention is especially chosen in the group of:

i. a polynucleotide encoding a VH region and having the sequence of SEQ ID No 1 or SEQ ID No: 5 or SEQ ID No:54 or the variable region of a VH region and having the sequence of SEQ ID No:21 or SEQ ID No: 35 or SEQ ID No:37 or SEQ ID No:39;

ii. a polynucleotide encoding a VL region having the sequence of SEQ ID No 3 or SEQ ID No: 7 or SEQ ID No:56 or the variable region of a VL region and having the sequence of SEQ ID No:23, or SEQ ID No: 41 or SEQ ID No:43 or SEQ ID No:45;

iii. a polynucleotide encoding a VHCDR1 region having the sequence of SEQ ID No:9, iv. a polynucleotide encoding a VHCDR2 region having the sequence of SEQ ID No:11, v. a polynucleotide encoding a VHCDR3 region having the sequence of SEQ ID No:13 or of SEQ ID No:47, vi. a polynucleotide encoding a VLCDR1 region having the sequence of SEQ ID No 15 or of SEQ ID No:49, vii. a polynucleotide encoding a VLCDR2 region having the sequence of SEQ ID No 17 or of SEQ ID No:51, viii. a polynucleotide encoding a VLCDR3 region having the sequence of SEQ ID No 19.

The invention also relates to a polynucleotide having modified nucleotides with respect to the sequence of SEQ ID No 1, 3, 5, 7, 9, 11, 13, 15, 17, 19, 21, 23, 35, 37, 39, 41, 43, 45, 47, 49, 51, 53 or 55, and which:

(a) encodes a polypeptide having amino acid sequence of respectively SEQ ID No 2, 4, 6, 8, 10, 12, 14, 16, 18, 20, 22, 24, 36, 38, 40, 42, 44, 46, 48, 50, 52, 54 or 56 and/or (b) has at least 85%, preferably at least 90%, more preferably at least 95%, and most preferably at least 98% or at least 99% identity over its whole length with one of the polynucleotides having respectively sequence of SEQ ID No 1, 3, 5, 7, 9, 11, 13, 15, 17, 19, 21, 23, 35, 37, 39, 41, 43, 45, 47, 49, 51, 53 or 55 and/or, (c) is a fragment of the polynucleotide having sequence of sequence SEQ ID No: 1, 3, 5, 7, 21, 23, 35, 37, 39, 41, 43, 45, 53 or 55, and encodes a polypeptide comprising or consisting of an antigen-binding fragment.

Polynucleotides of the invention can also be optimized sequences, especially for the expression in host cells. Optimisation techniques in this field are conventional ones.

Polynucleotide fragments of the invention have advantageously a sequence of at least 9 nucleotides, in particular at least 18 nucleotides and are shorter than their sequence of origin, especially shorter than full-length illustrated VH or VL sequences respectively.

According to a particular embodiment, polynucleotides of the invention may advantageously comprise, besides a sequence encoding a macromolecule according to the invention, upstream from the sequence encoding the antibody chains, a sequence encoding a signal peptide allowing secretion of said protein when expressed in a production cell. They may also comprise one or more sequence(s) encoding one or more marker peptide(s) for detecting, and/or facilitating the purification of, said protein.

The invention also concerns a vector for the cloning and/or for the expression of a polynucleotide disclosed herein. In a particular embodiment, the vector of the invention is a plasmid suitable for cloning and/or expressing in mammalian cells, which comprises regulation sequences for transcription and expression.

The invention further relates to cells or cell lines recombined with a polynucleotide of the invention, especially a mammalian or an avian cell or cell line. For example Chinese Hamster Ovary Cells, genetically modified to reduce global fucosylation. Indeed, Antibodies lacking core fucosylation show a significantly enhanced antibody-dependent cell-mediated cytotoxicity (ADCC) (von Horsten et al., 2010). Another example is the EB66 cell line which naturally has low fucosylation properties (Olivier et al., 2010).

Thus the invention also relates to a method of preparing an antibody or an antigen-binding fragment thereof, which comprises:
(a) obtaining a hybridoma after immunizing an animal, especially a mammal with the human alpha chain of the human IL-7 receptor, preferably with an antigen thereof comprising the sequences of human CD127 with the sequences of SEQ ID No:115 (and/or SEQ ID No: 110) and/or SEQ ID No:117 (and/or SEQ ID No: 111) and/or SEQ ID No: 116 (and/or SEQ ID No:86), said antigen comprising other sequences of human CD127 or not, as disclosed above, and, where necessary, boosting said animal with the same immunogen, recovering spleen or lymph node cells from the animal responding to immunization and fusing said cells with myeloma cells to isolate monoclonal antibodies and/or
(b) expressing polynucleotides coding for such antibodies such as polynucleotides disclosed herein with their nucleotide sequence in the recombinant form in cells in conditions enabling the recovery of antibodies, and
(c) recovering antibodies recognizing an epitope as defined herein, in particular comprising sequences from the 2b site of CD127 and in particular comprising such sequences and in addition sequences from the D1 domain of CD127, in particular antibodies having the desired binding affinity against the alpha chain of the human IL-7 receptor.

In a particular embodiment of the invention, the antibodies or their fragment are prepared in cells that present low fucosylation properties, such as EB66 avian cells.

The invention also relates to a method of selection of antibodies comprising the steps of obtaining, possibly through one of the methods described herein, antibodies or fragments thereof which specifically bind CD127, in particular an antigen thereof as disclosed above, and selecting among these antibodies those that do not increase the TSLP-induced maturation of immune cells, in particular dendritic cells, that do not induce internalization of CD127 and/or that inhibit IL7-induced internalization of CD127 and/or that inhibit in vitro and/or in vivo expression of α4, β7 and/or α4/β7 integrins. The selection may be performed using any of the procedures described in the Examples section to test for increase or decrease of TSLP-induced expression of cell surface markers CD40 and/or CD80 or to test for effects on internalization of CD127 or to test for effects on the expression of α4, β7 and α4/β7 integrins.

Such tests can conveniently be performed in e.g. 96-well plates to allow for fast and efficient screening of a large number of candidate antibodies and the readout can be performed by classical immunostaining and flow cytometry analysis. Thus, the invention relates to a method of selecting antibodies, antigen-binding fragments thereof or other macromolecule which comprises or consists of at least one of the following steps:
a. Testing (e.g. as described in Example 1, Example 2, Example 6 and/or Example 7) a macromolecule with the binding capacity of the macromolecule to CD127, in particular to an antigen thereof as disclosed herein;
b. Testing (e.g. as described in FIG. 16 and/or Example 5) the internalization of CD127 in CD127-expressing cells induced by the presence of the macromolecule;
c. Testing (e.g. as described in FIG. 16 and/or Example 5) the inhibition by the macromolecule of IL7-induced internalization of CD127 in CD127-expressing cells;
d. Testing (e.g. as in FIG. 5, FIG. 6 and/or Example 9) the increase of the maturation of DCs induced by TSLP in the presence of the macromolecule;
and optionally comprising at least one of the following steps:
e. Testing (e.g. as in FIG. 1, FIG. 2 and/or Example 3) the inhibition by the macromolecule of IL-7 induced signalling, in particular STAT5 phosphorylation;
f. Testing (e.g. as in Example 9, FIG. 5 and/or FIG. 6) the inhibition by the macromolecule of TSLP-induced production of TARC;
g. Testing (e.g. as in Example 16, FIG. 19 and/or FIG. 20) the inhibition by the macromolecule of the expression of α4, β7 and/or α4/β7 integrin expression, in particular cell surface expression on T-lymphocytes;
h. Testing (e.g. as in Example 21, FIG. 28) the disruption by the antibody of the binding of CD127 to the γc chain, in particular in the presence of IL-7.
Each of these testing steps being followed by the selection of one or more macromolecules having the desired functional features, as disclosed herein.

As mentioned above, when it is desired that the antibody recognizes an epitope comprising sequences which are not contiguous in the sequence of CD127, it is possible to test successively the recognition of (or binding to) fragments of the epitope consisting (or essentially consisting) of a single contiguous sequence of CD127. For example, if it is desired to obtain an antibody recognizing an epitope comprising sequences SEQ ID No:115, SEQ ID No:116 and SEQ ID No:117, it is possible to first select antibodies recognizing an epitope essentially consisting of SEQ ID No:116, and then secondly to select, among these first selected antibodies, antibodies recognizing an epitope essentially consisting of SEQ ID No:115, and then to select, among these secondly selected antibodies, antibodies recognizing an epitope essentially consisting of SEQ ID No:117. Obviously, the order of selection may be modified relative to this order, provided solely as an example.

Another object of the invention is a pharmaceutical composition comprising a macromolecule according to the invention, with a pharmaceutical vehicle, wherein said pharmaceutical composition optionally further comprises a different active ingredient.

The invention also relates to a composition comprising as an active ingredient, a macromolecule of the invention or a pharmaceutical composition as defined above, in a formulation suitable for controlling human CD127 positive cells survival or expansion, in particular human CD127 positive effector cells, especially CD127+ memory T cells survival or expansion, especially memory T cells which are both CD127+ and CD8+, or which are both CD127+ and CD4+ cells, when administered to a human patient. In a particular embodiment, the composition comprising the macromolecule of the invention as an active ingredient is in a formulation suitable for controlling the differentiation and/or maturation of dendritic cells when administered to a patient.

A composition of the invention may further comprise an additional compound having a therapeutic immunomodulator effect, in particular on cells involved in allergy or autoimmunity. For illustration purposes, exemplary immunomodulators of interest are other monoclonal antibodies targeting T cells, such as anti-CD3, anti-ICOS or anti-CD28 antibodies or recombinant proteins or antibodies targeting accessory cells such as CTLA4Ig or anti-CD40 antibodies.

The invention concerns also an antibody or an antigen-binding fragment thereof or a chimeric molecule as defined or illustrated herein, for use as active ingredient in a combination or add-on therapeutic regimen in a patient in need thereof. Also contemplated is the use of a macromolecule, nucleic acid, cell or cell line of the invention as a therapeutically active ingredient in a combination or in an add-on therapeutic regimen in a patient in need thereof.

A macromolecule according to the invention, a nucleic acid, vector, cell, cell line, pharmaceutical composition or a composition as defined herein are in particular proposed for use in a human patient for treating pathologic conditions influenced by immune responses, especially by memory T cells responses. Accordingly, the inventors proposed that the antibody or antigen-binding fragment thereof, chimeric molecule according to the invention, pharmaceutical composition or composition as defined herein be used for the treatment of autoimmune or allergic diseases in particular allergic skin disorders, intestinal disorders or for transplant rejection or for the treatment of leukemia such as acute lymphoblastic leukemia (e.g. T-ALL) or lymphoma such as Hodgkin lymphoma, or the treatment of a cancer disease such as breast cancer associated with CD127+ cells, renal cancer, bladder cancer, lung cancer, pancreatic cancer, or for the treatment of a T cell cutaneous lymphoma, such as Sezary lymphoma, or for the treatment of the acute lymphoblastoid leukemia with gain-of-function mutation of the IL-7-R/TSLP pathway.

In various embodiments, the invention is related to the use of macromolecules as defined herein in order to deplete CD127-positive cells while preserving CD127-negative cells.

In various embodiments, the invention is related to the use of macromolecules as defined herein in order to prevent differentiation and/or expansion and/or maturation of CD127-positive cells, in particular differentiation, expansion, or maturation induced by IL-7 and/or TSLP, while having little or no direct effect on CD127-negative cells.

In a particular embodiment, the invention relates to the use of macromolecules defined herein in order to eliminate/neutralize naïve and memory T cells by interfering with IL-7-induced signaling, while preserving Treg cells.

In a particular embodiment, the invention also relates to the use of macromolecules defined herein in order to deplete subpopulations of lymphocytes, or other cell populations expressing CD127 (including normal or pathologic T and B lymphocytes, NK cells, dendritic cells and other cell types including epithelial cells) as a result of cytotoxic action of the antibodies, possibly but not exclusively through ADCC (Antibody-Dependent Cellular Cytotoxicity) and optionally through CDC (Complement-Dependent Cytotoxicity).

In the embodiments above, the contemplated used are also applicable to nucleic acids, vectors, cells, cell lines and compositions of the invention.

By "treatment" or "therapeutic treatment", it is meant that the performed steps of administration result in improving the clinical condition of an animal or a human patient in need thereof, who suffers from disorder(s) associated with the IL-7 pathway, i.e. involving the activation or proliferation of CD127 positive cells. Such treatment aims at improving the clinical status of the animal or human patient, by eliminating or alleviating the symptoms associated with the disorder(s) related to the IL-7 pathway, i.e. involving the activation or proliferation of CD127 positive cells. In a preferred embodiment, the treatment according to the invention enables restoring to health. In a preferred embodiment, said treatment does not have undesired negative effects due to increased maturation of immune cells, in particular of dendritic cells.

The invention includes the use of the macromolecules in the treatment of pathologic conditions involving the alteration of immune response in a human patient leading to dominant tolerogenic state or, to the contrary, lack of tolerance where control of the level of the immune response would be needed as well as destruction of malignant CD127-positive cells.

The invention provides means suitable for use in pathologies such as those induced by transplant rejection, autoimmune diseases, allergic diseases, respiratory diseases, chronic viral infections, lymphoma, leukemia or other cancer diseases including those resulting from solid tumors (e.g. breast cancer) when these pathologies are associated with CD127 positive cells as well as the IL-7 signalling pathway and where an increase in the maturation of dendritic cells must be avoided.

In a particular embodiment, the invention relates to the use of a macromolecule, nucleic acid, cell, cell line or composition of the invention in a human patient for the treatment of an autoimmune disease or an allergic disease or for the treatment of leukemia such as acute lymphoblastic leukemia or for the treatment of lymphoma, or for the treatment of cancer disease, or for the treatment of a chronic viral infection, or for the treatment of inflammatory diseases, or for the treatment of respiratory diseases, or for the treatment of symptoms related to a transplantation.

In a particular embodiment, the invention relates to a method of treatment comprising the administration of a macromolecule, nucleic acid, cell, cell line or composition of the invention in a human patient for the treatment of an autoimmune disease or an allergic disease or for the treatment of leukemia such as acute lymphoblastic leukemia or for the treatment of lymphoma, or for the treatment of cancer disease, or for the treatment of a chronic viral infection, or for the treatment of inflammatory diseases, or for the treatment of respiratory diseases, or for the treatment of symptoms related to a transplantation.

Additional features and properties of the invention will be apparent from the Examples and figures which follow.

BRIEF DESCRIPTION OF DRAWINGS

FIG. 2. Inhibition of IL-7R signalling by N13B2 mAb. Axes as in FIG. 1. (A) Inhibition of IL-7 induced pSTAT5+ T lymphocyte in dose-response to N13B2 mAb (squares) as compared to MD707-3 mAb (circles), both in rodent format. (B) Same experiment as in (A) with human IgG1 (square) and human IgG4 (circle) chimeric forms of N13B2 in the presence of 0.1 (empty symbols) or 5 ng/ml (full symbols) of recombinant human IL-7. N13B2 is more efficient in inhibiting STAT 5 than MD707-13 (~50% inhibition at 100 ng/ml for N13B2, vs. 1000 ng/mL for MD707-13), while different IgG isotypes of N13B2 display comparable inhibition efficiency.

TABLE 1

Results of bindng studies

| | Ka (1/Ms) | Kd (1/s) | KA (1/M) | KD (M) |
|---|---|---|---|---|
| MD707-1 | 2.66 E+05 | 1.21E−04 | 2.19E+09 | 4.56E−10 |
| N13B2 | 2.01E+05 | 1.60E−05 | 1.26E+10 | 7.96E−11 |

TABLE 2

Kd of N13B2 and its chimeras described in (A) in a separate experiment

| Antibody | Ka1 (1/Ms) | Kd1 (1/s) | Rmax (RU) | KA (1/M) | KD (M) |
|---|---|---|---|---|---|
| N13B2 rat | 9.63E+04 | 4.75E−06 | 115 | 2.03E+10 | 4.93E−11 |
| N13B2-G1 | 1.49E+05 | 5.62E−05 | 109 | 2.65E+09 | 3.77E−10 |
| N13B2-G4 | 2.01E+04 | 3.41E−06 | 94.9 | 5.89E+09 | 1.70E−10 |

FIG. 4. The Anti CD127 activity of the new antibody N13B2 was measured by ELISA assay using a recombinant hCD127 antigen. OD 450 nm: optical density at 450 nm. A. The CD127 binding activity of the N13B2 (full circle) was compared to the previous antibody generation (MD707-1 (empty diamond), 3 (empty triangle) and 6 (full square)). N13B2 appears as the most efficient binder in the assay. B. The CD127 activity between different N13B2 formats (rat, IgG1 (circle) or IgG4 (square)) was compared. No significant difference in binding activity was observed.

TABLE 3

ED50 of selected antbibodies

| | ED 50 (ng/ml) |
|---|---|
| N13B2 | 65.64 |
| MD707-1 | 122.93 |
| MD707-3 | 293.32 |
| MD707-6 | 2789.41 |
| St cMD707-3-G1 | 16.1 |
| CN13B2-G1 | 12 |
| CN13B2-G4 | 12.6 |

FIG. 5. TSLP-induced TARC (Thymus and Activation-Regulated Chemokine, CCL17) production and expression of CD80 cell surface marker by myeloid dendritic cells. None: no stimulation. LPS: stimulation with lipopolysaccharide. TSLP: stimulation with TSLP. A) Quantification of TARC production in supernatant by ELISA and B) CD80 cell surface expression by flow cytometry of human blood CD1C+ dendritic cells cultured for 24 hours with medium alone, 1 μg/ml LPS or 15 ng/ml of TSLP. Data are mean±Standard error or the mean (SEM) concentration from 3 independent experiments.

Figure 6:
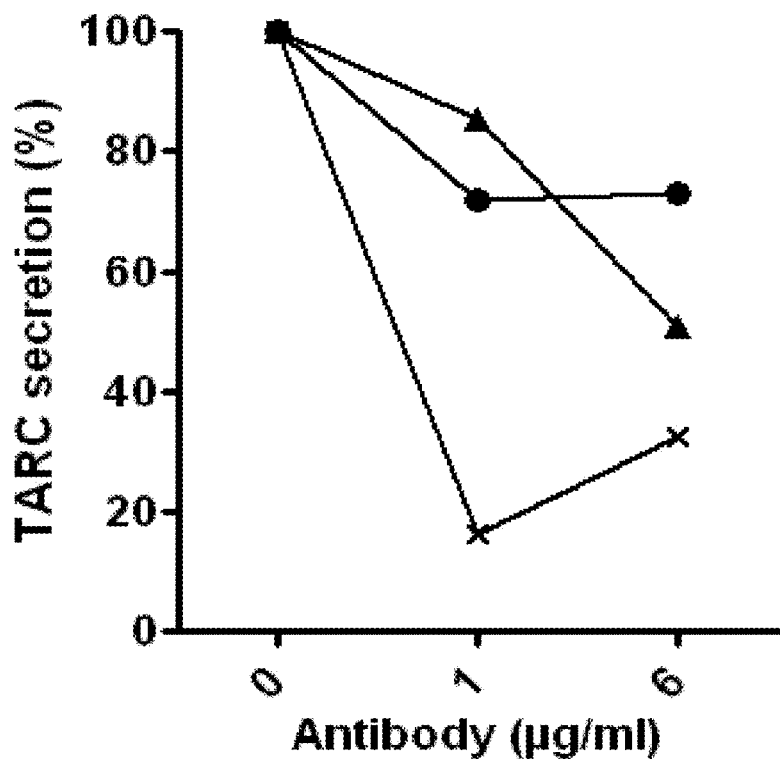

FIG. 6. Inhibition of TSLP-induced TARC production by anti-human CD127 antibodies. Quantification by ELISA of TARC production in supernatant of human blood CD1C+ dendritic cells cultured for 24 hours with 15 ng/ml of TSLP and different concentration of anti-human CD127 antibodies: N13B2 antibody (circle), MD707-6 (triangle) and anti-TSLP as a control (X). Data are representative of three independent experiments from three different blood donors. N13B2 inhibits only very moderately the induction of TARC secretion (~20% inhibition at 6 μg/mL), while MD707-13 and anti-TSLPR are more efficient inhibitors (resp. ~50% and ~70% inhibition).

FIG. 7. Effect of anti-CD127 antibodies on TSLP-induced CD80 and CD40 expression marker of dendritic cells maturation. Cells were activated by TSLP at 15 ng/ml for 24 hours. N13B2, MD707-3 and MD707-6 anti-CD127 antibodies were added to the supernatant at 6 μg/ml. CD80 (A) and CD40 (B) expression at the cell surface were analysed by FACS. Data are representative of 3 independent experiments and are expressed in % of expression in control cells (medium=no antibody, with TSLP). Only N13B2, of the tested antibodies, does not increase the cell surface expression of CD40 and CD80 in TSLP-treated cells.

Figure 8:
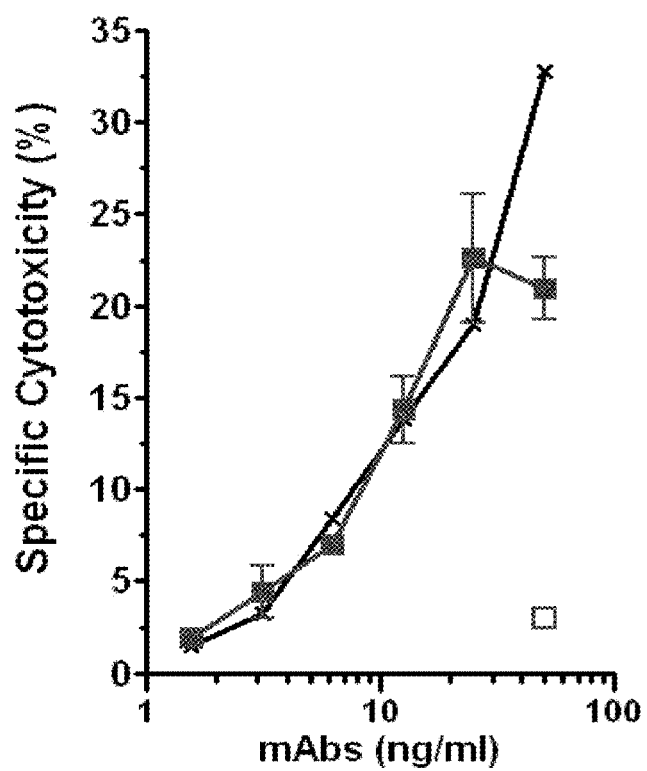

FIG. 8. Antibody-dependent cellular cytotoxicity (ADCC) of chimeric N13B2 (IgG1 or igG4) anti-human CD127 antibody. Human NK cells used as effector (E) were incubated for 4 hours with a human CD127-transfected BAF/3 cell line as target cells (10 effector to 1 target cell ratio) and with different concentration of chimeric N13B2 IgG1 (full square), N13B-IgG4 (empty square) or chimeric MD707-3 (X). Percentage of specific cytotoxicity was determined by 51Cr release.

FIG. 9. Efficacy of rat N13B2 anti-CD127 mAbs to improve colitis induced chemically in humanized immuno-deficient mice. Survival (A) and change in weight (B) were monitored daily from day 0, start of the chemical treatment with 2,4,6-trinitrobenzenesulfonic acid (TNBS), which induces severe colonic inflammation when administered intrarectally, after injection of PBS (solid line/full triangle) or N13B2 anti-IL7Rα antibody (dotted line, empty triangle). In (B), each point represents an average weight data (+/− SEM); n=6 for the Hu-TNBS+PBS group and n=6 for TNBS group+anti-IL-7Rα. Survival is increased and weight loss is reduced in the treated group.

FIG. 10. Nucleotidic and amino acid sequence of the N13B2_G1M chimera VH and VL chains. Fc chains are printed in lower case, the three CDRs in each sequence are underlined. An asterisk (*) designates the stop codon in the amino acid sequence.

FIG. 11. Nucleotidic and amino acid sequence of the N13B2_G4M chimera. Fc chains are printed in lower case, the three CDRs in each sequence are underlined. An asterisk (*) designates the location of the stop codon in the amino acid sequence.

FIG. 12. Amino acid sequence of three alternative human Fc chains (IgG1, IgG2 and IgG4) and of the Fc chain of the rat N13B2 antibody (IgG1).

Figure 13:
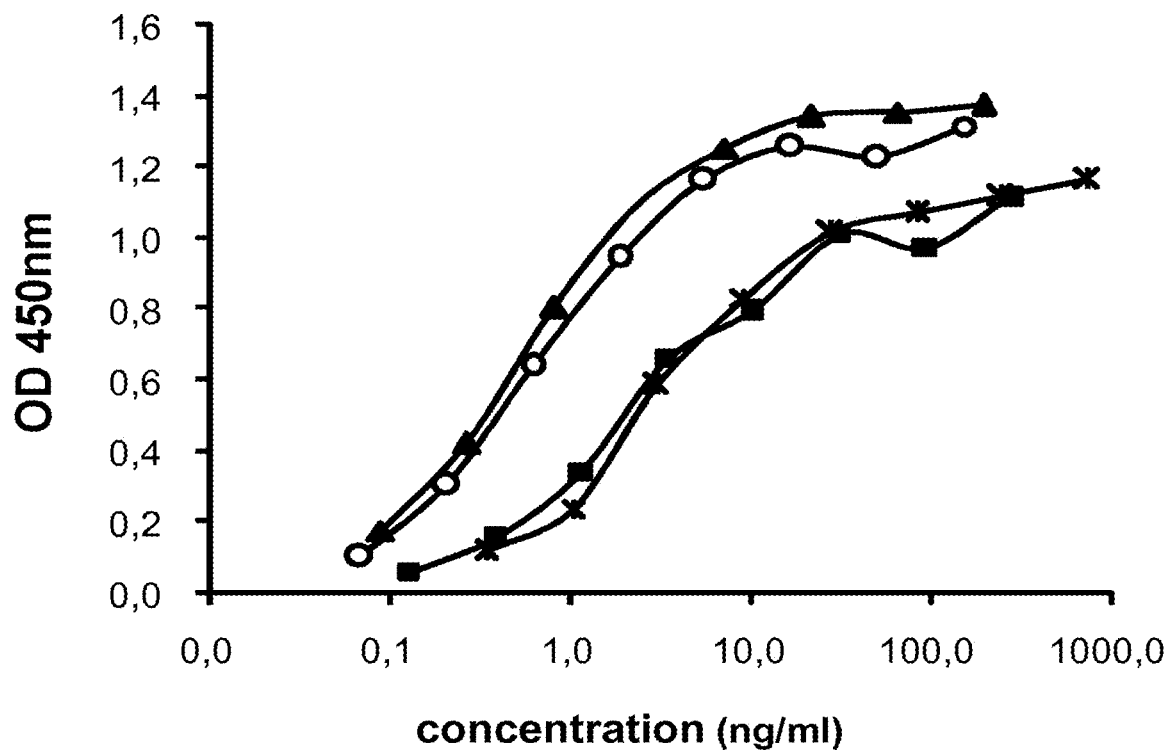

FIG. 13. anti-CD127 ELISA binding assay: coating human CD127Fc and revealed with an anti-human kappa antibody. The Anti CD127 activity of the new antibody N13B2 was measured by ELISA assay using a recombinant hCD127 antigen. The CD127 activity between different N13B2 antibody formats (wt (X), an IgG4 humanized h1 (full square), h2 (empty circle) or h3 (full triangle) antibodies) were compared. OD: optical density.

TABLE 4

ED 50 of selected antibodies

| | ED 50 (ng/ml) |
|---|---|
| N13B2 wt | 3 |
| N13B2-h1 | 2.4 |
| N13B2-h2 | 0.6 |
| N13B2-h3 | 0.6 |

Figure 14:
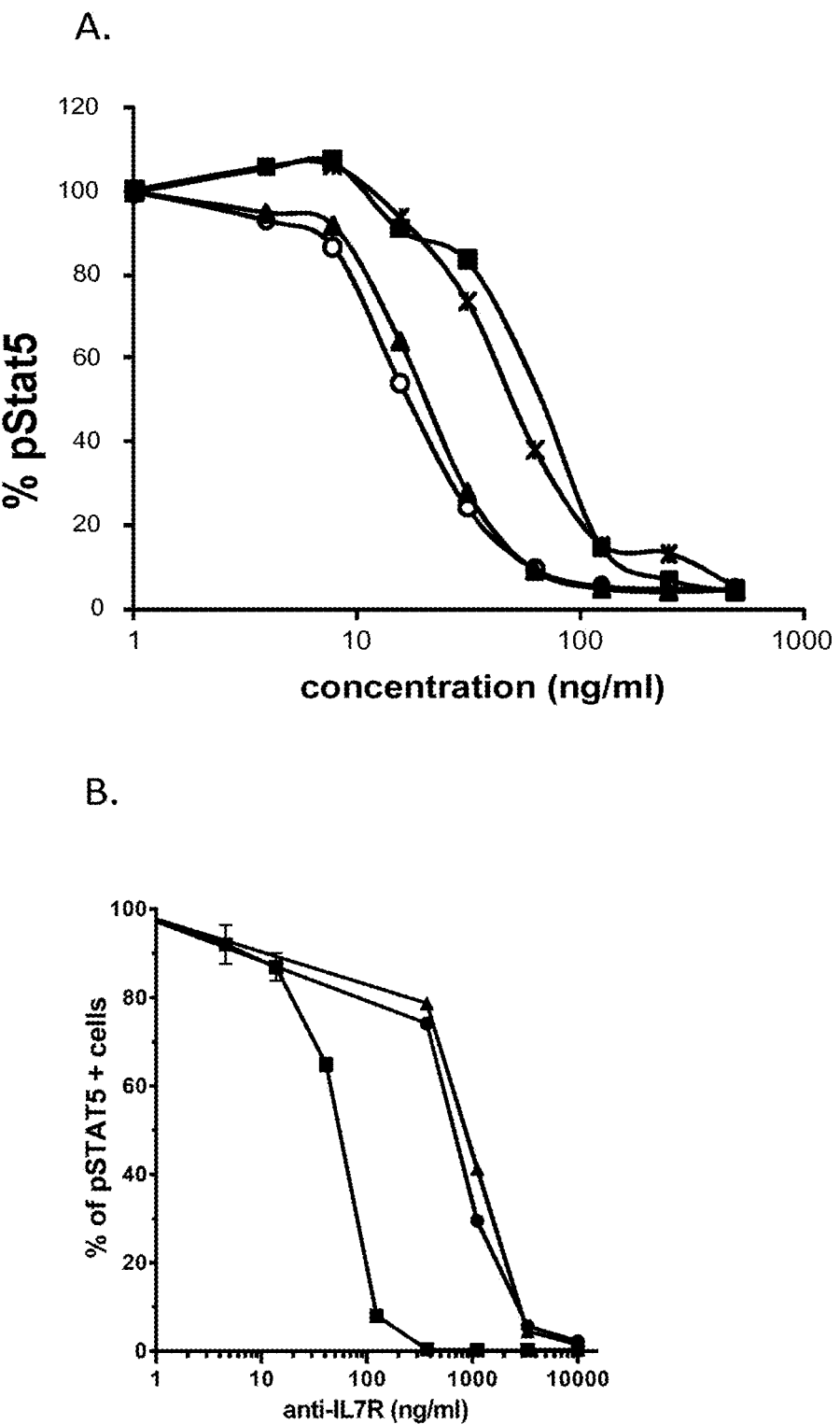

FIG. 14. FIG. 14: P-STAT5 inhibition with anti-CD127 antibodies: A. Inhibition of IL7 induced P-STAT5 by humanized N13B2 mAbs on T lymphocyte (N13B2 h1 (black square), h2 (open circle) and h3 (black triangle) in a dose dependent manner and compared to Rat N13B2 wt (X) antibody in the presence of 0.1 ng/ml of recombinant human IL-7. B. Different anti-CD127 antibodies from previous antibody generations were compared for their ability to inhibit IL7 dependent P-STAT5: MD707 3 (circle), MD707 4 (triangle) and MD707 13 (square).

TABLE 5

IC 50 of selected antibodies

| | IC 50 (ng/ml) |
|---|---|
| N13B2 wt | 50.2 |
| N13B2-h1 | 63.8 |
| N13B2-h2 | 18.7 |
| N13B2-h3 | 21.2 |

Figure 15:
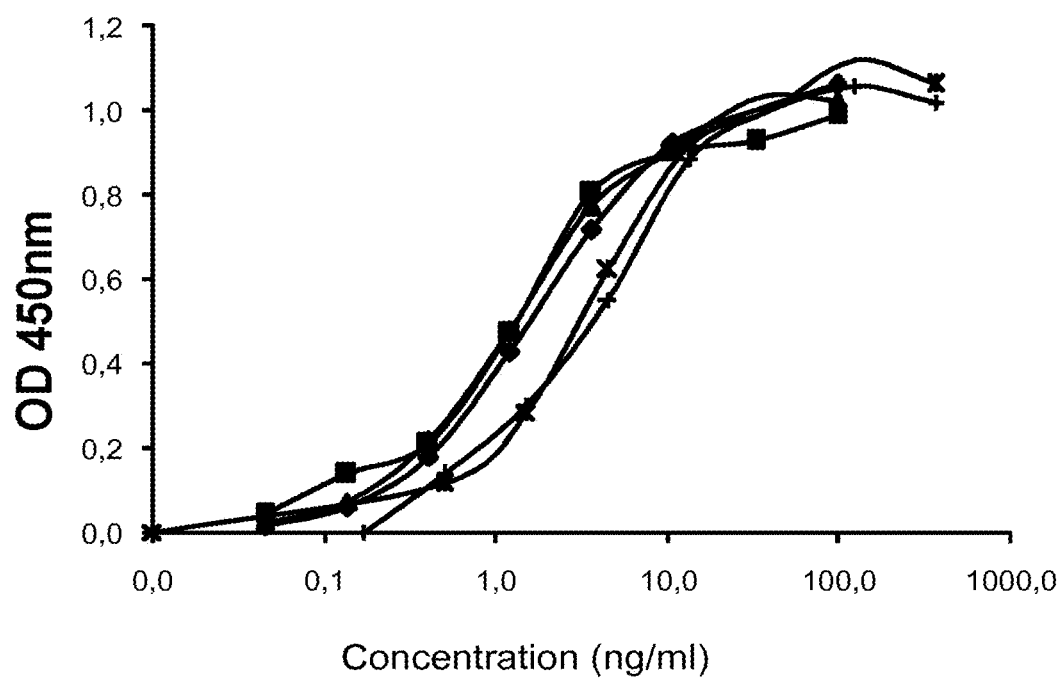

FIG. 15. Stability assay of humanized versus Rat anti-CD127 antibodies. Antibody concentrations was measured by ELISA after 7 days at 37° C. (Rat N13B2 wt (+) or humanized N13B2 h3 (square)) and at −80° C. (Rat N13B2 wt (X) or humanized N13B2 h3 (triangle)) and after four frost/defrost events (diamonds).

TABLE 6

Binding activity of the antibodies after 7 days at 37° C. or at −80° C. and after 4 time frost/defrost events.

| | ED 50 (ng/ml) |
|---|---|
| N13B2 wt_store at −80° C. | 3.6 |
| N13B2 wt_store 7 d at 37° C. | 3.5 |
| N13B2-h3_store at −80° C. | 1.3 |
| N13B2-h3_store 7 d at 37° C. | 1.1 |
| N13B2-h3_4x frost and defrost | 1.7 |

TABLE 7

Stability assay of humanized versus rat anti-human CD127 antibodies: Analysis by gel filtration of aggregate formation after incubation for 7 days at 37° C. or at −80° C.

| | N13B2-wt | | N13B2-h" | |
|---|---|---|---|---|
| | D7 at −80° C. | D7 at 37° C. | D7 at −80° C. | D7 at 37° C. |
| % aggregates | 3 | 4 | 2.8 | 3.2 |
| % monomers | 97 | 96 | 97.2 | 96.8 |

FIG. 16. Competition and internalization assays by cytometry. Human peripheral blood mononuclear cells were incubated with several anti-CD127 mAbs, for 30 min at either 4° C. (hatched bar) or 37° C. (black bar) or at 37° C. for 30 min without IL-7 and then for 15 min with 5 ng/ml of recombinant human IL-7 (grey bar): (A) 10 µg of clones MD707-5, MD707-12 or MD707-13 or the chimeric N13B2-G4; (B) 50 ng of N13B2, HAL clone H3L4 or 1A11 or medium as control. Cells were then stained at 4° C. with commercially available anti-human CD127 mAbs to assess IL-7 receptor alpha chain expression at the cell membrane level.

MD707-5, MD707-12 and MD707-13 antibodies induced internalization of the receptor at 37° C. with or without IL-7, while the chimeric N13B2-G4 did not. HAL antibody induced a decrease in cell surface expression of CD127 in any conditions. Results at 4° C. show that 1A11 antibody competes slightly with the antibody used for labelling, while HAL shows strong competition and N13B2 no competition. At 37° C., no cell surface staining was observed in the presence of HAL, while 1A11 alone induced a strong decrease in cell surface expression of CD127 and when combined with IL-7, the cell surface expression was decreased by ~90%. In contrast, N13B2 did not reduce cell surface expression of CD127 at 4° C., neither did it induce a decrease in cell surface expression of CD127 used alone, and it inhibited the decrease observed in the presence of IL-7.

FIG. 17. (A) Pharmacokinetic and pharmacodynamics study of N13B2 and MD707-13 mAb administration in non-human primates. Baboons (*Papio anubis*) were treated intravenously with 10 mg/kg of N13B2-IgG1 (n=3, full square), N13B2-IgG4 (n=3, full circle) or MD707-13-IgG4 (n=3, empty circle). Serum concentration of anti-CD127 mAb were monitored by ELISA. (B) In parallel, expression of CD127 at the surface of blood T lymphocytes was monitored by flow cytometry and normalized to level measured before injection of mAb (represented by dotted line). *p<0.05. Total plasma levels are comparable over time for all three antibodies. Cell surface expression of CD127 is decreased after ~8 days of treatment with MD707-13, while no such decrease is observed with any of the tested N13B2 clones.

Figure 18:
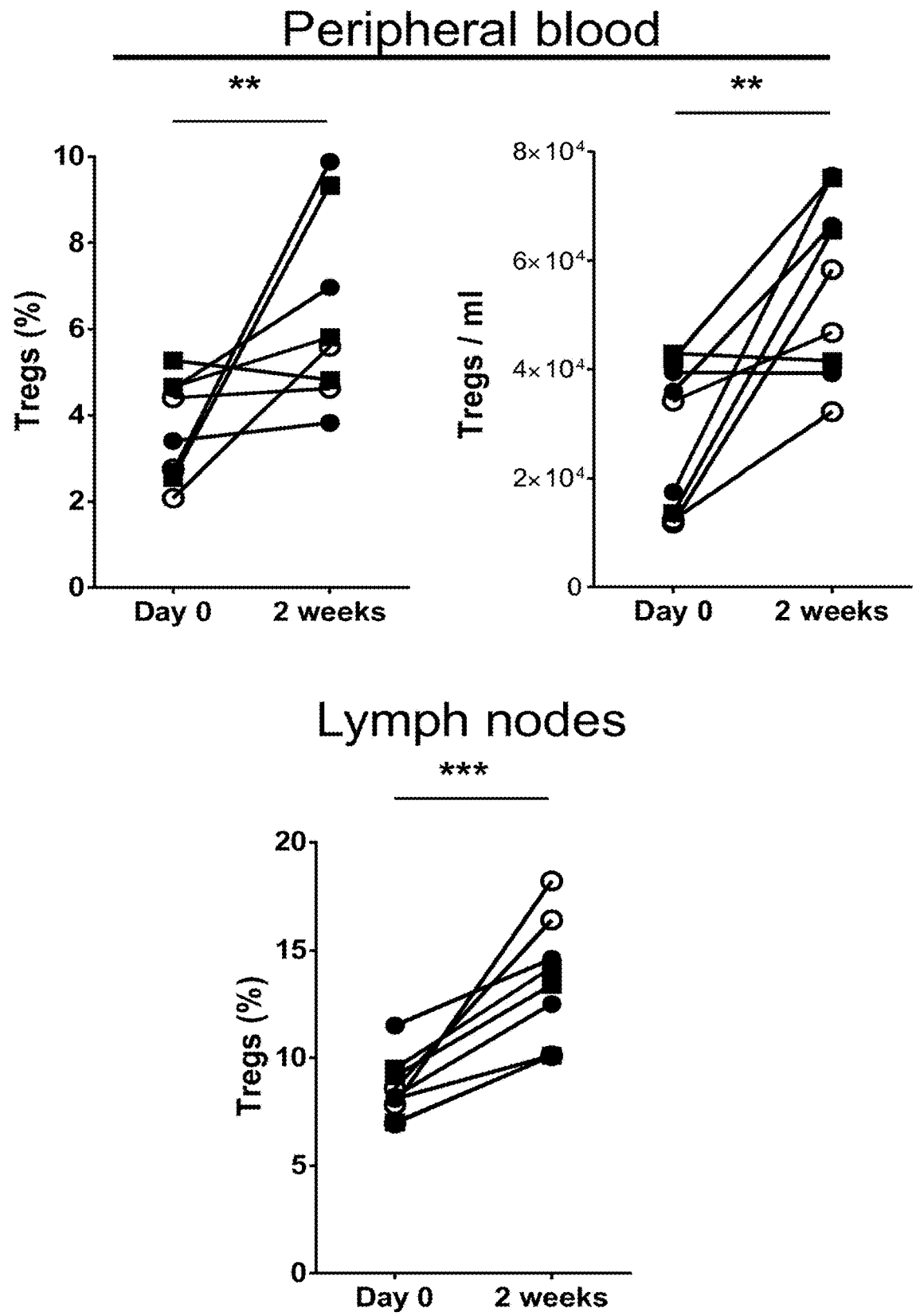

FIG. 18. Baboons (*Papio anubis*) were treated intravenously with 10 mg/kg of N13B2-IgG1 (n=3, full square), N13B2-IgG4 (n=3, full circle) or MD707-13-IgG4 (n=3, empty circle). The frequency of regulatory T lymphocytes (CD3+ CD4+ CD25high Foxp3+) in blood and lymph nodes (expressed as % of CD4 positive T cells) as well as absolute count number of regulatory T lymphocytes (expressed in cells/mL) was monitored at day 0 and 2 weeks after administration of mAbs. p<0.01, *p<0.001. All three antibodies increase the total count in blood and ratio in both blood and lymph nodes of regulatory T cells.

Figure 19:
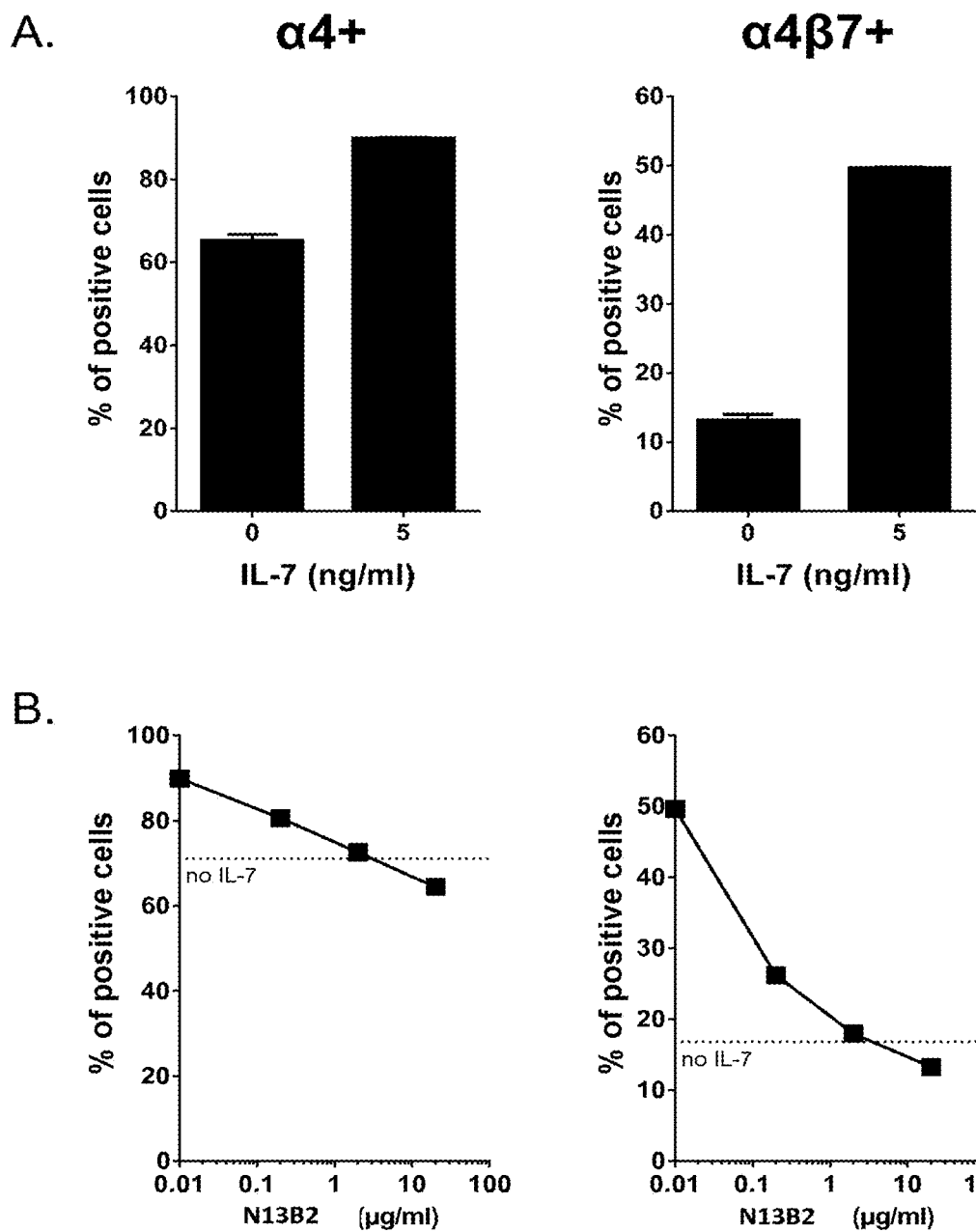

FIG. 19. In vitro inhibition of α4, β7 and α4/β7 integrin expression. A. Percentage of α4-positive and α4/β7-positive human T-lymphocyte, after 9 days of culture with or without 5 ng/ml of human IL-7, assayed by FACS. B. Same as top, with the indicated concentration of N13B2 mAb added to the culture at day 0. Dotted lines indicated the baseline level in a control condition (without IL-7 and N13B2 mAb). The IL-7-induced increase in expression of the α4, β7 and α4/β7 integrins is prevented by humanized N13B2 mAb in-vitro (it is completely inhibited at ~2 µg/mL antibody).

Figure 20:
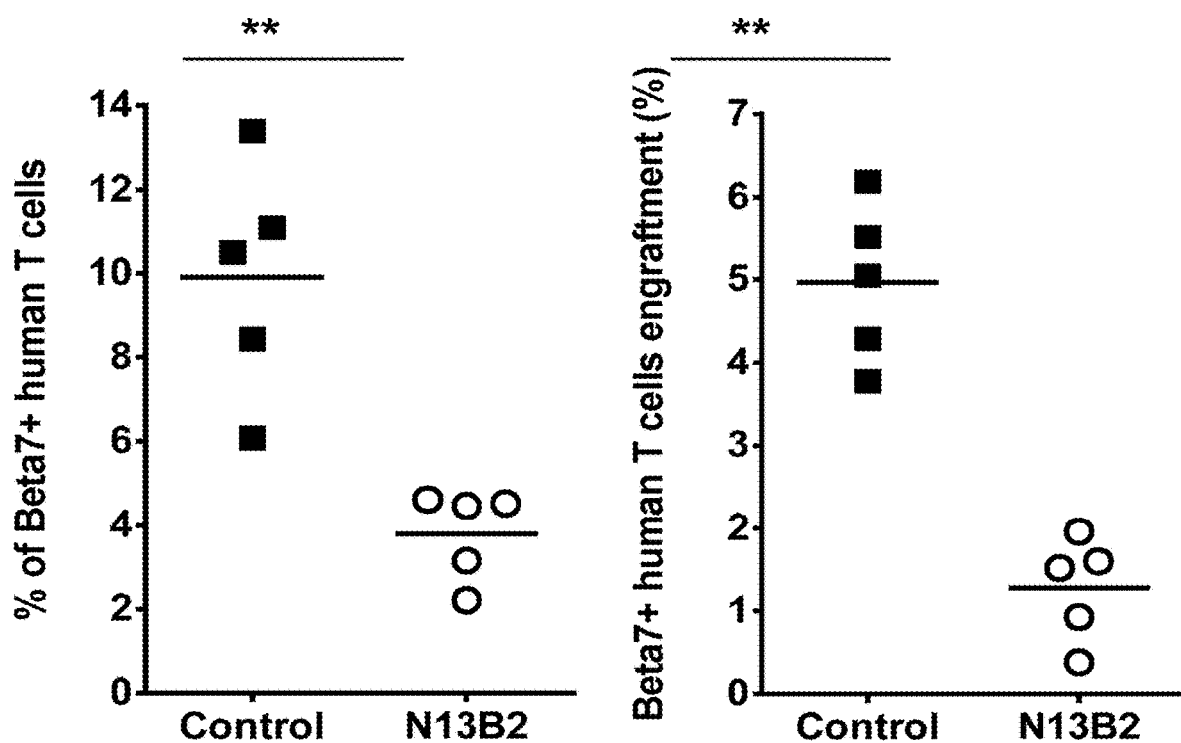

FIG. 20. In vivo inhibition of α4, β7 and α4/β7 integrin expression. $40 \times 10^6$ human peripheral blood mononuclears cells were injected intraperitonealy in irradiated immunodeficient mice (NOD/SCID/IL-2 receptor gamma-chain knock-out mice). Percentage of blood β7-positive T lymphocytes (left) and engraftment of β7-positive human T lymphocytes (right) after two weeks of treatment with control buffer (n=5) or N13B2 mAb (5 mg/kg, n=5), assessed by FACS. **$p<0.01$. N13B2 significantly reduces the ratio of β7 positive T cells, and the engraftment of β7-positive T cells.

Figure 21:
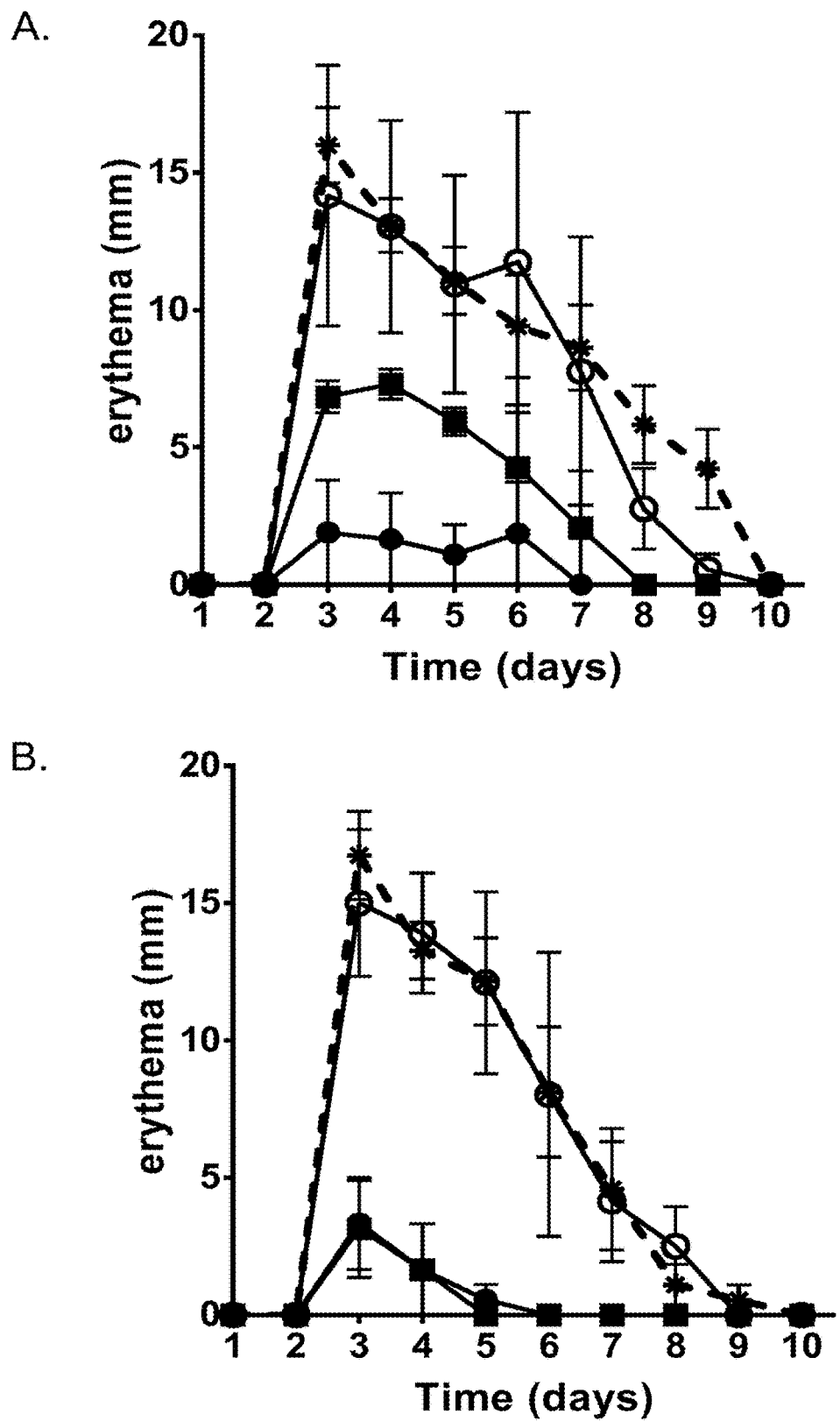

FIG. 21. Effect of N13B2 antibody on a DTH model, an in vivo psoriasis model. BCG-(Bacillus Calmette-Guerin) vaccinated baboons (*Papio anubis*) were challenged by an intradermal injection of 2000 (A) or 1000 (B) unit of purified tuberculin to induce delayed-type hypersensitivity response and diameters of erythema were recorded every day (asterisk; dotted line). One month later, animals were treated intravenously with 10 mg/kg of N13B2-IgG1 (n=3, full square), N13B2-IgG4 (n=3, full circle) or MD707-13-IgG4 (n=3, empty circle). Four hours after mAbs administration, animals were challenged again by an intradermal injection of 2000 (A) or 1000 (B) unit of purified tuberculin to induce delayed-type hypersensitivity response and diameters of erythema were recorded every day (solid lines). N13B2 but not MD707-13 antibody, inhibits memory lymphocytes response, as measured by the diameter of the erythema after the second challenge.

Figure 22:
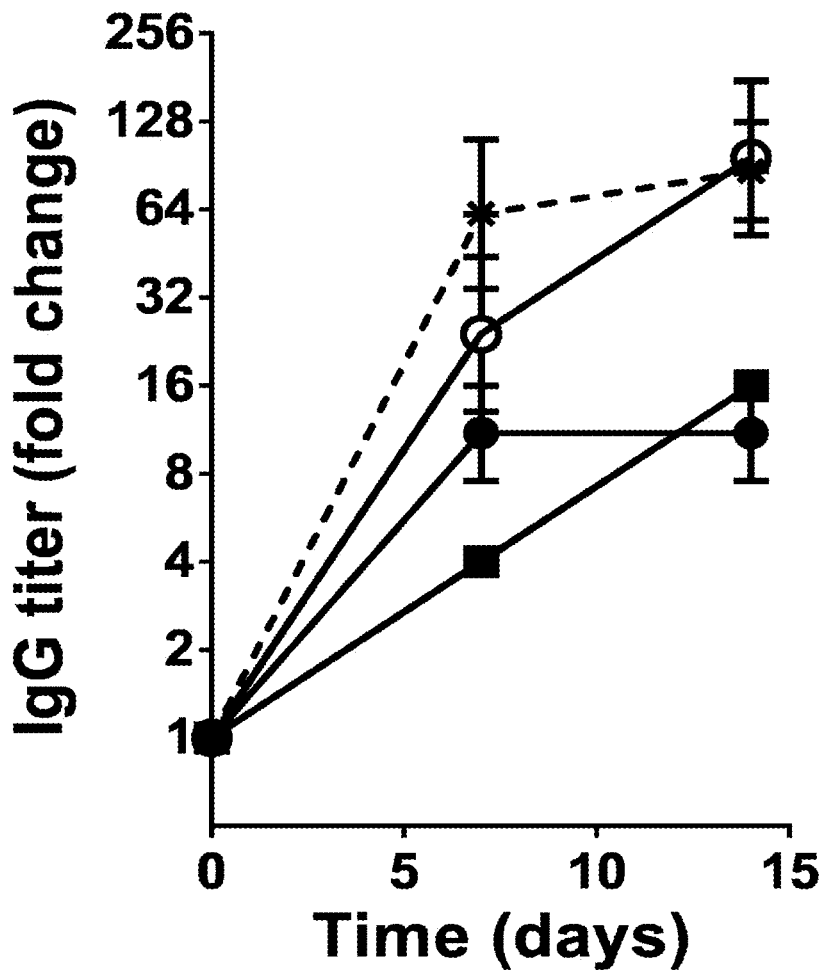

FIG. 22. Baboons (*Papio anubis*) were treated intravenously with 10 mg/kg of N13B2-IgG1 (n=3, full square), N13B2-IgG4 (n=3, full circle) or MD707-13-IgG4 (n=3, empty circle) or control buffer (n=3, dotted line). Four hours later, animals received an intravenous injection of 1.5 ml of sheep red blood cells (SRBC) at 10%. Specific anti-SRBC IgG titers were monitored 1 week and 2 weeks after administration of SRBC and normalized to their titers at day 0. *$p<0.05$. N13B2, but not MD707-13, inhibits humoral immune response, as measured by the specific IgG titer.

FIG. 23. Protein sequence of the humanized N13B2 VH IgG4 S228P_h3: sequence in grey are the CDRs, underlined and bolded amino acids are mutated (V42I, A54S, D82N, M108L), underlined sequence is the mutated IgG4 sequence (S228P).

FIG. 24. Protein sequence of the humanized N13B2 VL Ckappa_h3: sequence in grey are the CDRs, underlined and bolded amino acids are mutated (V54I, Y77F, F93Y+N31Q, S59T), underlined sequence is the mutated IgG4 sequence (S228P).

Figure 25:
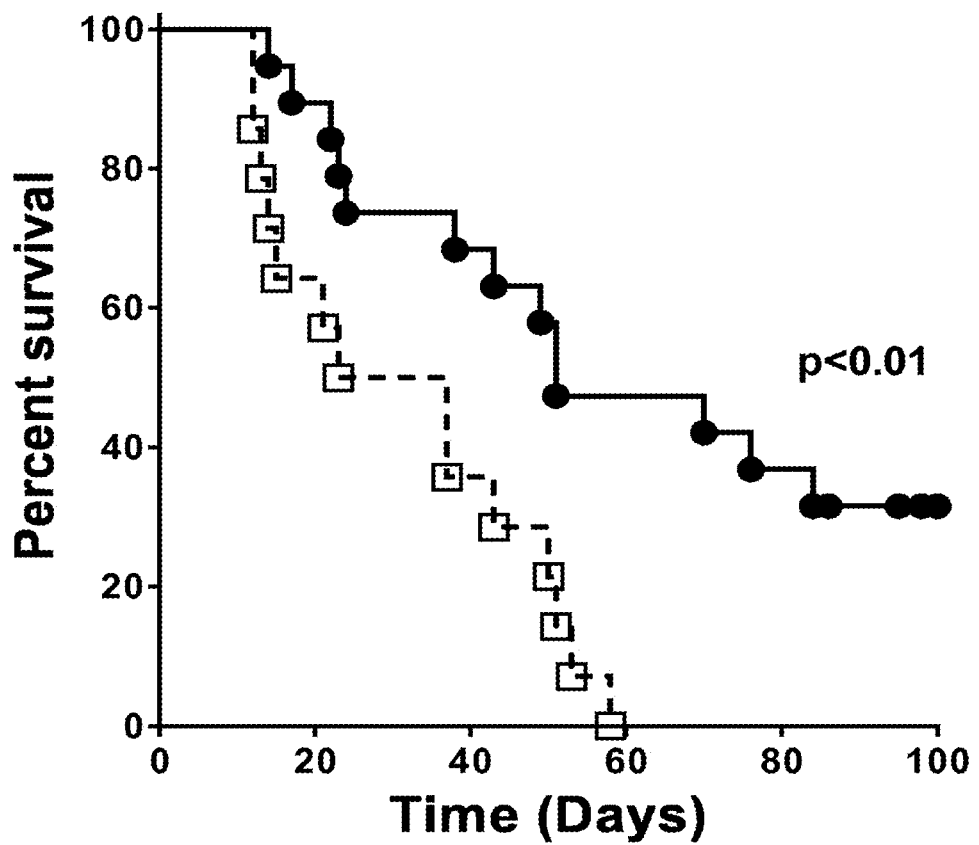

FIG. 25. N13B2 protects from death in an Inflammatory mice model: a graft-versus-host-disease was induced in humanized mice (see Example 13). Percentage of surviving NSG mice injected with 50 million human PBMC on day 0 receiving no treatment (white square, n=14) or treated three times per week by intraperitoneal injection with 5 mg/kg of chimeric N13B2 (black circle, n=19).

Figure 26:
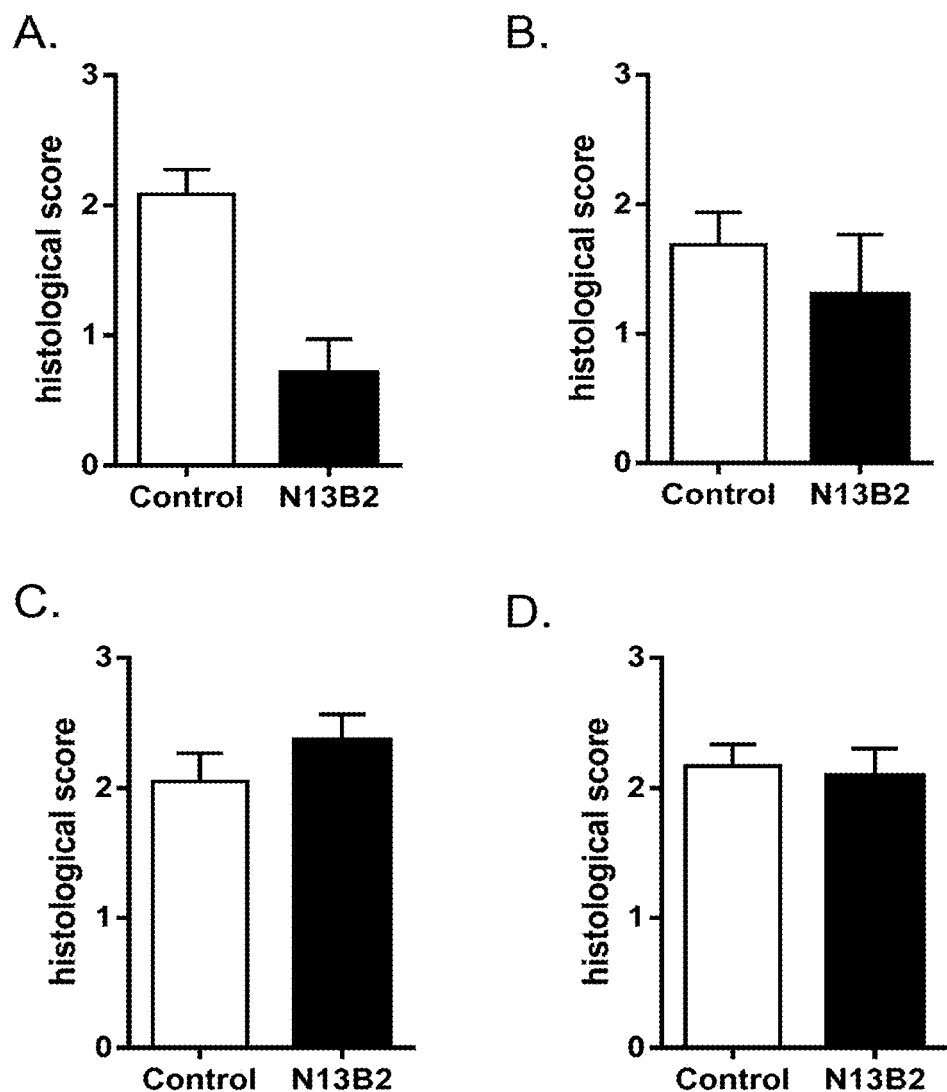

FIG. 26. N13B2 specifically prevents colon inflammation in an inflammatory mice model (see Example 13). At time of euthanasia (i.e. at 25% weight loss or 100 days after injection), inflammatory cell infiltrates in each tissue of NSG mice injected with 50 million human PBMC on day 0 and treated (black) or not (white) three times per week with 5 mg/kg of N13B2, was analyzed by histology on 10 µm slides stained with hematoxilin and eosin. Results are presented as follows: A. Colon, B. Intestine, C. Liver and D. Lung. Data are mean+/−SEM of at least n=8 per group.

FIG. 27. Epitope domains on CD127 protein (Uniprot P16871) that are recognized by N13B2 antibody. Amino acids in bold font correspond to the sequences forming the conformational epitope recognized by N13B2; amino acids on grey background are important for interaction with IL-7; amino acids that are stricken-through constitute the signal peptide of CD127.

Figure 28:
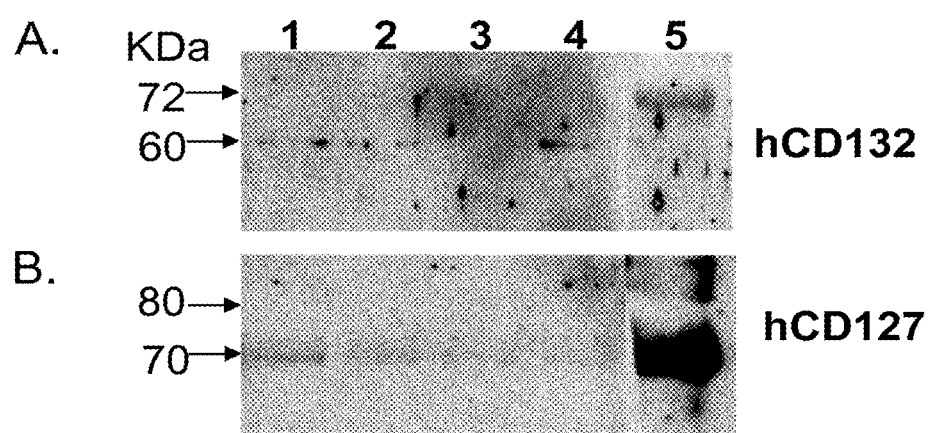

FIG. 28. Co-immunoprecipitation study of the CD127/IL7/CD132 complex with anti-hCD127 antibodies (Example 21). Lanes: 1—PBL alone, 2—PBL+IL7, 3—PBL+IL7+N13B2, 4—PBL+IL7+MD707-13, 5—CD132-Fc (72 Kda) or CD-127-Fc (80 KDa). Co-immunoprecipitation of samples on anti-hCD127 column (MD707-9). Eluates were analysed by western-blot with (A) Rabbit anti-human CD132 antibody revealed with peroxidase-labelled goat anti-rabbit or with (B) Rat anti-human CD127 antibody and revealed with a peroxidase-labelled donkey anti-rat antibody.

EXAMPLES

Example 1. Preparation and Selection of Novel Anti-Human CD127 Mabs

Rats were immunized with recombinant hCD127-Ig (hCD127 fused with a constant fragment of an immunoglobulin—Sino Biologicals, Beijing, China; reference 10975-H03H) and monoclonal antibodies were derived according to conventional techniques. The immunization protocol used was as follows: recombinant CD127 Fc Chimera (10975-H03H Sino Biological, Beijing, China) was used to immunize rats of the LOU/C Igk1a strain. Fifty micrograms of proteins were suspended in Complete Freund Adjuvant and administered s.c. After 20 days, a recall injection of the protein suspended in Incomplete Freund Adjuvant was performed. Another similar recall injection was performed on days 60 and a boost injection was performed on day 90 with 100 micrograms proteins, 4 days before spleen cells collection.

Hybridoma were obtained by fusing spleen mononuclear cells with the LOU rat immunocytoma IR983F, a non-secreting and azaguanine resistant cell line, according to a previously described procedure (Chassoux et al, 1988). Hybridoma were first screened according to the capacity of the secreted monoclonal antibodies to bind to recombinant CD127 molecule (CD127 Fc Chimera; 10975-H03H, Sino Biological, Beijing, China).

After selection, hybridoma were cultured in DMEM complete medium. Supernatant was concentrated by ultrafiltration (Centramate, Pall) and purified by affinity on Protein G chromatography (HiTrap, GeHealthcare). Elution was performed with glycine 0.1M pH 2.8 elution buffer. Resulting purified immunoglobulins were assessed in activity ELISA assay against CD127 human.

Among the first selected clones selected based on the recognition by secreted antibodies of recombinant CD127, 2 were further selected by flow cytometry on the recognition of CD127 expressed by human T cells and on their antagonist properties with respect to TSLP.

Antibodies were produced and their isotype were characterized as well as their affinities by Surface Plasmon Resonance measurement using BIAcore technology.

Example 2. rCD127 Recognition of Anti-h-CD127 Mabs Assessed by ELISA

Recombinant hCD127 (Sino Biologicals, Beijing, China; reference 10975-H08H) was immobilized on plastic and increasing doses of Mabs were added to measure binding. After incubation and washing, peroxidase-labeled mouse anti-rat kappa chain (AbdSerotec) was added and revealed by conventional methods. Binding was confirmed for each antibody.

Example 3. Inhibition of IL7 Signaling (pSTAT5)

Figure 1:
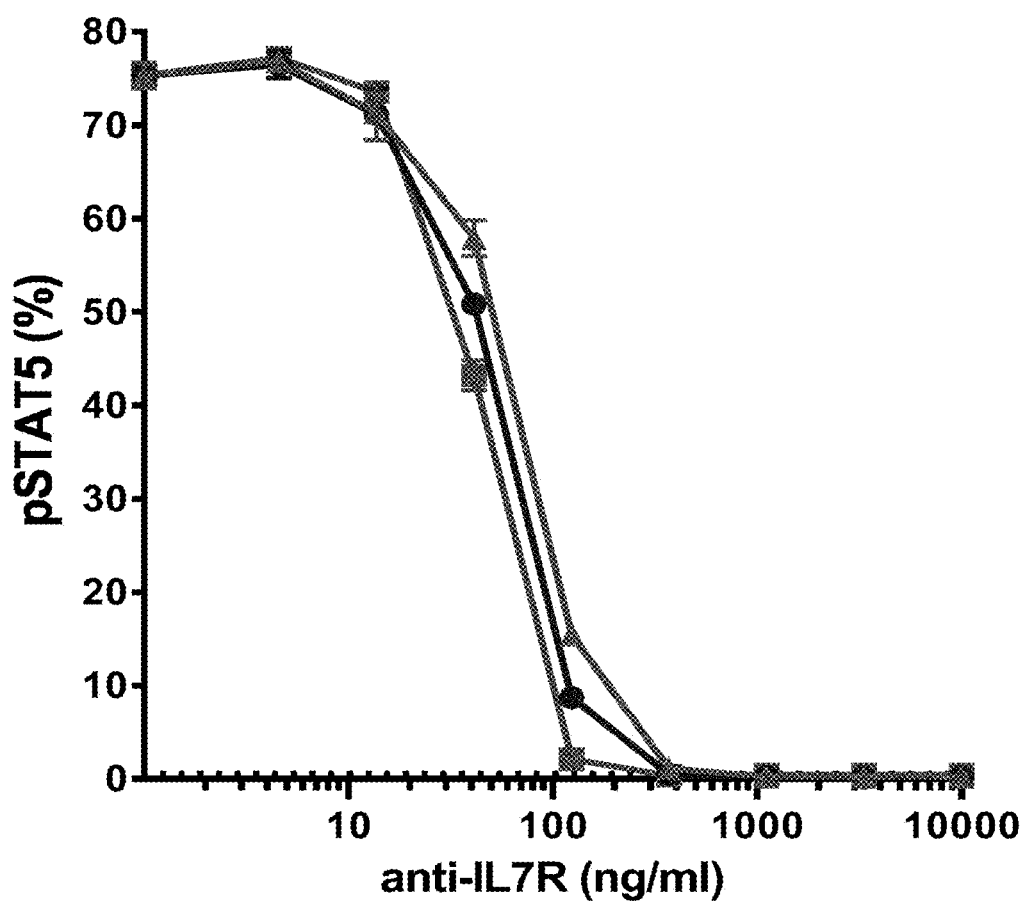
FIG. 1. Inhibition of IL-7R signaling. Inhibition of IL-7 induced pSTAT5+ T lymphocyte in dose-response to anti-human IL-7Rα monoclonal antibodies. N13B2 (square), N13E5 (circle) and N13K12 (triangle). pSTAT5(%): ratio (%) of cells positive for phospho-STAT5, as measured by FACS. Dose-dependent inhibition of STAT5 phosphorylation is similar for the three clones, all three inhibiting phosphorylation efficiently at 50 ng/ml (roughly 50% inhibition) and completely at 100 to 500 ng/ml (>95% inhibition).

Human peripheral blood monocytic cells (PBMC) harvested by ficoll gradient from healthy volunteers were incubated in serum-free media with different concentration of antibodies of interest for 15 minutes at room temperature, before incubation with 0.1 or 5 ng/ml of recombinant human IL-7 (rhIL-7; AbD Serotec ref PHP046) for 15 minutes at 37° C. PBMC untreated with rhIL-7 were analyzed as the background signal, while IL-7 treated cells without antibody were set as negative control. PBMC were then quickly chilled and washed with FACS buffer to stop the reaction. Cells were then incubated for 15 minutes with cold Cytofix/Cytoperm solution (BD Bioscience, ref 554722), washed twice with Perm/Wash buffer (Bd Bioscience) and stained with an anti-human CD3 FITC antibody (Bd Bioscience ref 557694) for 30 minutes on ice. PBMC were then washed twice with Perm/Wash buffer and permeabilized in BD Perm Buffer Ill (Bd Bioscience, ref 558050) for 30 minutes. Cells were then washed twice in FACS buffer (and/or PBS with 1% BSA and 0.1% azide) and incubated for 30 minutes at room temperature with anti-human pSTAT5 Alexa 647 antibody (BD Bioscience, ref 612599). Samples were analyzed on BD CANTO II FACS instrument. As shown in FIG. 1 and FIG. 2, N13B2 and chimeric antibodies derived therefrom (N13B2-G1 and N13B2-G4) are strong inhibitors of STAT5 phosphorylation; with more than 50% inhibition at concentrations as low as 50 ng/ml and more than 80% (for 0.1 ng/ml of IL-7) or more than 90% (for 5 ng/ml of IL-7) inhibition at antibody concentrations as low as 100 ng/ml.

Example 4. Half-Inhibitory Concentration (IC50) of Different Anti-Human IL-7Rα Monoclonal Antibodies are Displayed in Table 1

TABLE 8

IC50 of different anti-CD127 antibodies on P-STAT5 induced by 100 pg/ml of rhIL 7

| IC50 | N13B2 | N13E5 | N13K12 | MD707-3 | N13B2-G1 | N13B2-G4 |
|---|---|---|---|---|---|---|
| pg/ml | 43 | 50 | 62 | 1090 | 28 | 37 |

Example 5. IL7R Internalization Assay by Cytofluorometry

The internalization assay could be performed using a confocal microscope as detailed in the material and method of Henriques et al (2010) and Luo et al. (2011). To observe the internalization of the CD127 in the absence of IL-7, antibodies hN13B2, HAL clone H3L4 (U.S. Pat. No. 8,637,27) or 1A11 (international patent application WO2011094259) at a final concentration of 50 ng/ml (or antibodies MD707-5, MD707-12, MD707-13 or N13B2-G4 at a final concentration of 10 μg/ml, were incubated with human PBMC (100000 cells/well) in serum-free medium (TexMACS, Miltenyi Biotec) for 30 min at 4° C. or 37° C. To observe the internalization of the CD127 in the absence of IL-7, the same pre-incubation conditions were used at 37° C. with antibodies and cells were then stimulated with recombinant IL7 (AbD Serotec, ref PHP046) at 0.1 ng/ml for 15 min at 37° C. The reaction was stopped at 4° C., and the cells were washed 3 times with PBS-1% BSA-0.1% azide before staining with PE-labelled anti-CD127 (clone hIL7R-M21, BD Bioscience, ref 557938) diluted at 1/10 in PBS-1% BSA-0.1% azide and incubated 15 min at 4° C. After washing, cells were analysed by cytofluorometry with Cantoll cytometer (BD Biosciences). Results presented in FIG. 16 are representative of three independent experiments.

This method is readily adaptable in 96 well plates in order to perform a screening and to select antibodies that block the IL7-dependent or -independent CD127 internalization.

Example 6. Anti-CD127 Antibody Affinity Study

The affinity of the anti hCD127 antibody was measured by surface plasmon resonance on a Biacore 3000 (GE Healthcare)

A CM5 chip (GE healthcare) was activated by injection of NHS/EDC mix for 7 min. The CD-127Fc (500 μg/mL) was diluted in 5 mM maleate buffer pH6.2 was injected and the succinimide ester residues until a hooking 300RU signal. The free reactive residues were inactivated by the injection of 1M ethanolamine pH8.5. Antibodies were injected over the immobilized CD 127 in the concentration range specified in the results section. The injection rate was set at 40 μL/min, the association was measured for 3 min and dissociation for 10 min. Between each cycle of the analysis, the chip was regenerated by injection of a solution of 5M MgCl2 for 60 s.

The obtained sensorgrams were analyzed with model "Bivalent analyte" on BIAeval 4 software.

Figure 3:
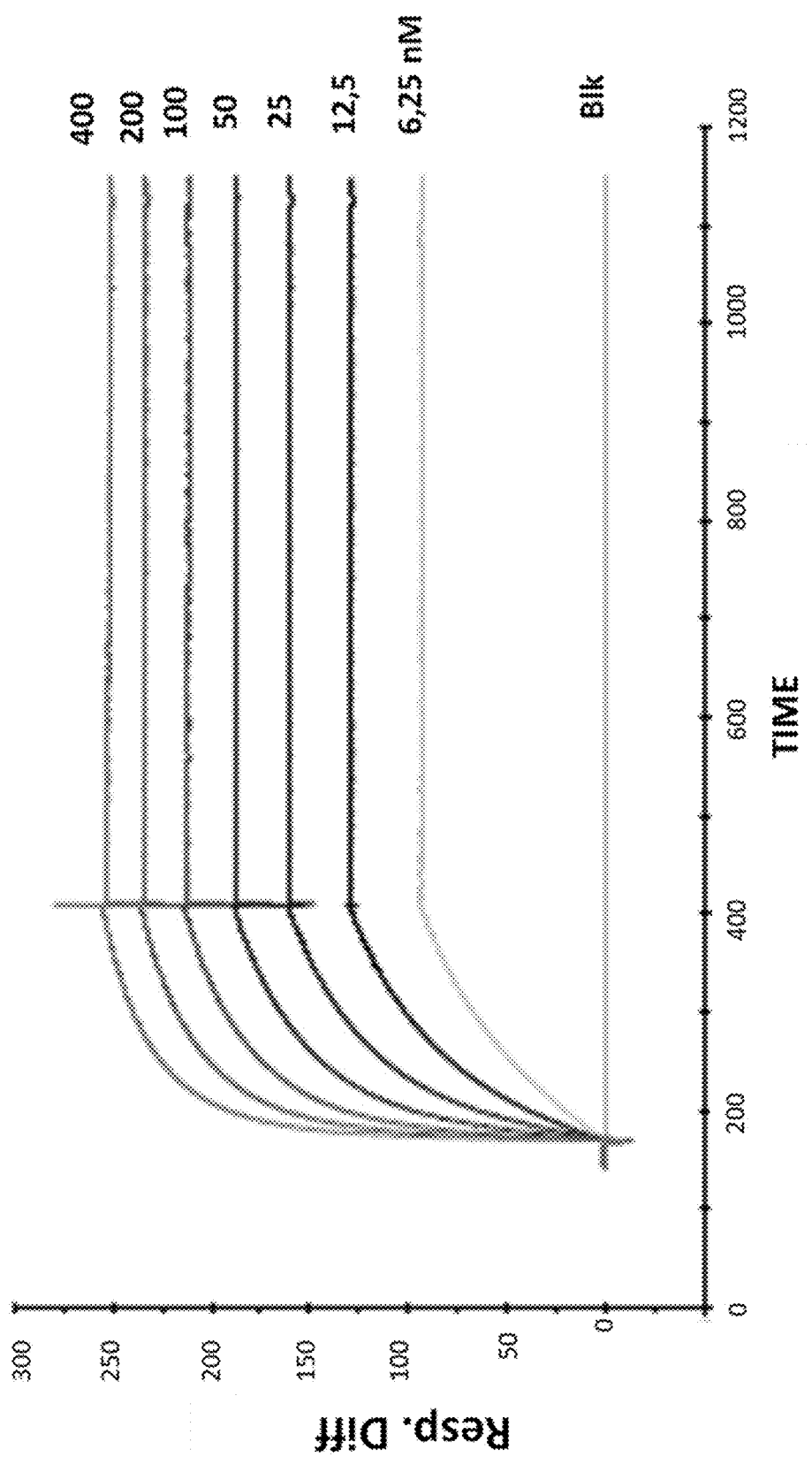
FIG. 3. (A) Binding studies of rat N13B2 anti-CD127 antibody. N13B2 antibody or MD707-1 were injected on a CD127 immobilized antigen at different concentration. Resp. diff: Response difference. Time: time in sec (total duration: 20 min). Blk: blank (no antibody). The association and dissociation curves were analyzed with model "Bivalent analyte" on BIAeval 4 software. Results are presented in the Table 1 below.

As shown in FIG. 3 and Table 2 therein, the N13B2 from rat and chimerized displayed a high affinity for CD127, with a KD in the range 4.9E-11 M-8.E-11 M (N13B2 from rat), 3.77.E-10 (N13B2-G1) and 1.70.E-10 (N13B2-G4). MD707-1 antibody from rat showed a lower affinity to CD127 than the N13B2 from rat.

Example 7. Anti-CD127 Antibody Binding Activity

For sandwich ELISA, donkey anti-human IgG (Fc specific) antibody was coated at 1.2 μg/ml on P96-plate and purified antibodies were added to measure concentration in function of standard range. After incubation and washing, mouse anti-human light chain, kappa specific, (Abcam, reference ab79115 or Effimune, clone NaM76-5F3) plus peroxidase-labeled donkey anti-mouse (Jackson Immunoresearch, reference 715-036-151) antibodies were added and revealed by conventional methods.

The binding activity of the anti hCD127 antibody was assessed by ELISA (Enzyme-linked immunosorbent assay). For the ELISA assay, recombinant hCD127 (Sino Biologicals, Beijing, China; reference 10975-H08H) was immobilized on plastic at 1 μg/ml and purified antibody were added to measure binding. After incubation and washing, peroxidase-labeled mouse anti-rat kappa chain (AbdSerotec) was added and revealed by conventional methods.

As shown in FIG. 4 and Table 3, the binding activity as measured by ELISA of the N13B2 antibody is high, with an ED50=65.6 ng/mL (ED50<75 ng/ml and ED50<100 ng/ml) for the rat N13B2 anti-hCD127 antibody and an ED50 of 12.0 ng/ml and 12.6 ng/ml (ED50<15 ng/ml) for two chimeric antibodies derived from N13B2 (cN13B2-G1 and cN13B2-G4).

Example 8. Stability Assay

Humanized and chimeric purified N13B2-G1 were incubated at 37° C. or at −80° C. for 7 days. Two assays were used to measure stability of antibody: binding anti-CD127 by ELISA assay, and aggregate formation by gel filtration. For activity ELISA assay, recombinant hCD127 (Sino Biologicals, Beijing, China; reference 10975-H08H) was immobilized on plastic at 1 µg/ml and dilutions of supernatant were added to measure binding. After incubation and washing, mouse anti-human light chain (kappa specific) plus peroxidase-labeled donkey anti-mouse antibodies were added and revealed by conventional methods. For analysis of aggregate formation, sample was analysed on gel filtration chromatography column (Superdex 200, 10/300GL, GeHealthcare) to separate and evaluate aggregate and monomer from samples.

Example 9. TSLP-Induced Production of TARC and Expression of the Matured Dendritic Cell Markers CD80 and CD40

Myeloid dendritic cells (DC) were isolated with CD1c (BDCA-1)+ Dendritic cell isolation kit (Miltenyi Biotec, Bergisch Gladbach, Germany) from blood of healthy volunteers (Etablissement Français du Sang, Nantes, France). Myeloid dendritic cells were cultured in RPMI containing 10% fetal calf serum, 1% pyruvate, 1% Hepes, 1% L-glutamine and 1% penicillin-streptomycin. Cells were seeded at 5.104 cells/well in flat-96-well plates, in the presence of TSLP (15 ng/ml), LPS (1 µg/ml) or culture medium alone, and addition of rat anti-human CD127 antibodies at different concentrations. At 24 hours of culture, cells were analyzed by flow cytometry for CD80 cell surface marker of maturation (anti-CD80-V450 (BD #560442) and supernatants were collected and analyzed for TARC production by ELISA assay (R&D systems, Minneapolis, USA).

The inhibition of TSLP-induced production of TARC was assessed by measuring said production as described above in the absence of antibody or in the presence of N13B2 or MD707-6 or commercial anti-TSLPR antibody (R&D systems ref. AF981) at 1 µg/ml or 6 µg/ml. As shown in FIG. 6, N13B2 inhibited TSLP-induced TARC production by more than 25% at concentrations as low as 1 µg/mL, i.e. as efficiently as MD707-6 at this concentration.

The inhibition of TSLP-induced expression of CD40 and CD80 cell surface markers were assessed by measuring said expression as described above (for CD40, antibody (anti-CD40-FITC from Beckton Dickinson ref. 555588) was used in similar conditions as those described above for CD80) in the absence of antibody (expression normalized at 100% for this condition) or in the presence of N13B2, MD707-3 or MD707-6 antibodies at 6 µg/ml. As shown in FIG. 7, both MD707-3 and MD707-6 induced an increase of CD40 and CD80 expression, while MD707-3 is a good inhibitor of STAT5 activation and a good binder of CD127 (FIG. 2 and FIG. 4) and MD707-6 is a strong inhibitor of TSLP-induced production of TARC (FIG. 6). The increase was at least 20% for CD80 and 50% for CD40. In contrast, the antibody of the invention, N13B2, did not increase TSLP-induced expression of CD40 or CD80. Instead, said expressions were lower in the presence of the TSLP and the antibody than in the presence of TSLP alone.

Example 10. Antibody-Dependent Cellular Cytotoxicity (ADCC) of Anti-Human CD127 Mabs ADCC refers to as the binding of an antibody to an epitope expressed on target cells and the subsequent Fc-dependent recruitment of effector immune cells expressing Fc receptors (essentially NK cells and activated lymphocytes), resulting in the killing of target cells mainly by granzyme/perforin-based mechanisms.

Effector cells were fresh primary human NK cells isolated from peripheral blood mononuclear cells by negative selection using magnetic beads (NK isolation kit, Miltenyi Biotec, Bergisch Gladbach, Germany) and an AutoMACS cell sorting instrument. NK cells were incubated over-night at 37° C., 5% CO2, in RPMI 1640 Medium (Life Technologies, Carlsbad, California) complemented with 10% FBS (Life Technologies), 100 IU/ml penicillin (Life Technologies), 0.1 mg/ml streptomycin (Life Technologies), 2 mM L-glutamine (Life Technologies) and 150 IU/ml of human IL-2 (Roche, Basel, Switzerland). The target cells (a human CD127-transfected BAF/3 cell line (Park et al., 2000)) were labeled with 100 µCi (3.7 MBq) of 51Cr (PerkinElmer) for 1 h at 37° C. and washed five times with culture medium. Target cells were incubated with diluted antibodies or with excipient (culture medium) for 15 min at room temperature and 10 000 cells were placed in a 96-well U-bottom plate. Effector T cells were added at a 10:1 cell ratio (final volume: 200 µl) for a 4 hours incubation period at 37° C. A total of 25 µl of the supernatant was then harvested and counted in a gamma counter (Packard Instrument).

Both MD707-3 of rat origin and the chimeric N13B2-G1 (thus having an IgG1 type Fc domain) Mabs did elicit ADCC. The chimeric N13B2-G4 (having an IgG4 type Fc domain) did not show any ADCC activity and was used as a negative control. Interestingly, there is no direct correlation between affinity, binding and ADCC properties, indicating that ADCC properties could not be predicted from binding analyses.

Example 11. Nucleotides and Amino Acid Sequences of Anti-Human CD127 Mabs

VH and VL regions of the N13B2 clone were sequenced using the RACE PCR technology. Briefly, total RNA was extracted, reverse transcribed and the resulting cDNA was poly-adenylated at the 3' end of the molecules using dATP and the terminal transferase enzyme. A first 35-cycle PCR reaction was performed using an oligodT anchor primer and Herculease enzyme (Stratagene). A second 35-cycle PCR was performed using nested PCR anchor primers. The resulting PCR product was then TA-cloned in E. coli and after selection on ampicillin, resulting colonies were screened by restriction enzyme profiling and inserted cDNA sequenced.

Example 12. Humanization

The humanization of rat N13B2 monoclonal antibody was accomplished using the standard CDR-grafting technology. The principle of this method is to reshape a human antibody so that it contains only the complementarity determining regions (CDRs) from the rat monoclonal antibody aiming to not only reduce antibody immunogenicity in humans but also improved biophysical properties of the CDR-grafted molecule.

Humanization by CDR-grafting requires that the antigen-binding residues from the parental rat antibody are retained in the humanized version. Residues adjacent to CDRs, termed "Vernier" residues, were found to affect CDR conformations and to fine-tune antigen recognition. Chothia and Lesk, (1987) segregated CDR conformations according to "canonical" residues, some of which are located within the CDRs themselves, others in the framework regions. The identification of these "Vernier" and "canonical" residues is therefore a critical step. The protocol used is based on the approach pioneered by Greg Winter and colleagues (Paus and Winter, 2006) at the Medical Research Council, Cambridge, UK and uses Kabat-defined CDR-residues.

The selection of human framework acceptor regions onto which the rat N13B2 CDR regions are grafted was accomplished by searching the IMGT rat and human V genes database using IgBLAST—a tool developed at NCBI to facilitate analysis of immunoglobulin variable region sequences (http://www.ncbi.nlm.nih.gov/igblast; Ye et al., 2013) with the rat N13B2 VH and VL sequences as input. Besides, the strategy here applied uses human germline sequences which are natural human sequences not containing the somatic hypermutations found in the protein and cDNA-derived sequences. Germline genes most similar to the rat VL and VH sequences were usually selected. Human germline framework acceptor VH and VL regions were identified by parental N13B2 VH and VL antibody sequences alignment and based on the following criteria: 1. Sequence identity across the framework and CDRs as defined by Kabat, 2. Identical and compatible inter-chain interface residues, 3. Support loops with the parental CDR canonical conformations and Vernier residues.

A few different sequences of humanization were tested for N13B2 to choose the best one, which maintains binding and biological activity. For humanization variants of N13B2, variable sequence of humanized heavy chain (VH) of N13B2 antibody was cloned by EcoRV in pFuseCHIg-hG1e4 expression plasmid (Invivogen, Toulouse) containing CH1-CH2-CH3 domains of hIgG1, mutated at E333A to increase ADCC. The variable sequence of the humanized light chain (VL) of N13B2 antibody was cloned by BsiWI in pFuse2CLIg-hk expression plasmid (Invivogen, Toulouse) containing human CLkappa.

In COS cells, we have co-transfected, by lipofectamine method, plasmid containing VH-hFcG1 with plasmid containing VL-CLk. After 48-72 h incubation, supernatant was recovered and purified by affinity on Protein G chromatography (HiTrap, GeHealthcare) with glycine 0.1M pH 2.8 elution buffer. Purified antibody was dialyzed in PBS and concentrated. They were quantified by sandwich ELISA and tested in activity assay against CD127 antigen.

Example 13. Study of Anti-IL7Rα Antibodies on IL-7 on Different In Vivo Inflammatory Disease Models With the aim to examine the effect of an antagonist antibody in the induction of colitis in humanized NSG mice, we conducted a series of experiments in the TNBS model, which have shown a measurable effect. The use of haptens such as the TNBS (2, 4, 6, trinitrobenzene sulfonic acid) allows to induce an immunological model mimicking (Nancey et al., 2008). Colitis is induced in mice by intrarectal administration of TNBS (Sigma Chemical, L'Isle d'Abeau Chesne, France) dissolved in ethanol at day 0 in four humanized mice. Initially, the mice are anesthetized by inhalation of a gas mixture. On day 7, the animals were sacrificed under anesthesia by CO2 intoxication for several studies (data not shown). Some animals were sacrificed before day 7 because of their bad clinical score.

Two new groups of mice were therefore treated with either PBS or with injections of 210 µL at 0.7 mg/mL of an N13B2 anti-IL7Rα every 2 days starting the day before TNBS treatment. Similar analyses were performed to those made in the development of the model.

We then tested N13B2 antibody efficacy in a humanized graft-versus-host disease (GVHD) mice model. This model mimics a global inflammatory disease. Some 7 to 12 weeks old NOD/scid/IL-2Rγ-/- (NSG) mice (Charles River, L'arbresle, France) were irradiated (3Gy) and infused intraperitonealy (i.p.). with 50 million human PBMC from healthy donors as described previously by Poirier et al., 2012. Animals were then maintained in aseptic conditions and were monitored three time per week for weight evolution and clinical evaluation. A control group was left untreated after infusion of cells and a treatment group received, from day 0 and three times per week, i.p injections of 5 mg/Kg of chimeric N13B2 mAb. GVHD diagnosis was given to a mouse upon a 20% weight loss. Animals found to have more than 25% weight loss, and animals surviving after 100 days from day 0 were euthanized. After euthanasia, colon, intestine, liver and lung tissues were frozen in liquid nitrogen and Tissu-tek for histological analysis. Frozen sections (10 µm) from these tissues were air dried at room temperature for 1 h before acetone fixation for 10 min at room temperature and then stained with hematoxylin and eosin solution. Results are presented in FIG. 25 and FIG. 26.

Example 14. Analysis of Various Clinical Parameters

Survival (FIG. 9A): we assessed the survival rate according to the chemical treatment and the use of the anti-IL7Rα antibody. The percentage of survival tends to be more important for the Hu-TNBS+IL7Rα group than for Hu-TNBS+PBS group (FIG. 9A). Indeed, we observed that 100% of the mice of Hu-TNBS group+IL7Rα survive up to 5 days while in the Hu-TNBS+PBS group, three animals had to be euthanized before J5.

Weight (FIG. 9B): in the TNBS treated groups from day 0 of the intra rectal injection of 5% TNBS/ethanol 50%, we observed a decrease in weight up to 20% for both groups. However, in the Hu-TNBS+IL7Rα group, the animals gained weight from J3 while in the Hu-TNBS+PBS group, weight loss continued (FIG. 9B). It is important to note that the mice had to be sacrificed to collect biological data and a protocol in the longer term would confirm the weight regain.

Survival (FIG. 25): we assessed the survival rate according to injection of human PBMC (GvHD development) and the use of the anti-IL7Rα antibody N13B2. The rate of surviving animals is 30% better when animals are treated with antibody than in control animals (100% death rate of control animals after 60 days). This results shows that the N13B2 antibody protects against GvHD and death.

Tissues infiltrate (FIG. 26): colon, intestine, liver and lung from dead and surviving animals (but euthanized) treated or not were histologically analyzed for their inflammatory cell infiltrate rate (histological score was determined). We observed that the colon of the animal treated with N13B2 contained less cell infiltrate than the control. No difference was observed in intestine, liver and lung between both conditions.

Animals treated with the N13B2 showed 30% survival rate compared to the control. The cell infiltrate characterizing the inflammation is unmodified by the treatment in the intestine, liver and lung tissues showing that in this model of inflammation the N13B2 does not protect against the inflammation in these tissues. However, N13B2 induced a 50% decrease of the cell infiltrate in colon. This effect could be correlated with the activity of the N13B2 antibody on α4β7 integrin expression as presented FIGS. 19 and 20. Indeed, α4β7 integrin is known to play an important role in homing of activated lymphocytes to the gut. So the decrease of the expression of the integrin induced by N13B2 antibody may be responsible for the decrease of cell infiltrate observed in the colon (FIG. 26). It should be emphasized that the apparent absence of protection in other tissues could be specific to the model used here, and should not lead to the conclusion that the protective effect of the antibody is limited to the colon. In particular, the much higher survival of treated animals shows that the protective effect of the antibody has a strong positive impact on the overall condition of the animals.

Example 15. In Vivo Efficiency of Non-Internalized CD127 Antibody

Animals

Baboons (*Papio anubis*, from the CNRS Primatology Center, Rousset, France) were negative for all quarantine tests, including a tuberculin skin test. Animals were housed at the large animal facility of our laboratory following the recommendations of the Institutional Ethical Guidelines of the Institut National de la Santé Et de la Recherche Médicale, France. All experiments were performed under general anaesthesia with Zoletil (Virbac, Carron, France). Pharmacokinetic and pharmacodynamic studies were performed during DTH experiments on five baboons receiving an i.v. bolus of either 10 mg/kg of N13B2-IgG1 or N13B2-IgG4 or MD707-13-IgG4.

BCG Vaccination and DTH Assay

According to Poirier et al, (Poirier et al., 2011), Baboons were immunized intradermally (i.d.) twice with a bacillus Calmette-Guérin (BCG) vaccine (0•1 ml; 2-8 ¥ 105 UFS; Sanofi Pasteur MSD, Lyon, France) in the upper region of the leg, 4 and 2 weeks before the DTH skin test. To investigate antigen-specific T cell immunity before DTH skin testing, successful immunization was confirmed by interferon (IFN)-g enzyme-linked immunospot (ELISPOT) assay (non-human primate IFN-g ELISPOT kit; R&D Systems, Minneapolis, MN, USA) on freshly isolated PBMC, according to the manufacturer's instructions. Intradermal reactions (IDR) were performed with duplicate intradermal injections of two doses (1000 UI or 2000 UI) of tuberculin-purified protein derivative (PPD; Symbiotics Corporation, San Diego, CA, USA) in 0.1 ml in the skin on the right back of the animals. Saline (0.1 ml) was used as a negative control. Dermal responses at the injection sites were measured using a caliper square. The diameter of each indurated erythema was measured by two observers from days 3-8, and were considered positive when >4 mm in diameter. The mean of the reading was recorded. Skin biopsies from the DTH or control (saline) site were performed at day 4 on one duplicate and placed in Tissue Tek optimal cutting temperature (OCT) compound (Sakura Finetek, Villeneuve d'Ascq, France) for immunohistochemical analysis. A second IDR was performed after a 3-week washout period and animals received one i.v. injection of either 10 mg/kg of chimeric CD127 antibodies (N13B2-IgG1 or N13B2-IgG4 or MD707-13-IgG4) 1 day before this second challenge with PPD. A third IDR was performed after a further 3-6-week washout period and animals were left untreated. In some cases, a fourth IDR was performed after another 3-month washout period and animals were also left untreated.

Example 16. α4β7 Expression at T Cell Surface In Vitro and In Vivo on Mice Model To measure IL7 induced α4β7 expression at the T cell surface, human T-lymphocyte were stimulated for 9 days at 37° C., with IL7 (AbD Serotec, ref PHP046) at 5 ng/ml. Reaction was stopped a 4° C., and washed before stained with PerCP/Cy5-labelled anti-α4 (BD Bioscience 563644 clone 9F10) and PE-labelled anti-β7 (BD Bioscience, clone FIB504). Positive cells for α4 integrin and then β7 positive cells were measured by flowcytometry. N13B2 humanized antibody was added at day 0 to the cell culture at different concentration from 0.01 to 20 ug/ml In-vivo, $40\times10^6$ human peripheral blood mononuclears cells were injected intraperitonealy in irradiated immuno-deficient mice (NOD/SCID/IL-2 receptor gamma-chain knock-out mice). Two weeks after treatment with control buffer (n=5) or N13B2 mAb (5 mg/kg, n=5), the percentage of β7-positive T lymphocytes in the blood was measured by flow cytometry and engraftment of β7-positive human T lymphocytes was measured by flow cytometry. This engraftment was measured by flow cytometry by discriminating human CD45 positive cell from mouse CD45 positive cells using specific antibodies (PECy7 anti-humanCD45 from BD reference 57748 and PerCPCy5.5 anti-mouse CD45 from BD reference 550994) then human 37 positive cells were analysed (BD Bioscience, clone FIB504).

Example 17. Antibody Profiling Using Peptide Microarray

The peptide Technologies' PepStar™ peptide microarrays comprise purified synthetic peptides derived from antigens or other sources that are chemoselectively and covalently immobilized on a glass surface. An optimized hydrophilic linker moiety is inserted between the glass surface and the antigen-derived peptide sequence to avoid false negatives caused by sterical hindrance. For technical reasons all peptides contain a C-terminal glycine. Profiling experiments of samples were performed on a peptide library consisting of 52 peptides. The complete list of peptides is shown below:

TABLE 9

List of peptides used in peptide microarray assays

| SEQ ID | Sequence | SEQ ID | Sequence | SEQ ID | Sequence |
|---|---|---|---|---|---|
| 58 | ESGYAQNGDLEDAEL | 76 | FIETKKFLLIGKSNI | 94 | HDVAYRQEKDENKWT |
| 59 | AQNGDLEDAELDDYS | 77 | KKFLLIGKSNICVKV | 95 | YRQEKDENKWTHVNL |
| 60 | DLEDAELDDYSFSCY | 78 | LIGKSNICVKVGEKS | 96 | KDENKWTHVNLSSTK |
| 61 | AELDDYSFSCYSQLE | 79 | SNICVKVGEKSLTCK | 97 | KWTHVNLSSTKLTLL |
| 62 | DYSFSCYSQLEVNGS | 80 | VKVGEKSLTCKKIDL | 98 | VNLSSTKLTLLQRKL |
| 63 | SCYSQLEVNGSQHSL | 81 | EKSLTCKKIDLTTIV | 99 | STKLTLLQRKLQPAA |
| 64 | QLEVNGSQHSLTCAF | 82 | TCKKIDLTTIVKPEA | 100 | TLLQRKLQPAAMYEI |
| 65 | NGSQHSLTCAFEDPD | 83 | IDLTTIVKPEAPFDL | 101 | RKLQPAAMYEIKVRS |
| 66 | HSLTCAFEDPDVNTT | 84 | TIVKPEAPFDLSVIY | 102 | PAAMYEIKVRSIPDH |
| 67 | CAFEDPDVNTTNLEF | 85 | PEAPFDLSVIYREGA | 103 | YEIKVRSIPDHYFKG |
| 68 | DPDVNTTNLEFEICG | 86 | FDLSVIYREGANDFV | 104 | VRSIPDHYFKGFWSE |
| 69 | NTTNLEFEICGALVE | 87 | VIYREGANDFVVTFN | 105 | PDHYFKGFWSEWSPS |
| 70 | LEFEICGALVEVKCL | 88 | EGANDFVVTFNTSHL | 106 | FKGFWSEWSPSYYFR |
| 71 | ICGALVEVKCLNFRK | 89 | DFVVTFNTSHLQKKY | 107 | WSEWSPSYYFRTPEI |
| 72 | LVEVKCLNFRKLQEI | 90 | TFNTSHLQKKYVKVL | 108 | SPSYYFRTPEINNSS |
| 73 | KCLNFRKLQEIYFIE | 91 | SHLQKKYVKVLMHDV | 109 | YFRTPEINNSSGEMD |
| 74 | FRKLQEIYFIETKKF | 92 | KKYVKVLMHDVAYRQ | | |
| 75 | QEIYFIETKKFLLIG | 93 | KVLMHDVAYRQEKDE | | |

A total of 9 samples were incubated on microarray slides using a Multiwell-format. For N13B2 antibody and the other samples, 4 different concentrations were applied (10, 1, 0.1 et 0.01 µg/ml). One negative control incubation (secondary antibody only) was performed in parallel. Human and mouse IgG proteins were co-immobilized alongside each set of peptides to serve as assay controls. All incubations were performed in parallel using two slides. Two peptide-mini-arrays on each slide were used as a control incubation by applying the fluorescence labelled detection antibody alone to assess false-positive binding to the peptides. After washing and drying of the slides they were scanned with a high-resolution laser scanner at 635 nm to obtain images of fluorescence intensities. The images were quantified to yield a mean pixel value for each peptide. Secondary antibody anti-rat IgG (JIR 212-175-082) labeled with Cy5 at 1 µg/ml. Buffers and solutions The buffer used were TBS-buffer including 0.05% Tween20 (JPT) and Assay buffer T20 (Pierce, SuperBlock TBS T20, #37536). Acquisition and analysis were performed using Peptide microarrays (JPT Peptide Technologies GmbH, Berlin, Germany; batch #2668, Multi-Well incubation chamber, Axon Genepix Scanner 4200AL, Spot-recognition software GenePix and Microsoft Excel, R Example 18. Epitope Mapping by Mass Spectrometry Analysis Mass spectrometry was used to identify a conformational epitope. Sequencing of the epitope was done using a MALDI mass spectrometer. This instrument allows a peptide sequence between 800 and 4000 Da. Digestion of the protein of interest allows cutting the protein into small fragments (potential epitopes). Ideally, the digestive enzyme must cut as close as possible to the borders of the epitope. Choosing the digestion enzyme is to be made according to the enzyme cutoff frequency in the sequence of the recombinant protein. A second digestion is considered to reduce the size of the epitopes obtained at the end of the first digestion. Depending on the selected enzyme, the profiles differ significantly. The enzyme having the best distribution of digests on the sequence is chymotrypsin. A second enzyme with a proper cut-off frequency and well distributed on the sequence of interest is Glu C.

Since the epitope is conformational, preference is given to the digestion of the complex during affinity chromatography. The identification of the sequence of interest is based on the protection of the epitope against enzymatic digestion by the formation of antigen-antibody complex. After passage through affinity chromatography and digestion, the fragments of the epitope are eluted and sequenced by mass spectrometry (MALDI-TOF-TOF Bruker). The 3D structure of the protein of interest is available and is compared to the results obtained.

Uniprot P16871 [21-239] (Seq ID No: 114): corresponds to the Topological domain of the *Homo sapiens* Interleukin-7 receptor subunit alpha:

ESGYAQNGDLEDAELDDYSFSCYSQLEVNGSQHSLTCAFEDPDVNTTNL

EFEICGALVEVKCLNFRKLQEIYFIETKKFLLIGKSNICVKVGEKSLTC

KKIDLTTIVKPEAPFDLSVIYREGANDFVVTFNTSHLQKKYVKVLMHDV

AYRQEKDENKWTHVNLSSTKLTLLQRKLQPAAMYEIKVRSIPDHYFKGF

WSEWSPSYYFRTPEINNSSGEMD

In silico, CD127 digestion enzyme choices (see underlined amino acids above in the sequence corresponding to Seq ID No:114): Chymotrypsin was chosen as a digestion enzyme. The cutting sites (bold lines), the peptide number, the frequency of the cuts are suitable. Glu-C enzyme was chosen as a second digestion enzyme. The number of peptides obtained with a weight comprised between 800 and 4000 Da is suitable. The frequency of Glu-C cuts and the location of cutting sites (thin line) are suitable. The procedure used is conventional and well-known to the skilled person and is described in Suckau et al, 1990 and Papac et al, 1994.

Material and Reagents: Masse spectrometry MALDI-TOF/TOF II de Bruker; Hi-trap NHS columns (Ref: 17-0716-01-GE healthcare); Chymotrypsine (Ref: 11418467001-Roche); Glu C (Ref: 11420399001-Roche); Zip/TIP C18 (Ref: ZTC18S096-Millipore); Ammonium bicarbonate (Ref: 09830-Sigma); Glycine (Ref: G7126-Sigma); NaCl (Ref: 27800.360-VWR).

Phase 1: Digestion of the free protein and antibody in solution. Digestion in solution of free antigen and antibody by chymotrypsin or Glu C for 1 h, 2 h, 3 h, 4 h, 5 h and overnight at room temperature or 37° C. The analysis of the digested peptides was performed by Mass spectrometric (MS) of the digested peptides. These experiments allow to establish the suitable conditions of enzymatic digestions (time and temperature). The aim is to have sufficient digestion of the antigen, while impacting the structure of the antibody as little as possible. Optimal conditions were determined to be: Chymotrypsin digestion: 1 hour at room temperature; Glu-C digestion: overnight at 37° C. Each digest of the antigen and antibody is analyzed by mass spectrometry MALDI-TOF/TOF.

Phase 2: Total digestion of the complex whole tied Ac+whole antigen. The coupling of the anti-CD127 monoclonal antibody N13B2-G1 (batch 210415) was performed on of Hi-Trap NHS column following the standard procedure. The antigen immunocapture on the column was performed during 1 h, allowing the formation of antigen-antibody complex. N13B2-G1 Antibody coupling efficiency on the four columns Hi-Trap NHS ware as follows: 84%, 84%, 83% and 83%. Consistent and identical coupling yields were obtained.

Digesting the complex was performed in the ratio 1/50, or 1 mg of enzyme for 50 mg of antibody, at a temperature and for the duration determined by the controls mentioned above. The column is then washed with the wash buffer (ammonium bicarbonate 25 mM) to remove and recover the unbound antigen peptides. A washing step in buffered saline (PBS-2M NaCl) is also performed to remove nonspecific peptides. After washing, elution is performed with an eluting solvent (50 mM Glycine pH 2) to specifically extract and recover the specifically bound peptides (which are predicted to correspond to the epitope).

MALDI Analysis: washing and elution fractions are concentrated by hydrophobic chromatography on a C18 matrix. They are then analyzed by mass spectrometry MALDI-TOF/TOF. MS analysis can precisely measure the mass of peptides and comparing the experimental masses with the theoretical masses of peptides derived from the digestion in silico of the free antigen allows identification of the peptides; MS/MS analysis can be performed to confirm the sequence of a peptide if necessary.

The spectrum of the eluate after chymotrypsin digestion reveals the presence of peptides with a mass of: 912.49; 1086.47; 1843.03; 2104.16; 1944.97; 1564.73; 1835.97; 2022.05; 2424,22et 2858.42 Da, which may correspond to antigen peptides in Table 10 below.

TABLE 10

Peptides obtained after chymotrypsin digestion (sequences protected from proteolysis)

| Mass (Da) | Sequence | SEQ ID No: |
|---|---|---|
| 912.49 | FIETKKF | 115 |
| 1843.03 | RKLQEIYFIETKKF | 118 |
| 2104.16 | NFRKLQEIYFIETKKF | 119 |
| 1944.97 | DLSVIYREGANDFVVTF | 120 |
| 1564.73 | VVTFNTSHLQKKY | 121 |
| 1835.97 | EIKVRSIPDHYFKGF | 122 |
| 2022.05 | EIKVRSIPDHYFKGFW | 123 |
| 2424.22 | EIKVRSIPDHYFKGFWSEW | 124 |
| 2858.42 | EIKVRSIPDHYFKGFWSEWSPSY | 125 |
| 1086.47 | FKGFWSEW | 126 |

The spectrum of the eluate after Glu-C digestion reveals the presence of digestive peptides of our protein of interest with a mass of 1200.43; 1309.68; 2108.97; 2191.04; 2699.43; 3170,68et 3264.70 Da may correspond to the antigen peptides in Table 11 below.

TABLE 11

Peptides obtained after Glu-C digestion
(sequences protected from proteolysis)

| Mass (Da) | Sequence | SEQ ID No: |
|---|---|---|
| 2699.43 | IYFIETKKFLLIGKSNICVKVGE | 127 |
| 3264.70 | KSLTCKKIDLTTIVKPEAPFDLSVIYRE | 128 |
| 2191.04 | LTTIVKPEAPFDLSVIYRE | 129 |
| 1309.68 | APFDLSVIYRE | 130 |
| 3170.68 | NKWTHVNLSSTKLTLLQRKLQPAAMYE | 131 |
| 2108.97 | IKVRSIPDHYFKGFWSE | 132 |

The two digestions allowed us to identify three sites (Table 12 below) involved in the interaction between hN131B2 and CD127 antigen. Peptides derived from the salt buffer washes were excluded to restrict the sequences of interest.

TABLE 12

Sequences of the human CD127 peptides protected
by N13B2 against proteolysis

| | | |
|---|---|---|
| A (SEQ ID No: 115) | | FIETKKF |
| B (SEQ ID No: 116) | | DLSVIY |
| C (SEQ ID NO: 117) | | FKGF |

The epitope mapping of the N13B2 antibody on the antigen CD127 showed 3 different sequences important for the antibody activity on IL7/CD127 pathway (FIG. 27). With the 3D crystallography analysis of the IL7/CD127 interaction (McElroy et al, Structure 2009, PDB:3DI2), two of the sequences (Seq ID N° 115 and ID N° 117) are structurally closed and are located in the region involved in the binding of the IL7 with CD127. The third identified sequence (seq ID N° 116) is located in the site 2b of the D2 domain of the receptor, domain predicted to interact with CD132, the gamma chain of the receptor (Walsh et al, 2012). N13B2 recognizes a conformational epitope on CD127 located in 2 parts of the protein that inhibits the IL7-CD127 interaction and the CD127-CD132 heterodimer formation. The binding of the N13B2 must destabilize the formation of the "ternary IL7Ra/IL7/g-chain complex" as predicted by Walsh ST, which block the internalization of the complex.

Example 19. Results

As previously described (Henriques et al., 2010), IL-7 alone induces rapid internalization (30-40%) of IL-7 receptor alpha chain (CD127) at the surface of T lymphocytes, which is required for IL-7 mediated signaling. Here we described that N13B2 mAb prevents the IL-7-induced internalization of CD127 and does not induce this internalization by itself (FIG. 16). In contrast, we described that anti-human CD127 1A11 clone from GSK (patent application WO2011094259) dramatically decreases the expression of CD127 at the surface of T lymphocytes when applied alone or in combination with IL-7 at 37° C. (FIG. 16). This effect was observed using different staining with several commercial anti-IL7R antibodies (eBioRDR5 and MB15-18C9, data not shown). After intravenous administration of chimeric N13B2 mAb (formatted with a human IgG1 or IgG4 Fc-domain) at 10 mg/Kg in non-human primates, we did not measure reduction of CD127 expression at the surface of T-lymphocytes over a 2-week period of follow-up (FIG. 17B). In contrast, in other non-human primates treated in parallel intravenously with 10 mg/kg of the anti-human CD127 MD707-13 clone (formatted with human IgG4 Fc-domain; WO2013/056984), we observed a significant decrease (60%) of CD127 at the surface of T-lymphocytes (FIG. 17B). This internalization of CD127 after binding of anti-human CD127 mAb on T-lymphocytes, was also previously published by a Pfizer group, where they described that their anti-human CD127 mAb (clone HAL-H3L4, U.S. Pat. No. 8,637,273) significantly induces CD127 internalization ex-vivo on human and non-human primate blood cells, as well as in-vivo after intravenous administration in non-human primates (Kern et al., 2013).

In a recent publication by Kern et al. (Kern et al., 2015), the CD127 occupancy was studied and competition assays were performed. The anti-CD127 HIL-7R-M21 clone from BD biosciences was shown to compete with HAL/Ab1 antibody (from Pfizer group) for the binding to CD127. As shown in FIG. 16 of the present invention, the HAL antibody (clone H3L4, U.S. Pat. No. 8,637,273) was compared to N13B2 and 1A11 in terms of CD127 expression and internalization. These results showed a competition between the HAL antibody and the HIL-7R-M21 patent, confirming the data of Kern et al, 2015. However, N13B2 does not compete with HIL-7R-M21. Kern et al. also showed that HAL/Ab1 by itself induces an in vivo down regulation of CD127 expression at the cell surface from 4 to 8 days after injection. Those results are comparable with the results presented FIG. 17B of the present invention with the MD707-13 clone. FIG. 17B shows a down regulation of CD127 expression at the cell surface 4 to 10 days after injection of the antibody. This in vivo effect can be correlated with the in vitro MD707-13-dependent internalization of CD127 into the cell observed as well.

The epitope study by peptide microarray and mass spectrometry identified a conformational epitope recognized by N13B2 on CD127. This epitope is located in domains D1 and D2, in contrast with the antibodies of the prior art which recognize an epitope located only in D1 (Example 17). Furthermore, FIG. 16 shows that prior art antibodies induce internalization of CD127, while N13B2 does not. We therefore conclude that the property of the N13B2 not to induce the CD127 internalization is correlated with its property to recognize an epitope located in both domains D1 and D2.

Altogether, these results and previous reported showed that anti-human CD127 mAbs (1A11 clone, HAL/Ab1 and H3L4 clones and MD707-13 clone) described to block the binding of IL-7 on IL-7 receptor, also induce IL-7 receptor alpha chain internalization which was associated and required for IL-7 receptor signaling. In contrast and in a surprising manner, N13B2 mAb has the unique property not to induce CD127 internalization and it prevents such internalization induced by IL-7. These results have to be correlated with the observation that CD127-internalization inducer mAb (for example MD707-13 clone), which are effective in vitro to prevent IL-7 receptor signaling (for example STAT5 phosphorylation, FIG. 14B), are not able in vivo to prevent memory cellular (FIG. 21) or humoral (FIG. 22) immune responses. In contrast, we described that N13B2 mAb, which effectively blocks IL-7 receptor signaling (STAT5 phosphorylation) but does not induce CD127 internalization ex vivo on human T lymphocytes and in vivo in non-human primates, prevents delayed-type hypersensitivity memory cellular responses (FIG. 21) as well as immunization against xenogeneic sheep red blood cells (FIG. 22). While no difference was observed between isotype of N13B2 on the control of memory humoral response, we noticed that IgG4-formatted N13B2 was more effective to prevent memory cellular responses as compared to IgG1. No difference in term of mAb exposure and serum concentrations was observed between MD707-13-treated and N13B2-treated animals. Similarly, we observed also a significant increase of regulatory T lymphocytes in animals treated with either N13B2 or MD707-13 mAb (FIG. 22).

Human IL-7 induced strong expression of α4 and β7 integrins in vitro on human T lymphocytes and dramatically increased the frequency of human T lymphocytes expressing α4, β7 and α4/β7 integrins (FIG. 19A), which are required for T lymphocytes homing and retention in non-lymphoid tissues such as intestine, brain and skin (Gorfu et al., 2009, DeNucci et al., 2009). Accordingly, we observed that N13B2 mAb dose-dependently inhibits in vitro both expression of α4 and β7 as well as decreases the frequency of α4-positive and α4/β7-positive human T lymphocytes (FIG. 19B). Similarly, after transferred from human peripheral blood mononuclear cells into immunodeficient mice, we observed that the N13B2 antibody significantly and rapidly decreases the percentage of the β7-positive T lymphocytes as well as the number (i.d. engraftment) of these cells after one (data not shown) and two weeks of treatment (FIG. 20). Results obtained in two different models of inflammation show that the N13B2 anti-IL7Rα antibody could be an efficient treatment against inflammatory diseases and in particular in colitis.

Example 20. Generating a Conformational Epitope

CLIPS peptides may be used to adequately mimic the native secondary and tertiary structure of the antigen in the aim to translate these CLIPS peptides into active and potent immunogens that induce the desired antibodies (Boshuizen et al, 2014). The CLIPS technology involves the (multiple) cyclization of linear peptides via reaction with a small rigid entity (chemical scaffold) that carries 2, 3 or 4 anchor points. The anchors react exclusively with one type of functionalities of the peptide (i.e. thiols) and attaches to the peptide via multiple covalent bonds. The peptide folds around the scaffold and looses flexibility while slowly adopting a well-defined three-dimensional structure, with the scaffold entity in the center like the "spider in the web".

The technology makes use of fully synthetic, tailor-made scaffolds. CLIPS scaffolds vary mainly in size, polarity, rigidity, solubility, functionality, and 'SS-spanning' distance. These scaffolds are used to affix the loose ends of the peptide. When positioned appropriately within the peptide sequence, the resulting CLIPS peptide is likely to resemble much better the 3D-structure of the corresponding region on the intact protein as compared to the linear sequence. The CLIPS-cyclizations can be performed on native L-cysteine residues, but also on artificially introduced D- and L-(homo) cysteines at virtually any desired position in the sequence. Hence, the structure and dimensions of the CLIPSed peptides can be varied at will. The cyclization reaction lasts no longer than 30 min, runs at room temperature and does not require any sort of catalysis. Moreover, it can be applied under fully aqueous conditions and neutral pH (7.5-8.0) and is therefore compatible with highly sensitive biological systems, like bacterial phages. Finally, the reaction can be run at high-dilution conditions (10-100 μM), which promotes high yields of cyclic products and avoids polymerization. This technology is highly versatile, and unique for its ease of application.

In an attempt to reconstruct both linear and discontinuous epitopes for anti-receptor antibody, linear multi-mer overlapping peptides are synthesized directly onto credit-card-sized polypropylene plates with the C terminus covalently coupled to the bottom of each 3 ul well (455 wells per plate), and each well containing a different peptide. Within each of the single-domain peptides, a cyclized dicysteine bridge was formed to insert a constrained loop in the plate-attached peptides. Teeling et al, 2006, explain how to generate cyclized peptides with peptides of interest in the aim to reconstitute discontinuous epitope recognized by the antibody of interest. Briefly, plate-bound dicysteine containing peptides are first synthesized with cysteines spaced at between 4 and 13 aa along the peptide, for example, CXXXXC-plate, XXXCXXXXCXXXXXplate, or CXXXXC-plate, etc. The peptides are then cyclized by treating with a,a-dibromoxylene in aqueous solution to provide cysteine loops containing different numbers of amino acids. This chemical modification provides more stable loops, than do disulfide bridges. (Niederfellner et al, 2011)

Example 21. Co-Immunoprecipitation of CD127 and γc

To test the effect of the N13B2 and of prior art antibodies on the binding of CD127 to the γc chain, a coimmunoprecipitation experiment was performed in cells stimulated by IL-7 and incubated in the absence of antibodies or in the presence of MD707-13 or of N13B2 antibodies. In the absence of antibodies, CD127 and γc were shown to coimmunoprecipitate. The incubation of cells with MD707-13 did not prevent this coimmunoprecipitation, while the incubation with N13B2 led to the absence of such coimmunoprecipitation. Our antibody therefore is capable of disrupting the binding of CD127 to the γc chain, while antibodies of the prior art do not have such a feature.

To co-immunoprecipitate complex CD127-CD132-IL7 in presence of anti-CD127, human PBL were incubated with rat anti-hCD127 antibody (rat N13B2 or MD707-13 at 10 μg/ml) for 30 min at 37° C., before stimulating with IL7 (AbD Serotec, ref PHP046) at 5 ng/ml for 15 min at 37° C. Reaction was stopped at 4° C., and washed twice with cold-PBS before adding lysis buffer from co-immuprecipitation kit (Pierce Direct IP kit, ref 26148).

A purification column anti-human CD127 was prepared with the co-immuprecipitation kit (Pierce Direct IP kit, ref 26148). The column was coupled with 75 μg of a non-competing rat anti-human CD127 (Effimune, MD707-9), following the procedure recommended by the manufacturer. The lysate was pre-purified on a non-coupled column in order to remove unspecific binder. Then, lysate was added on the anti-CD127 column and incubated 2 h at 4° C., on rolling agitation. The column was washed twice with washing buffer, and then was eluted with elution buffer. Recovered sample were analysed by Western Blot.

For Western Blot, SDS-Page gel was prepared (10% for resolving, 4% for stacking gel, with 1.5 mm thickness) and 50 μl of denaturated eluate (for denaturation: DTT 0.1M and 10 min at 95° C.) was adding in each well. CD127Fc (Sino Biologicals, Beijing, China; reference 10975-H08H) and CD132Fc (Sino Biologicals, Beijing, China; reference 10555-H02H) recombinant protein was added (5 μg/well) as a control for western blot detection. After migration for 1 h30 at 200V, and transfer on nitrocellulose membrane for 35 min at 20V, saturation was performed for 2 h at room-temperature in 5% milk.

To start detection, rabbit anti-human CD132 antibody (anticorps-en-ligne, France, reference ABIN741840) is added at 1/50 overnight at 4° C., then revealed with peroxidase-labeled goat anti-rabbit (Jackson Immunoresearch, reference 111-035-144) at 1/2000 for 1 h at room-temperature. After dehybridization, the membrane was incubated with rat anti-human CD127 antibody (Effimune, MD707-9) at 1/200 overnight at 4° C., and revealed with peroxidase-labeled donkey anti-rat antibody (Jackson Immunoresearch, reference 712-035-153) at 1/1000 for 1 h at room-temperature. For each revelation, ECL (Thermo Scientific, reference 34080) was used to detect peroxidase by chemiluminescence, and the results was read on Fuji 4000 camera.

FIG. 28 shows the results of the co-immunoprecipitation of the CD127/IL7/CD132 complex. We observed that the CD132 chain (60 KDa) co-immunoprecipitates with CD127 in any conditions except when cells are incubated with the N13B2 antibody (28A). However, in each condition CD127 (70 KDa) is well immunoprecipitated by de MD707-9 antibody as shown by FIG. 28B indicating that N13B2 and MD707-13 did not compete with MD707-9 for the recognition of the CD127. The N13B2 antibody inhibits the complex formation of CD127/CD132 in the presence of IL-7. These results are consistent with the epitope mapping of the N13B2 antibody on CD127, showing that N13B2 binds an amino acid sequence within site 2b in domain D2 of the IL7R alpha chain (Walsh et al, Immunol rev. 2012).

Altogether these results showed that N13B2 antibody is an antagonist of the IL7/CD127 interaction as well as an antagonist of the CD127/CD132 interaction at site 2b in the presence of IL-7, which could explain the inhibitory activity of the antibody against the internalization of CD127 observed with IL7 and/or anti-CD127 antibodies from the prior art.

The Following Numbered Embodiments Constitute Preferred Embodiments of the Invention.

1. An antibody or an antigen-binding fragment of an antibody or an antigen-binding antibody mimetic which binds specifically to CD127 and does not induce the internalization of CD127.
2. An antibody or antigen-binding fragment or mimetic thereof, in particular according to embodiment 1, which inhibits IL7-induced internalization of CD127.
3. An antibody or antigen-binding fragment or mimetic thereof according to embodiment 1 or 2 wherein the cell surface expression of CD127 in IL-7 treated cells in the presence of antibody or fragment is at least 80%, preferably at least 90% of its level in cells incubated in the absence of antibody.
4. An antibody or antigen-binding fragment thereof which binds specifically to CD127 and thereby disrupts the binding of CD127 to the γc common chain of cytokine receptors.
5. An antibody or antigen-binding fragment thereof according to any of embodiments 1 to 3, which disrupts the binding of CD127 to the γc common chain of cytokine receptors when bound to CD127.
6. An antibody or antigen-binding fragment thereof according to any of embodiments 4 or 5, in the presence of which the amount of γc bound to CD127 is less than 80%, preferably less than 50%, even more preferably less than 25% or 10% of said amount measured in the absence of antibodies in otherwise identical conditions, in particular when said measurement is performed on cell lysates comprising CD127-containing molecular complexes from intact cells expressing the IL7 receptor at the cell surface, incubated in the presence or absence of said antibodies.
7. An antibody or antigen-binding fragment or mimetic thereof according to any of the above embodiments, which is an antagonist of IL-7R signaling induced by IL-7.
8. An antibody or antigen-binding fragment or mimetic thereof, in particular according to any of the above embodiments, which specifically binds and/or has been raised against an antigen according to any of embodiments 53 to 67 or the epitope of said antigen.
9. An antibody or antigen-binding fragment or mimetic thereof, which binds specifically to CD127, in particular according to any of the above embodiments, which does not increase the maturation of dendritic cells induced by TSLP.
10. An antibody or antigen-binding fragment or mimetic thereof according to any of the above embodiments which inhibits the expression of α4, β7 and/or α4/β7 integrins.
11. An antibody or antigen-binding fragment or mimetic thereof according to embodiment 10 which inhibits the expression of α4, β7 and/or α4/β7 integrins in vivo, in particular in human T cells injected in an immunodeficient mouse.
12. An antibody or antigen-binding fragment or mimetic thereof, which binds specifically to CD127, in particular according to any of the above embodiments, comprising a VH chain comprising at least one of the following amino acid sequences:
   VHCDR1 SEQ ID No:10;
   VHCDR2 SEQ ID No:12;
   VHCDR3 SEQ ID No:14 or SEQ ID No:48; or
   VH SEQ ID No:22
and/or a VL chain comprising at least one of the following amino acid sequences:
   VLCDR1 SEQ ID No:16 or SEQ ID No:50;
   VLCDR2 SEQ ID No:18 or SEQ ID No:52;
   VLCDR3 SEQ ID No:20; or
   VL SEQ ID No:24.
13. An antibody or a fragment or mimetic thereof according to embodiment 12 which comprises at least two, three, four or five CDR sequences selected from the group consisting in VHCDR1 SEQ ID No:10, VHCDR2 SEQ ID No:12, VHCDR3 SEQ ID No:14 or SEQ ID No:48, VLCDR1 SEQ ID No:16 or SEQ ID No:50, VLCDR2 SEQ ID No:18 or SEQ ID No:52 and VLCDR3 SEQ ID No:20.
14. An antibody or a fragment or mimetic thereof according to embodiment 13 which comprises all six CDR sequences VHCDR1 SEQ ID No:10, VHCDR2 SEQ ID No:12, VHCDR3 SEQ ID No:14 or SEQ ID No:48, VLCDR1 SEQ ID No:16 or SEQ ID No:50, VLCDR2 SEQ ID No:18 or SEQ ID No:52 and VLCDR3 SEQ ID No:20.
15. An antibody according to embodiment 14 wherein
   the VH chain consists in the VH chain with the sequence of SEQ ID No:2 or of SEQ ID No:6 or of SEQ ID No:54 or comprises the sequence of SEQ ID No:22 or of SEQ ID No:36 or of SEQ ID No:38 or of SEQ ID No:40; and
   the VL chain consists in the VL chain with the sequence of SEQ ID No:4 or of SEQ ID No:56 or comprises the sequence of SEQ ID No:24 or of SEQ ID No:42 or of SEQ ID No:44 or of SEQ ID No:46.

16. An antibody according to any of the above embodiments which is a chimeric antibody or a humanized antibody or a deimmunized antibody.
17. An antibody according to embodiment 13 which is a humanized and deimmunized antibody, wherein the heavy chain has the sequence of SEQ ID No:52 and the light chain has the sequence of SEQ ID No:54.
18. A macromolecule which is a chimeric molecule comprising an antibody or an antigen-binding fragment or mimetic thereof according to any of the above embodiments, wherein said antibody is associated with a functionally different molecule, said chimeric molecule being either a fusion chimeric protein or a conjugate resulting from covalent attachment of a chemical group or molecule, such as a PEG polymer or a labelled antibody.
19. A macromolecule according to any of the above embodiments, which is an affitin or an anticalin.
20. A macromolecule, in particular an antibody or antigen-binding fragment or mimetic thereof, according to any of the above embodiments which binds CD127 with a Kd lower than 5E-10 M, especially lower than 1E-10 M, especially lower than 5E-11 M.
21. A macromolecule, in particular an antibody or antigen-binding fragment or mimetic thereof, according to any of the above embodiments which exhibits cytotoxic activity towards CD127-positive cells.
22. A macromolecule, in particular an antibody or antigen-binding fragment or mimetic thereof, according to any of the above embodiments which does not increase the maturation of dendritic cells induced by TSLP, wherein the increase in dendritic cell maturation induced by TSLP is assessed by determining an elevated expression of cell surface marker CD40 and/or CD80 in TSLP receptor-positive cells treated with TSLP and with said macromolecule compared to cells treated with TSLP alone.
23. A macromolecule, in particular an antibody or antigen-binding fragment or mimetic thereof, according to embodiment 22 wherein the expression of CD80 is elevated by no more than 25%, preferably no more than 10%, in TSLP receptor-positive cells treated with TSLP and with said macromolecule, compared to cells treated with TSLP alone.
24. A macromolecule, in particular an antibody or antigen-binding fragment or mimetic thereof, according to embodiment 23 wherein the expression of CD80 is not elevated or is decreased in TSLP receptor-positive cells treated with TSLP and with said macromolecule, compared to cells treated with TSLP alone.
25. A macromolecule, in particular an antibody or antigen-binding fragment or mimetic thereof according to embodiment 22 wherein the expression of CD40 is elevated by no more than 50%, preferably no more than 25%, in TSLP receptor-positive cells treated with TSLP and with said macromolecule compared to cells treated with TSLP alone.
26. A macromolecule, in particular an antibody or antigen-binding fragment or mimetic thereof, according to embodiment 25 wherein the expression of CD40 is not elevated or is decreased in TSLP receptor-positive cells treated with TSLP and with said macromolecule, compared to cells treated with TSLP alone.
27. A nucleic acid molecule encoding an antibody or antigen-binding fragment thereof, or macromolecule of any of the above embodiments.
28. A nucleic acid molecule according to embodiment 27 which encodes an amino acid chosen from the group consisting of SEQ ID No:2; SEQ ID No:4; SEQ ID No:6; SEQ ID No:8; SEQ ID No:10; SEQ ID No:12; SEQ ID No:14; SEQ ID No:16; SEQ ID No:18; SEQ ID No:20; SEQ ID No:22; SEQ ID No:24; SEQ ID No:36; SEQ ID No:38; SEQ ID No:40; SEQ ID No:42; SEQ ID No:44; SEQ ID No:46; SEQ ID No:48; SEQ ID No:50; SEQ ID No:52; SEQ ID No:54 and SEQ ID No:56.
29. A nucleic acid molecule according to embodiment 28 which is chosen from the group consisting of SEQ ID No:1; SEQ ID No:3; SEQ ID No:5; SEQ ID No:7; SEQ ID No:9; SEQ ID No:11; SEQ ID No:13; SEQ ID No:15; SEQ ID No:17; SEQ ID No:19; SEQ ID No:21; SEQ ID No:23; SEQ ID No:35; SEQ ID No:37; SEQ ID No:39; SEQ ID No:41; SEQ ID No:43; SEQ ID No:45; SEQ ID No:47; SEQ ID No:49; SEQ ID No:51; SEQ ID No:53 and SEQ ID No:55.
30. A vector for the cloning and/or for the expression of a polynucleotide of any of embodiments 27 to 29, especially a plasmid, suitable for cloning and/or expressing in mammalian cells.
31. A cell or a cell line recombined with a polynucleotide according to any of embodiments 27 to 30, especially a mammalian cell or cell line.
32. A pharmaceutical composition comprising a macromolecule, in particular an antibody or antigen-binding fragment or mimetic thereof, according to any of embodiments 1 to 26, with a pharmaceutical vehicle, wherein said pharmaceutical composition optionally comprises a further, different, active ingredient.
33. A pharmaceutical composition comprising as a therapeutically active ingredient a macromolecule, in particular an antibody or antigen-binding fragment or mimetic thereof, according to any of embodiments 1 to 26 or a pharmaceutical composition of embodiment 32 in a formulation suitable for controlling dendritic cell differentiation/maturation when administered to a human patient.
34. A pharmaceutical composition of embodiments 32 or 33, which further comprises an additional compound having a therapeutic immunomodulator effect in particular on cells involved in an autoimmune disease or an allergic disease, leukemia such as acute lymphoblastic leukemia, lymphoma, a cancer disease, a chronic viral infection, inflammatory diseases, transplantation, respiratory diseases or autoimmunity.
35. A macromolecule, in particular an antibody or antigen-binding fragment or mimetic thereof according to any of embodiments 1 to 26 or a nucleic acid of any of embodiments 27 to 30 or a cell or cell line of embodiment 31 for use as a therapeutically active ingredient in a combination or in an add-on therapeutic regimen in a patient in need thereof.
36. A macromolecule, in particular an antibody or antigen-binding fragment or mimetic thereof according to any of embodiments 1 to 26 or a nucleic acid of any of embodiments 27 to 30 or a cell or cell line of embodiment 31 or a pharmaceutical composition of any of embodiments 32 to 34 for use in the treatment of a patient, in particular a human patient, with a disease.
37. A macromolecule, in particular an antibody or antigen-binding fragment or mimetic thereof according to any of embodiments 1 to 26 or a nucleic acid of any of embodiments 27 to 30 or a cell or cell line of embodiment 31 or a pharmaceutical composition of any of embodiments 32 to 34 for use in the treatment of a patient, in particular a human patient, at risk of a disease.
38. A macromolecule, nucleic acid, cell, cell lines or pharmaceutical composition for use according to embodiment 36 and/or embodiment 37, wherein the disease is an autoimmune disease, in particular rheumatoid arthritis, multiple sclerosis, type I diabetes, autoimmune thyroiditis and lupus.
39. A macromolecule, nucleic acid, cell, cell lines or pharmaceutical composition for use according to embodiment 36 and/or embodiment 37, wherein the disease is an inflammatory disease, in particular IBD and encephalomyelitis.
40. A macromolecule, nucleic acid, cell, cell lines or pharmaceutical composition for use according to embodiment 36 and/or embodiment 37, wherein the disease is an allergic disease.
41. A macromolecule, nucleic acid, cell, cell lines or pharmaceutical composition for use according to embodiment 36 and/or embodiment 37, wherein the disease is a cancer disease.
42. A macromolecule, nucleic acid, cell, cell lines or pharmaceutical composition for use according to embodiment 36 and/or embodiment 37, wherein the disease is a respiratory diseases.
43. A macromolecule, nucleic acid, cell, cell lines or pharmaceutical composition for use according to embodiment 36 and/or embodiment 37, wherein the disease is related to, in particular is a consequence of, transplantation.
44. A method of treatment comprising the administration of a macromolecule, in particular an antibody or antigen-binding fragment or mimetic thereof according to any of embodiments 1 to 26 or a nucleic acid of any of embodiments 27 to 30 or cell or cell line of embodiment 31 or pharmaceutical composition of embodiments 32 to 34 in a patient with or at risk of a disease.
45. A method of treatment according to embodiment 44, wherein the disease is an autoimmune disease, in particular rheumatoid arthritis, multiple sclerosis, type I diabetes, autoimmune thyroiditis and lupus.
46. A method of treatment according to embodiment 44, wherein the disease is an inflammatory disease, in particular IBD and encephalomyelitis.
47. A method of treatment according to embodiment 44, wherein the disease is an allergic disease.
48. A method of treatment according to embodiment 44, wherein the disease is a cancer disease.
49. A method of treatment according to embodiment 44, wherein the disease is a respiratory diseases.
50. A method of treatment according to embodiment 44, wherein the disease is related to, in particular is a consequence of, transplantation.
51. A macromolecule, in particular an antibody or antigen-binding fragment or mimetic thereof according to any of embodiments 1 to 26 or a nucleic acid of any of embodiments 27 to 30 or a cell or cell line of embodiment 31 or a pharmaceutical composition of any of embodiments 32 to 34 for use in the treatment of a patient, in particular a human patient, in need of transplantation and/or about to be transplanted and/or in a transplanted patient.
52. A method of treatment comprising the administration of a macromolecule, in particular an antibody or antigen-binding fragment or mimetic thereof according to any of embodiments 1 to 26 or a nucleic acid of any of embodiments 27 to 30 or cell or cell line of embodiment 31 or pharmaceutical composition of embodiments 32 to 34 in a patient in need of transplantation and/or about to be transplanted and/or in a transplanted patient.
53. An antigen wherein the epitope comprises or consists of sequences from site 2b of CD127, in particular comprising at least 3, 4, 5, 6 or 7 consecutive amino acids from site 2b of CD127.
54. An antigen according to embodiment 53, wherein the epitope comprises or consists of sequences from the site consisting of amino acids 109 to 127 of SEQ ID No:114, in particular from the site consisting of amino acids 110 to 125, 112 to 125, 112 to 120, in particular comprising at least 3, 4, 5, 6 or 7 consecutive amino acids from said site.
55. An antigen according to any of embodiments 53 or 54, wherein the epitope comprises at least 3, 4, 5, 6 or 7 consecutive amino acids of CD127, said consecutive amino acids comprising P112 and/or L115.
56. An antigen according to any of embodiments 53 to 55, wherein the epitope consists of or comprises the sequence of SEQ ID No:116, in particular comprises the sequence of SEQ ID No:86.
57. An antigen according to any of embodiments 53 to 56, wherein the epitope also comprises sequences, in particular at least 3, 4, 5, 6 or 7 consecutive amino acids, from the D1 domain of CD127, in particular from amino acids 1-98 of SEQ ID No:114.
58. An antigen according to embodiment 57, wherein the epitope comprises the sequence of human CD127 comprising or consisting of the sequence of SEQ ID No:115, in particular comprising or consisting of SEQ ID No:110
59. An antigen according to any of embodiments 53 to 58, wherein the epitope also comprises sequences, in particular at least 3, 4, 5, 6 or 7 consecutive amino acids, from amino acids 180-220 of SEQ ID No:114, in particular wherein said sequences from amino acids 180-220 of SEQ ID No:114 consists of or comprises the sequence of SEQ ID No:117, in particular comprises or consists of SEQ ID No:111.
60. An antigen according to any of embodiments 53 to 59, wherein the epitope consists of or comprises the sequences of human CD127 consisting of:
the sequence of SEQ ID No:110 or the sequence of SEQ ID No:115;
the sequence of of SEQ ID No:111 or the sequence of SEQ ID No:117; and
the sequence of SEQ ID No:86 or the sequence of SEQ ID No:116.
61. An antigen according to any of embodiments 53 to 60, wherein the epitope does not comprise more than 3, 4 or 5 consecutive amino acids from the sequence of amino acids 99-108 of SEQ ID No:114 and/or does not comprise more than 3, 4 or 5 consecutive amino acids from the sequence of amino acids 128-179 of SEQ ID No:114, and/or does not comprise more than 3, 4 or 5 consecutive amino acids from the sequence of amino acids 220-239 of SEQ ID No:114, in particular does not comprise more than 3, 4 or 5 consecutive amino acids from any of said amino acid sequences of SEQ ID No:114.
62. An antigen according to any of embodiments 53 or 60, wherein the epitope sequence of human CD127 comprising SEQ ID No:110 does not extend to comprise the amino acids adjacent to said sequence in the sequence of human CD127 by more than 1 N-terminal amino acid or by more than 7 C-terminal amino acids.
63. An antigen according to embodiment 61, wherein the epitope sequence of human CD127 comprising SEQ ID No:110 does not extend to comprise any of the N-terminal and/or C-terminal amino acids adjacent to said sequence in the sequence of human CD127.
64. An antigen according to any of embodiments 53 to 63, wherein the epitope sequence of human CD127 comprising SEQ ID No:111 does not extend to comprise the amino acids adjacent to said sequence in the sequence of human CD127 by more than 30 N-terminal amino acid or by more than 30 C-terminal amino acids.
65. An antigen according to embodiment 64, wherein the epitope sequence of human CD127 comprising SEQ ID No:111 does not extend to comprise any of the N-terminal and/or C-terminal amino acids adjacent to said sequence in the sequence of human CD127.
66. An antigen according to any of embodiments 53 to 65, wherein the epitope is a conformational epitope, in particular wherein the peptides from CD127 comprised in said epitope are in a conformation which mimics the conformation of the corresponding peptides in the native CD127 or the extracellular domain thereof, in particular in CD127 in its monomeric form without ligand, in its form bound to γc and/or in its form bound to IL7.
67. An antigen according to embodiment 66, wherein the epitope is a conformational epitope, in which the peptides from CD127 are bound to a rigid molecular backbone which maintains them in the desired conformation, in particular such an antigen obtained using the CLIPS technology.
68. An epitope as defined in any of embodiments 53 to 67.
69. A nucleic acid encoding an antigen as defined by any of embodiments 53 to 67.
70. A method of manufacturing an antibody comprising immunizing a non-human animal against an antigen as defined in any of embodiments 53 to 67.
71. A method of selecting an antibody, a fragment of an antibody or an antibody mimetic, in particular an antibody obtained as in embodiment 70 of fragment of mimetic thereof, comprising a step of assaying the binding capacity of said antibody to at least one antigen as defined in any of embodiments 53 to 67, in particular wherein said method comprises several successive such steps, each step assaying the binding capacity to a distinct peptide consisting of a single contiguous sequence of CD127.
72. A method of selecting a macromolecule, in particular an antibody, in particular an antibody obtained as in embodiment 70, or an antigen-binding fragment or mimetic of such an antibody, comprising or consisting of a step of testing the binding capacity of the macromolecule to CD127, in particular to an antigen thereof as defined in any of embodiments 53 to 67 and optionally selecting macromolecules according to embodiment 20.
73. A method of selecting a macromolecule according to any of embodiments 71 or 72, wherein the antigen comprises several non-contiguous peptides of CD127 and wherein the method comprises several steps, each of said step consisting of testing the binding capacity of the macromolecule to one of said peptides of CD127.
74. A method, in particular according to any of embodiments 71 to 73, of selecting a macromolecule, in particular an antibody, in particular an antibody obtained as in embodiment 70, or an antigen-binding fragment or mimetic of such an antibody, comprising or consisting of the step of testing the internalization of CD127 in CD127-expressing cells induced by the presence of the macromolecule.
75. A method, in particular according to any of embodiments 71 to 74, of selecting a macromolecule, in particular an antibody, in particular an antibody obtained as in embodiment 70, or an antigen-binding fragment or mimetic of such an antibody, comprising or consisting of the step of testing the inhibition by the macromolecule of IL7-induced internalization of CD127 in CD127-expressing cells and optionally selecting macromolecules according to embodiment 3.
76. A method, in particular according to any of embodiments 71 to 75, of selecting a macromolecule, in particular an antibody, in particular an antibody obtained as in embodiment 70, or an antigen-binding fragment or mimetic of such an antibody, comprising or consisting of the step of assaying the capacity of said macromolecule to disrupt, by its binding to CD127, the binding of CD127 to the γc chain.
77. A method, in particular according to any of embodiments 71 to 76, of selecting a macromolecule, in particular an antibody, in particular an antibody obtained as in embodiment 70, or an antigen-binding fragment or mimetic of such an antibody, comprising or consisting of the step of testing the increase of the maturation of DCs induced by TSLP in the presence of the macromolecule and optionally selecting macromolecules according to any of embodiments 22 to 26.
78. A method according to any of embodiments 71 to 77, further comprising one or more of the following steps:
  a. Testing the inhibition by the macromolecule of IL-7 induced signalling, in particular STAT5 phosphorylation;
  b. Testing the inhibition by the macromolecule of TSLP-induced production of TARC;
  c. Testing the inhibition by the macromolecule of the expression of α4, β7 and/or α4/β7 integrin expression, in particular cell surface expression on T-lymphocytes.

REFERENCES

Adams, A. B., Pearson, T. C., and Larsen, C. P. (2003). Heterologous immunity: an overlooked barrier to tolerance. Immunol. Rev. 196, 147-160.

Albuquerque, A. S., Cortesão, C. S., Foxall, R. B., Soares, R. S., Victorino, R. M. M., and Sousa, A. E. (2007). Rate of increase in circulating IL-7 and loss of IL-7Ralpha expression differ in HIV-1 and HIV-2 infections: two lymphopenic diseases with similar hyperimmune activation but distinct outcomes. J. Immunol. Baltim. Md 1950 178, 3252-3259.

Baca, M., Presta, L. G., O'Connor, S. J., and Wells, J. A. (1997). Antibody humanization using monovalent phage display. J. Biol. Chem. 272, 10678-10684.

Van Bodegom, D., Zhong, J., Kopp, N., Dutta, C., Kim, M.-S., Bird, L., Weigert, O., Tyner, J., Pandey, A., Yoda, A., et al. (2012). Differences in signaling through the B-cell leukemia oncoprotein CRLF2 in response to TSLP and through mutant JAK2. Blood 120, 2853-2863.

Boshuizen, R. S., Marsden, C., Turkstra, J., Rossant, C. J., Slootstra, J., Copley, C., and Schwamborn, K. (2014). A combination of in vitro techniques for efficient discovery of functional monoclonal antibodies against human CXC chemokine receptor-2 (CXCR2). mAbs 6, 1415-1424.

Bour-Jordan, H., Esensten, J. H., Martinez-Llordella, M., Penaranda, C., Stumpf, M., and Bluestone, J. A. (2011). Intrinsic and extrinsic control of peripheral T-cell tolerance by costimulatory molecules of the CD28/B7 family. Immunol. Rev. 241, 180-205.

Broux, B., Hellings, N., Venken, K., Rummens, J.-L., Hensen, K., Van Wijmeersch, B., and Stinissen, P. (2010). Haplotype 4 of the multiple sclerosis-associated interleukin-7 receptor alpha gene influences the frequency of recent thymic emigrants. Genes Immun. 11, 326-333.

Chassoux, D. M., Linares-Cruz, L. G., Bazin, H., and Stanislawski, M. (1988). K-cell-mediated cytotoxicity induced with rat monoclonal antibodies. I. Antibodies of various isotypes differ in their ability to induce cytotoxicity mediated by rat and human effectors. Immunology 65, 623-628.

Chothia, C., and Lesk, A. M. (1987). Canonical structures for the hypervariable regions of immunoglobulins. J. Mol. Biol. 196, 901-917.

Deininger, P. (1990). Molecular cloning: A laboratory manual: 2nd ed. Edited by J. Sambrook, E. F. Fritsch, and T. Maniatis. Cold Spring Harbor Laboratory Press, Cold Spring Harbor, NY, 1989 (in 3 volumes). Anal. Biochem. 186, 182-183.

Delves, P. J., Martin, S. J., Burton, D. R., and Roitt, I. M. (2011). Roitt's Essential Immunology (John Wiley & Sons).

Denucci, C. C., Mitchell, J. S., and Shimizu, Y. (2009). Integrin function in T-cell homing to lymphoid and non-lymphoid sites: getting there and staying there. Crit. Rev. Immunol. 29, 87-109.

Dustin, M. L., and Shaw, A. S. (1999). Costimulation: building an immunological synapse. Science 283, 649-650.

Edward G. Routledge, S. D. G. (1993). Reshaping antibodies for therapy. 13-44.

Flavell, D. J., Warnes, S. L., Bryson, C. J., Field, S. A., Noss, A. L., Packham, G., and Flavell, S. U. (2006). The anti-CD20 antibody rituximab augments the immunospecific therapeutic effectiveness of an anti-CD19 immunotoxin directed against human B-cell lymphoma. Br. J. Haematol. 134, 157-170.

Gaseitsiwe, S., Valentini, D., Mahdavifar, S., Reilly, M., Ehrnst, A., and Maeurer, M. (2010). Peptide microarray-based identification of *Mycobacterium tuberculosis* epitope binding to HLA-DRB1*0101, DRB1*1501, and DRB1*0401. Clin. Vaccine Immunol. CVI 17, 168-175.

Gorfu, G., Rivera-Nieves, J., and Ley, K. (2009). Role of beta7 integrins in intestinal lymphocyte homing and retention. Curr. Mol. Med. 9, 836-850.

Grakoui, A., Bromley, S. K., Sumen, C., Davis, M. M., Shaw, A. S., Allen, P. M., and Dustin, M. L. (1999). The immunological synapse: a molecular machine controlling T cell activation. Science 285, 221-227.

Haas, J., Korporal, M., Schwarz, A., Balint, B., and Wildemann, B. (2011). The interleukin-7 receptor α chain contributes to altered homeostasis of regulatory T cells in multiple sclerosis. Eur. J. Immunol. 41, 845-853.

Haudebourg, T., Poirier, N., and Vanhove, B. (2009). Depleting T-cell subpopulations in organ transplantation. Transpl. Int. Off. J. Eur. Soc. Organ Transplant. 22, 509-518.

He, R., and Geha, R. S. (2010). Thymic stromal lymphopoietin. Ann. N. Y. Acad. Sci. 1183, 13-24.

Henriques, C. M., Rino, J., Nibbs, R. J., Graham, G. J., and Barata, J. T. (2010). IL-7 induces rapid clathrin-mediated internalization and JAK3-dependent degradation of IL-7Ralpha in T cells. Blood 115, 3269-3277.

Von Horsten, H. H., Ogorek, C., Blanchard, V., Demmler, C., Giese, C., Winkler, K., Kaup, M., Berger, M., Jordan, I., and Sandig, V. (2010). Production of non-fucosylated antibodies by co-expression of heterologous GDP-6-deoxy-D-lyxo-4-hexulose reductase. Glycobiology 20, 1607-1618.

Inaba, K., Inaba, M., Witmer-Pack, M., Hatchcock, K., Hodes, R., and Steinman, R. M. (1995). Expression of B7 costimulator molecules on mouse dendritic cells. Adv. Exp. Med. Biol. 378, 65-70.

Jariwala, S. P., Abrams, E., Benson, A., Fodeman, J., and Zheng, T. (2011). The role of thymic stromal lymphopoietin in the immunopathogenesis of atopic dermatitis. Clin. Exp. Allergy J. Br. Soc. Allergy Clin. Immunol. 41, 1515-1520.

Kabat, E. A., Wu, T. T., Reid-Miller, M., Perry, H. M. and Gottesman, K. S. (1992) Sequences of Proteins of Immunological Interest (DIANE publishing, 1992).

Kern, B., Kraynov, E., Lee, L.-F., Ray, R. (2013). Receptor occupancy and internalization of an anti-IL-7 receptor antibody. Cytokine 63, 276-277.

Kern, B., Li, W., Bono, C., Lee, L.-F., and Kraynov, E. (2015). Receptor occupancy and blocking of STAT5 signaling by an anti-IL-7 receptor α antibody in cynomolgus monkeys. Cytometry B Clin. Cytom.

Krehenbrink, M., Chami, M., Guilvout, I., Alzari, P. M., Pécorari F., Pugsley A. P. (2008). Artificial binding proteins (Affitins) as probes for conformational changes in secretin PulD. J Mol Biol. 2008 Nov. 28.

Lefranc, M.-P., Giudicelli, V., Ginestoux, C., Bodmer, J., Müller, W., Bontrop, R., Lemaitre, M., Malik, A., Barbié, V., and Chaume, D. (1999). IMGT, the international ImMunoGeneTics database. Nucleic Acids Res. 27, 209-212.

Lei, L., Zhang, Y., Yao, W., Kaplan, M. H., and Zhou, B. (2011). Thymic Stromal Lymphopoietin Interferes with Airway Tolerance by Suppressing the Generation of Antigen-Specific Regulatory T Cells. J. Immunol. 186, 2254-2261.

Luo, H., Wu, Z., Qi, S., Jin, W., Han, B., Wu, J. (2011). Ephrinb1 and Ephrinb2 are associated with interleukin-7 receptor α and retard its internalization from the cell surface. J Biol Chem. 2011 Dec. 30; 286(52):44976-87.

Martin, A. C. R. (2001). Protein Sequence and Structure Analysis of Antibody Variable Domains. In Antibody Engineering, D. R. Kontermann, and D. S. Dübel, eds. (Springer Berlin Heidelberg), pp. 422-439.

Mazzucchelli, R., Hixon, J. A., Spolski, R., Chen, X., Li, W. Q., Hall, V. L., Willette-Brown, J., Hurwitz, A. A., Leonard, W. J., and Durum, S. K. (2008). Development of regulatory T cells requires IL-7Ralpha stimulation by IL-7 or TSLP. Blood 112, 3283-3292.

McElroy, C. A., Dohm, J. A., and Walsh, S. T. R. (2009). Structural and biophysical studies of the human IL-7/IL-7Ralpha complex. Struct. Lond. Engl. 1993 17, 54-65.

McElroy, C. A., Holland, P. J., Zhao, P., Lim, J.-M., Wells, L., Eisenstein, E., and Walsh, S. T. R. (2012). Structural reorganization of the interleukin-7 signaling complex. Proc. Natl. Acad. Sci. U.S.A. 109, 2503-2508

Michel, L., Berthelot, L., Pettré, S., Wiertlewski, S., Lefrère, F., Braudeau, C., Brouard, S., Soulillou, J.-P., and Laplaud, D.-A. (2008). Patients with relapsing-remitting multiple sclerosis have normal Treg function when cells expressing IL-7 receptor alpha-chain are excluded from the analysis. J. Clin. Invest. 118, 3411-3419.

Nancey, S., Hamzaoui, N., Moussata, D., Graber, I., Bienvenu, J., and Flourie, B. (2008). Serum interleukin-6, soluble interleukin-6 receptor and Crohn's disease activity. Dig. Dis. Sci. 53, 242-247.

Niederfellner, G., Lammens, A., Mundigl, O., Georges, G. J., Schaefer, W., Schwaiger, M., Franke, A., Wiechmann, K., Jenewein, S., Slootstra, J. W., et al. (2011). Epitope characterization and crystal structure of GA101 provide insights into the molecular basis for type I/II distinction of CD20 antibodies. Blood 118, 358-367.

Olivier, S., Jacoby, M., Brillon, C., Bouletreau, S., Mollet, T., Nerriere, O., Angel, A., Danet, S., Souttou, B., Guehenneux, F., et al. (2010). EB66 cell line, a duck embryonic stem cell-derived substrate for the industrial production of therapeutic monoclonal antibodies with enhanced ADCC activity. mAbs 2, 405-415.

Olkhanud, P. B., Rochman, Y., Bodogai, M., Malchinkhuu, E., Wejksza, K., Xu, M., Gress, R. E., Hesdorffer, C., Leonard, W. J., and Biragyn, A. (2011). Thymic stromal lymphopoietin is a key mediator of breast cancer progression. J. Immunol. Baltim. Md 1950 186, 5656-5662.

Van Oosterhout, Y. V., van Emst, J. L., Bakker, H. H., Preijers, F. W., Schattenberg, A. V., Ruiter, D. J., Evers, S., Koopman, J. P., and de Witte, T. (2001). Production of anti-CD3 and anti-CD7 ricin A-immunotoxins for a clinical pilot study. Int. J. Pharm. 221, 175-186.

Papac, D. I., Hoyes, J., and Tomer, K. B. (1994). Epitope mapping of the gastrin-releasing peptide/anti-bombesin monoclonal antibody complex by proteolysis followed by matrix-assisted laser desorption ionization mass spectrometry. Protein Sci. 3, 1485-1492.

Park, L. S., Martin, U., Garka, K., Gliniak, B., Di Santo, J. P., Muller, W., Largaespada, D. A., Copeland, N. G., Jenkins, N. A., Farr, A. G., et al. (2000). Cloning of the murine thymic stromal lymphopoietin (TSLP) receptor: Formation of a functional heteromeric complex requires interleukin 7 receptor. J. Exp. Med. 192, 659-670.

Paus, D., and Winter, G. (2006). Mapping epitopes and antigenicity by site-directed masking. Proc. Natl. Acad. Sci. U.S.A. 103, 9172-9177.

Poirier, N., Haudebourg, T., Brignone, C., Dilek, N., Hervouet, J., Minault, D., Coulon, F., de Silly, R. V., Triebel, F., Blancho, G., et al. (2011). Antibody-mediated depletion of lymphocyte-activation gene-3 (LAG-3(+))-activated T lymphocytes prevents delayed-type hypersensitivity in non-human primates. Clin. Exp. Immunol. 164, 265-274.

Racapé, M., Vanhove, B., Soulillou, J.-P., and Brouard, S. (2009). Interleukin 7 receptor alpha as a potential therapeutic target in transplantation. Arch. Immunol. Ther. Exp. (Warsz.) 57, 253-261.

Rader, C., Cheresh, D. A., and Barbas, C. F. (1998). A phage display approach for rapid antibody humanization: designed combinatorial V gene libraries. Proc. Natl. Acad. Sci. U.S.A. 95, 8910-8915.

Reche, P. A., Soumelis, V., Gorman, D. M., Clifford, T., Liu Mr, null, Travis, M., Zurawski, S. M., Johnston, J., Liu, Y. J., Spits, H., et al. (2001). Human thymic stromal lymphopoietin preferentially stimulates myeloid cells. J. Immunol. Baltim. Md 1950 167, 336-343.

Risberg, K., Fodstad, Ø., and Andersson, Y. (2011). Synergistic anticancer effects of the 9.2.27PE immunotoxin and ABT-737 in melanoma. PloS One 6, e24012.

Roan, F., Bell, B. D., Stoklasek, T. A., Kitajima, M., Han, H., and Ziegler, S. F. (2012). The multiple facets of thymic stromal lymphopoietin (TSLP) during allergic inflammation and beyond. J. Leukoc. Biol. 91, 877-886.

Rochman, Y., Kashyap, M., Robinson, G. W., Sakamoto, K., Gomez-Rodriguez, J., Wagner, K.-U., and Leonard, W. J. (2010). Thymic stromal lymphopoietin-mediated STAT5 phosphorylation via kinases JAK1 and JAK2 reveals a key difference from IL-7-induced signaling. Proc. Natl. Acad. Sci. U.S.A. 107, 19455-19460.

Rosok, M. J., Yelton, D. E., Harris, L. J., Bajorath, J., Hellström, K. E., Hellström, I., Cruz, G. A., Kristensson, K., Lin, H., Huse, W. D., et al. (1996). A combinatorial library strategy for the rapid humanization of anticarcinoma BR96 Fab. J. Biol. Chem. 271, 22611-22618.

Schlehuber, S., Skerra, A. (2002). Tuning ligand affinity, specificity, and folding stability of an engineered lipocalin variant—a so-called 'anticalin'—using a molecular random approach. Biophys Chem. 2002 May 2; 96(2-3):213-28

Shaw, A. S., and Dustin, M. L. (1997). Making the T cell receptor go the distance: a topological view of T cell activation. Immunity 6, 361-369.

Shinohara, T., Nemoto, Y., Kanai, T., Kameyama, K., Okamoto, R., Tsuchiya, K., Nakamura, T., Totsuka, T., Ikuta, K., and Watanabe, M. (2011). Upregulated IL-7 receptor α expression on colitogenic memory CD4+ T cells may participate in the development and persistence of chronic colitis. J. Immunol. Baltim. Md 1950 186, 2623-2632.

Shochat, C., Tal, N., Bandapalli, O. R., Palmi, C., Ganmore, I., te Kronnie, G., Cario, G., Cazzaniga, G., Kulozik, A. E., Stanulla, M., et al. (2011). Gain-of-function mutations in interleukin-7 receptor-α (IL7R) in childhood acute lymphoblastic leukemias. J. Exp. Med. 208, 901-908.

Skerra, A. (2008). Alternative binding proteins: anticalins—harnessing the structural plasticity of the lipocalin ligand pocket to engineer novel binding activities. FEBS J. 2008 June; 275(11):2677-83. doi: 10.1111/j.1742-4658.2008.06439.x. Epub 2008 Apr. 24.

Suckau, D., Köhl, J., Karwath, G., Schneider, K., Casaretto, M., Bitter-Suermann, D., and Przybylski, M. (1990). Molecular epitope identification by limited proteolysis of an immobilized antigen-antibody complex and mass spectrometric peptide mapping. Proc. Natl. Acad. Sci. U.S.A. 87, 9848-9852

Taylor, B. C., Zaph, C., Troy, A. E., Du, Y., Guild, K. J., Comeau, M. R., and Artis, D. (2009). TSLP regulates intestinal immunity and inflammation in mouse models of helminth infection and colitis. J. Exp. Med. 206, 655-667.

Teeling, J. L., Mackus, W. J. M., Wiegman, L. J. J. M., van den Brakel, J. H. N., Beers, S. A., French, R. R., van Meerten, T., Ebeling, S., Vink, T., Slootstra, J. W., et al. (2006). The biological activity of human CD20 monoclonal antibodies is linked to unique epitopes on CD20. J. Immunol. Baltim. Md 1950 177, 362-371.

Timmerman, P., Puijk, W. C., and Meloen, R. H. (2007). Functional reconstruction and synthetic mimicry of a conformational epitope using CLIPS technology. J. Mol. Recognit. JMR 20, 283-299.

Walsh, S. T. R. (2012). Structural insights into the common γ-chain family of cytokines and receptors from the interleukin-7 pathway. Immunol. Rev. 250, 303-316.

Watanabe, N., Wang, Y.-H., Lee, H. K., Ito, T., Wang, Y.-H., Cao, W., and Liu, Y.-J. (2005a). Hassall's corpuscles instruct dendritic cells to induce CD4+CD25+ regulatory T cells in human thymus. Nature 436, 1181-1185.

Watanabe, N., Hanabuchi, S., Marloie-Provost, M.-A., Antonenko, S., Liu, Y.-J., and Soumelis, V. (2005b). Human TSLP promotes CD40 ligand-induced IL-12 production by myeloid dendritic cells but maintains their Th2 priming potential. Blood 105, 4749-4751.

Ye, J., Ma, N., Madden, T. L., and Ostell, J. M. (2013). IgBLAST: an immunoglobulin variable domain sequence analysis tool. Nucleic Acids Res. 41, W34-W40.

Ying, S., O'Connor, B., Ratoff, J., Meng, Q., Fang, C., Cousins, D., Zhang, G., Gu, S., Gao, Z., Shamji, B., et al. (2008). Expression and cellular provenance of thymic stromal lymphopoietin and chemokines in patients with severe asthma and chronic obstructive pulmonary disease. J. Immunol. Baltim. Md 1950 181, 2790-2798.

Zhi, K., Li, M., Zhang, X., Gao, Z., Bai, J., Wu, Y., Zhou, S., Li, M., and Qu, L. (2014). α4β7 Integrin (LPAM-1) is upregulated at atherosclerotic lesions and is involved in atherosclerosis progression. Cell. Physiol. Biochem. Int. J. Exp. Cell. Physiol. Biochem. Pharmacol. 33, 1876-1887.

Zhong, J., Sharma, J., Raju, R., Palapetta, S. M., Prasad, T. S. K., Huang, T.-C., Yoda, A., Tyner, J. W., van Bodegom, D., Weinstock, D. M., et al. (2014). TSLP signaling pathway map: a platform for analysis of TSLP-mediated signaling. Database J. Biol. Databases Curation 2014, bau007.

---

The invention claimed is:

1. A method for inhibiting inflammation associated with interleukin-7 (IL-7) signaling, the method comprising administering an effective amount of a composition comprising an anti-human CD127 agent that antagonizes interleukin-7 receptor (IL-7R) signaling induced by interleukin-7 (IL7) to a patient in need thereof;
wherein said anti-human CD127 agent comprises an antibody or an antigen-binding fragment thereof which binds specifically to human CD127,
wherein said antibody or antigen-binding fragment thereof comprises a VH chain comprising the following amino acid sequences:
(a) VHCDR1 of SEQ ID NO: 10;
(b) VHCDR2 of SEQ ID NO: 12; and
(c) VHCDR3 of SEQ ID NO: 14 or of SEQ ID NO: 48; and
wherein said antibody or antigen-binding fragment thereof comprises a VL chain comprising the following amino acid sequences:
(d) VLCDR1 of SEQ ID NO: 16 or of SEQ ID NO: 50;
(e) VLCDR2 of SEQ ID NO: 18 or of SEQ ID NO: 52; and
(f) VLCDR3 of SEQ ID NO: 20.

2. The method according to claim 1, wherein activation or proliferation of CD127 positive cells is inhibited in the patient.

3. The method according to claim 1, wherein the composition further comprises an additional active ingredient, wherein the additional active ingredient is an antibody targeting T-cells or a recombinant protein or antibody targeting accessory cells.

4. The method according to claim 3, wherein the additional active ingredient has a therapeutic immunomodulatory effect on cells involved in an autoimmune disease, an allergic disease, leukemia, acute lymphoblastic leukemia, lymphoma, a chronic viral infection, an inflammatory disease, transplantation, or a respiratory disease.

5. The method according to claim 3, wherein the antibody targeting T-cells is an anti-CD3, anti-ICOS, or anti-CD28 antibody, wherein the recombinant protein is CTLA4Ig, or wherein the antibody is an anti-CD40 antibody.

6. The method according to claim 1, wherein the anti-human CD127 agent is administered in a combination or in an add-on therapeutic regimen in a patient in need thereof.

7. The method according to claim 1, wherein the antibody or antigen-binding fragment thereof is covalently attached to a chemical group or a biological group.

8. The method according to claim 1, wherein the anti-human CD127 agent is a chimeric antibody or a humanized antibody or a deimmunized antibody.

9. The method according to claim 1, wherein the composition is a pharmaceutical composition comprising the anti-human CD127 agent and a pharmaceutical vehicle.

10. The method according to claim 1, wherein the antibody or antigen-binding fragment thereof comprises six complementarity-determining regions (CDRs) consisting of the amino acid sequences VHCDR1 SEQ ID NO: 10, VHCDR2 SEQ ID NO: 12, VHCDR3 SEQ ID NO: 48, VLCDR1 SEQ ID NO: 50, VLCDR2 SEQ ID NO: 52, and VLCDR3 SEQ ID NO: 20.

11. The method according to claim 1, wherein the antibody or antigen-binding fragment thereof disrupts the binding of CD127 to the γc common chain of cytokine receptors.

12. The method according to claim 1, wherein the antibody or antigen-binding fragment thereof does not increase the maturation of dendritic cells induced by Thymic Stromal Lymphopoietin (TSLP).

13. The method according to claim 1, wherein the antibody or antigen-binding fragment thereof does not induce internalization of CD127 in cells incubated with said antibody or antigen-binding fragment thereof as compared to cells incubated in the absence of said antibody or antigen-binding fragment thereof.

14. The method according to claim 1, wherein the antibody or antigen-binding fragment thereof in presence of IL7 does not significantly decrease the cell surface expression of CD127, and/or inhibits the internalization of CD127, as compared to cells incubated with interleukin 7 (IL-7) and in the absence of said antibody or antigen-binding fragment thereof.

15. The method according to claim 1, wherein the antibody or antigen-binding fragment thereof comprises:
   (i) a heavy chain comprising the amino acid sequence of SEQ ID NO: 22, SEQ ID NO: 36, SEQ ID NO: 38, or SEQ ID NO: 40; and
   (ii) a light chain comprising the amino acid sequence of SEQ ID NO: 24, SEQ ID NO: 42, SEQ ID NO: 44, or SEQ ID NO: 46.

16. The method according to claim 1, wherein the antibody or antigen-binding fragment thereof comprises:
   (i) a heavy chain with the amino acid sequence of SEQ ID NO: 2, SEQ ID NO: 6, or SEQ ID NO: 54; and
   (ii) a light chain with the amino acid sequence of SEQ ID NO: 4 or SEQ ID NO: 56.

17. The method according to claim 1, wherein the inflammation associated with interleukin-7 (IL-7) signaling is associated with a pathological condition involving the activation or proliferation of CD127 positive cells.

18. The method according to claim 1, wherein the inflammation associated with interleukin-7 (IL-7) signaling is associated with a cancer.

19. The method according to claim 1, wherein the inflammation associated with interleukin-7 (IL-7) signaling is associated with an allergic disease.

20. The method according to claim 1, wherein the inflammation associated with interleukin-7 (IL-7) signaling is associated with a respiratory disease.

21. The method according to claim 1, wherein the inflammation associated with interleukin-7 (IL-7) signaling is associated with a disease related to transplantation.

* * * * *